United States Patent
Wagner et al.

(10) Patent No.: US 6,475,985 B1
(45) Date of Patent: Nov. 5, 2002

(54) NUCLEOSIDES WITH ANTIVIRAL AND ANTICANCER ACTIVITY

(75) Inventors: Carston R. Wagner, St. Paul, MN (US); George W. Griesgraber, Eagan, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 09/647,206

(22) PCT Filed: Mar. 26, 1999

(86) PCT No.: PCT/US99/06467
§ 371 (c)(1),
(2), (4) Date: Sep. 27, 2000

(87) PCT Pub. No.: WO99/49873
PCT Pub. Date: Oct. 7, 1999

Related U.S. Application Data

(60) Provisional application No. 60/079,570, filed on Mar. 27, 1998.

(51) Int. Cl.$^7$ .................. A61K 31/70; A61K 38/02; A61K 38/14; C07K 2/00; C07K 9/00
(52) U.S. Cl. .................. 514/7; 514/8; 514/47; 514/48; 514/51; 514/52; 530/322; 536/26.1; 536/26.7; 536/26.74; 536/26.8; 536/26.9; 536/29.2
(58) Field of Search .................. 514/2, 8, 47, 48, 514/49, 51, 52, 23, 7; 530/300, 322; 536/26.1, 26.7, 26.74, 26.8, 26.9

(56) References Cited

U.S. PATENT DOCUMENTS

| 5,543,390 A | 8/1996 | Yatvin et al. ............. 514/2 |
| 5,614,504 A | 3/1997 | Hadden et al. ............. 514/45 |
| 5,659,023 A | 8/1997 | Alexander et al. ......... 536/22.1 |
| 5,696,097 A | 12/1997 | Matsuda et al. ............. 514/51 |

FOREIGN PATENT DOCUMENTS

| WO | 90/05736 | 5/1990 | ......... C07H/19/00 |
| WO | 96/29336 | 9/1996 | ......... C07H/19/10 |
| WO | 97/21452 | 6/1997 | ......... A61K/47/48 |

OTHER PUBLICATIONS

Abraham, T.W., et al., "Synthesis and Biological Activity of Aromatic Amino Acid Phosphoramidates of 5–Fluoro–2'–deoxyuridine and 1–β–Arabinofuranosylcotosine: Evidence of Phosphoramidase Activity", *J. Med. Chem.*, 39, pp. 4569–4575, (1996).

McGuigan, C., et al., "Intracellular Delivery of Bioactive AZT Nucleotides by Aryl Phosphate Derivatives of AZT", *J. Med. Chem.*, 36, pp. 1048–1052, (1993).

McIntee, E.J., et al., "Probing the Mechanism of Action and Decomposition of Amino Acid Phosphomonoester Amidates of Antiviral Nucleoside Prodrugs", *J. Med. Chem.*, 40, pp. 3323–3331, (1997).

*Primary Examiner*—Jeffrey E. Russel
(74) *Attorney, Agent, or Firm*—Schwegman, Lundberg, Woessner & Kluth, P.A.

(57) ABSTRACT

The invention provides nucleosides of formulae (I), (II), (V) and (VII) as described in the specification which possess antiviral and anticancer activity. Treatment of breast cancer is a preferred embodiment.

101 Claims, 9 Drawing Sheets

| Compound | R | R' | X | * |
|---|---|---|---|---|
| 5 | methoxy | benzyl | O | (S) |
| 6 | methoxy | 3-indolylmethyl | O | (S) |
| 7 | methoxy | benzyl | CH$_2$ | (S) |
| 14 | methylamino | benzyl | O | (S) |
| 16 | methylamino | 3-indolymethyl | O | (S) |

FIGURE 2
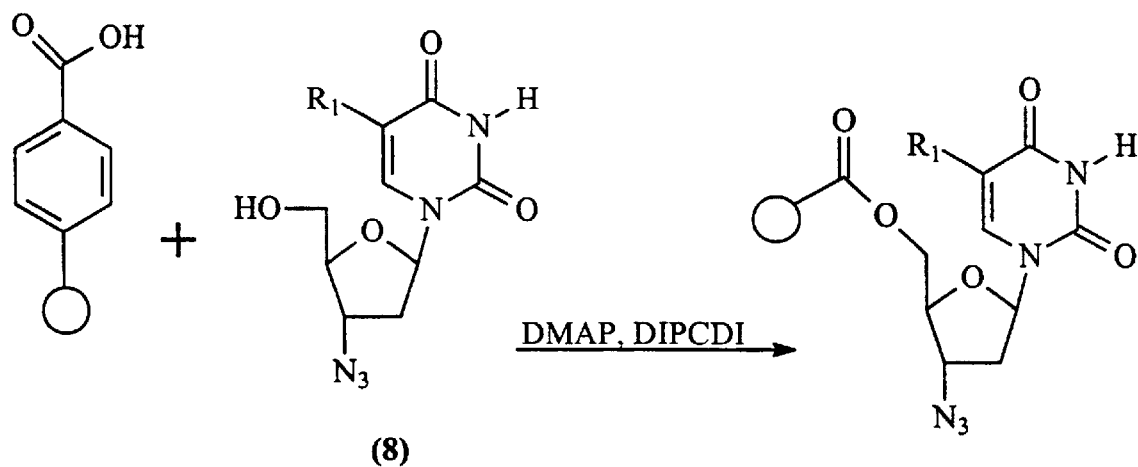
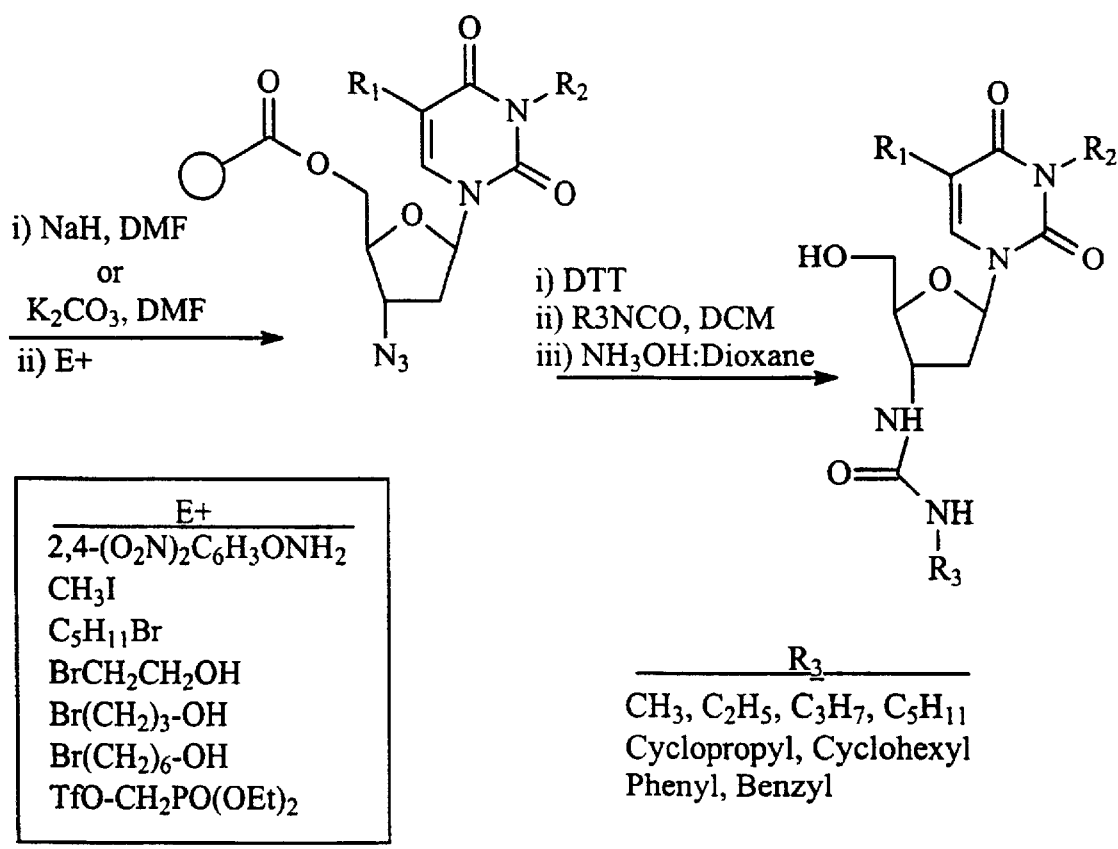

FIGURE 4
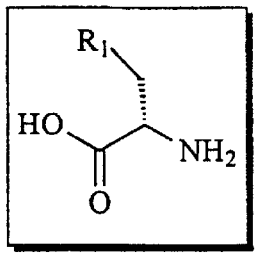
1) CH₃  2) CH₂CH₃
3) 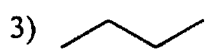
4) 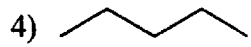
5) 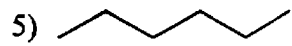
6) 
7) 
8) 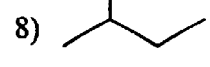
9) 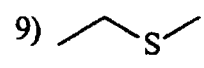
10) 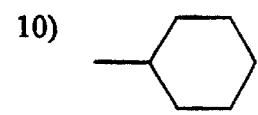
11) 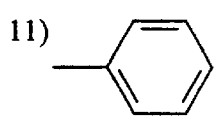
12) 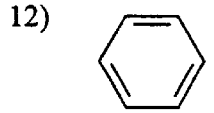
13) 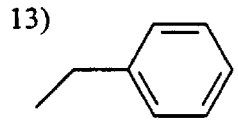
14) 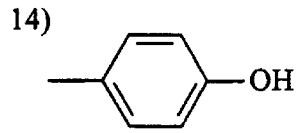
15) 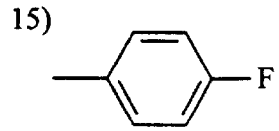
16) 
17) 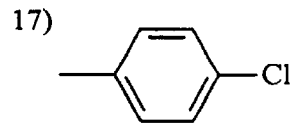
18) 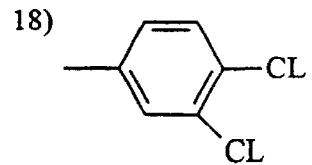
19) 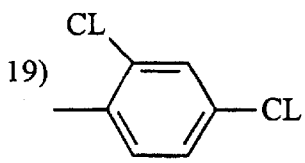
20) 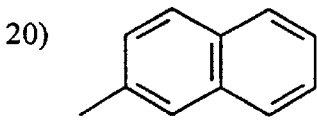
21) 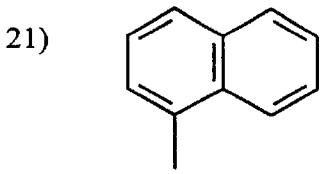
22) 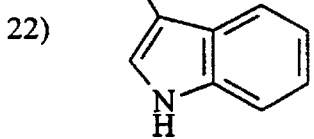
23) 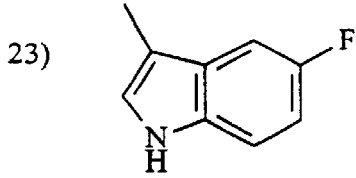
24) 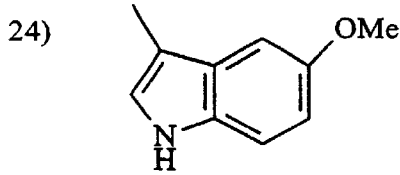

9 R = Indolyl
11 R = Phenyl

10 R = Indolyl
12 R = Phenyl

| Compound | R | R' | X | * |
|---|---|---|---|---|
| 5 | methoxy | benzyl | O | (S) |
| 6 | methoxy | 3-indolylmethyl | O | (S) |
| 7 | methoxy | benzyl | CH$_2$ | (S) |
| 14 | methylamino | benzyl | O | (S) |
| 16 | methylamino | 3-indolymethyl | O | (S) |

FIGURE 8

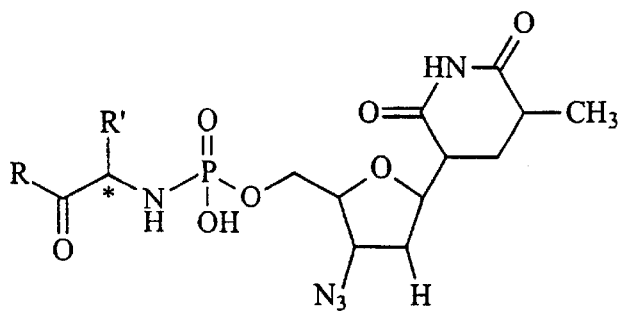

| Compound | R | R' | * |
|---|---|---|---|
| 9 | methoxy | 3-indolymethyl | (S) |
| 10 | methoxy | 3-indolymethyl | (R) |
| 11 | methoxy | benzyl | (S) |
| 12 | methoxy | benzyl | (R) |
| 17 | methoxy | hydrogen | - |
| 19 | methoxy | methyl | (S) |
| 20 | methoxy | isopropyl | (S) |
| 21 | methoxy | 2-methylpropyl | (S) |
| 22 | methoxy | 4-hydroxybenzyl | (S) |
| 23 | methylamino | hydrogen | - |
| 24 | methylamino | methyl | (S) |
| 25 | methylamino | isopropyl | (S) |
| 26 | methylamino | 2-methylpropyl | (S) |
| 27 | methylamino | benzyl | (S) |
| 28 | methylamino | benzyl | (R) |
| 29 | methylamino | 4-hydroxybenzyl | (S) |
| 30 | methylamino | 3-indolymethyl | (S) |
| 31 | methylamino | 3-indolymethyl | (R) |
| 32 | ethylamino | 3-indolymethyl | (S) |
| 33 | isopropylamino | 3-indolymethyl | (S) |
| 34 | cyclopropylamino | 3-indolymethyl | (S) |
| 35 | cyclohexylamino | 3-indolymethyl | (S) |

NUCLEOSIDES WITH ANTIVIRAL AND ANTICANCER ACTIVITY

CROSS REFERENCE TO RELATED APPLICATION

This application is a national stage filing under 35 U.S.C. § 371 of PCT/US99/06467, Mar. 26, 1999; which claims priority under 35 U.S.C. 119(e) U.S. Provisional Application Ser. No. 60/079,570, filed Mar. 27, 1998.

GOVERNMENT FUNDING

This invention was made with government support awarded by National Institutes of Health #R29-CA61908. The Government has certain rights in this invention.

BACKGROUND OF THE INVENTION

Chemotherapeutic nucleosides that function as inhibitors of polymerases must be phosphorylated intracellularly by endogenous nucleoside kinases to their respective mono-, di- and tri-phosphate derivatives. Unfortunately, biological targets, such as the herpes-virus or tumor cells, can readily become resistant to these nucleosides by either altering or removing the nucleoside kinase responsible for mono-phosphorylation. For example, the efficacy of antiviral nucleosides against HIV is reduced in monocytes and macrophages, since they contain only low levels of nucleoside kinases. In addition, in quiescent lymphocytes, thymidine analogs, such as AZT, are poorly phosphorylated. Because of these concerns, a number of approaches have been developed for the delivery of mono- and diphosphorylated nucleosides.

Recently, several attempts have been made to increase the therapeutic index of AZT by delivering the phosphorylated compound in the form of a phosphate or phosphoramidate prodrug. In particular, due largely to their reduced cytotoxicity, hydrophobic alkyl and aryl triesters of glycine, alanine, leucine, and phenylalanine phosphoramidates of AZT are highly effective and selective inhibitors of HIV viral replication.

In spite of these efforts, a continuing need exists for chemotherapeutic agents with antiviral and or anticancer properties.

SUMMARY OF THE INVENTION

The present invention provides compounds that act as antiviral and or anticancer agents. Accordingly there is provided a compound of the invention which is a compound of formula I:

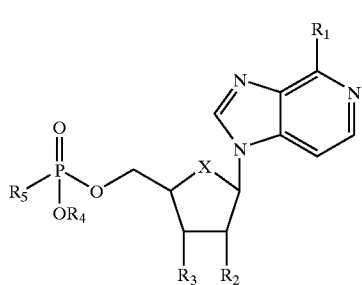

wherein
R$_1$ is hydrogen, halo, hydroxy, (C$_1$–C$_6$)alkyl, (C$_3$–C$_6$)cycloalkyl, (C$_1$–C$_6$)alkoxy, (C$_3$–C$_6$)cycloalkyloxy, (C$_1$–C$_6$)alkanoyl, (C$_1$–C$_6$)alkanoyloxy, trifluoromethyl, or NR$_a$R$_b$;

R$_2$ and R$_3$ are each independently hydrogen, halo, hydroxy, (C$_1$–C$_6$)alkyl, (C$_3$–C$_6$)cycloalkyl, (C$_1$–C$_6$)alkoxy, (C$_3$–C$_6$)cycloalkyloxy, (C$_1$–C$_6$)alkanoyl, (C$_1$–C$_6$)alkanoyloxy, trifluoromethyl, azido, cyano, or NR$_c$R$_d$;

R$_4$ is hydrogen, (C$_1$–C$_6$)alkyl, (C$_3$–C$_6$)cycloalkyl, aryl (C$_1$–C$_6$)alkyl, or 2-cyanoethyl, wherein any aryl ring may optionally be substituted with 1, 2, or 3 halo, hydroxy, (C$_1$–C$_6$)alkyl, (C$_3$–C$_6$)cycloalkyl, (C$_1$–C$_6$)alkoxy, (C$_3$–C$_6$)cycloalkyloxy, (C$_1$–C$_6$)alkanoyl, (C$_1$–C$_6$)alkanoyloxy, trifluoromethyl, trifluoromethoxy, nitro, cyano, or amino;

R$_5$ is an amino acid or a peptide;

X is oxy (—O—) thio (—S—) or methylene (—CH$_2$—);

R$_a$ and R$_b$ are each independently hydrogen, (C$_1$–C$_6$)alkyl, (C$_3$–C$_6$)cycloalkyl, phenyl, benzyl, phenethyl, or (C$_1$–C$_6$)alkanoyl; or R$_a$ and R$_b$ together with the nitrogen to which they are attached are pyrrolidino, piperidino or morpholino;

R$_c$ and R$_d$ are each independently hydrogen, (C$_1$–C$_6$)alkyl, (C$_3$–C$_6$)cycloalkyl, phenyl, benzyl, phenethyl, (C$_1$–C$_6$)alkanoyl, —C(=O)N(R$_e$)(R$_f$), or —C(=O)OR$_g$; or R$_c$ and R$_d$ together with the nitrogen to which they are attached are pyrrolidino, piperidino or morpholino;

R$_e$ and R$_f$ are each independently hydrogen, (C$_1$–C$_6$)alkyl, (C$_3$–C$_6$)cycloalkyl, phenyl, benzyl, or phenethyl; or R$_e$ and R$_f$ together with the nitrogen to which they are attached are pyrrolidino, piperidino or morpholino; and R$_g$ is hydrogen, (C$_1$–C$_6$)alkyl, (C$_3$–C$_6$)cycloalkyl, phenyl, benzyl, or phenethyl;

or a pharmaceutically acceptable salt thereof.

The invention also provides a compound of formula I wherein R$_1$–R$_4$ have any of the values described herein, and wherein R$_5$ is a nitrogen linked radical of formula III:

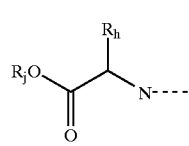

wherein R$_h$ is hydrogen, (C$_1$–C$_6$)alkyl, (C$_3$–C$_6$)cycloalkyl, (C$_3$–C$_6$)cycloalkyl(C$_1$–C$_6$)alkyl, (C$_1$–C$_6$)alkyl-S—)C$_1$–C$_6$) alkyl-, aryl, heteroaryl, aryl(C$_1$–C$_6$)alkyl, or heteroaryl (C$_1$–C$_6$)alkyl; wherein any aryl or heteroaryl may optionally be substituted with 1, 2, or 3 Z; R$_j$ is hydrogen, (C$_1$–C$_6$)alkyl, (C$_3$–C$_6$)cycloalkyl, (C$_3$–C$_6$)cycloalkyl(C$_1$–C$_6$)alkyl, phenyl, benzyl, or phenethyl; and wherein each Z is independently halo, hydroxy, (C$_1$–C$_6$)alkyl, (C$_3$–C$_6$)cycloalkyl, (C$_1$–C$_6$)alkoxy, (C$_3$–C$_6$)cycloalkyloxy, (C$_1$–C$_6$)alkanoyl, (C$_1$–C$_6$)alkanoyloxy, trifluoromethyl, trifluoromethoxy, nitro, cyano, or amino. Preferably, the carbon bearing R$_h$ has the (S) configuration.

The invention also provides a compound of formula I wherein R$_1$–R$_4$ have any of the values described herein, and wherein R$_5$ is a nitrogen-linked radical of formula VI:

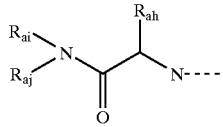

wherein $R_{ah}$ is hydrogen, $(C_1-C_6)$alkyl, $(C_3-C_6)$cycloalkyl, $(C_3-C_6)$cycloalkyl$(C_1-C_6)$alkyl, $(C_1-C_6)$alkyl-S—$(C_1-C_6)$alkyl-, aryl, heteroaryl, aryl$(C_1-C_6)$alkyl, or heteroaryl $(C_1-C_6)$alkyl; wherein any aryl or heteroaryl may optionally be substituted with 1, 2, or 3 Z; $R_{ai}$ and $R_{aj}$ are each independently hydrogen, $(C_1-C_6)$alkyl, $(C_3-C_6)$cycloalkyl, $(C_3-C_6)$cycloalkyl$(C_1-C_6)$alkyl, phenyl, benzyl, or phenethyl; and each Z is independently halo, hydroxy, $(C_1-C_6)$alkyl, $(C_3-C_6)$cycloalkyl, $(C_1-C_6)$alkoxy, $(C_3-C_6)$cycloalkyloxy, $(C_1-C_6)$alkanoyl, $(C_1-C_6)$alkanoyloxy, trifluoromethyl, trifluoromethoxy, nitro, cyano, or amino. Preferably, the carbon bearing $R_{ah}$ has the (S) configuration.

The invention also provides a compound of formula II:

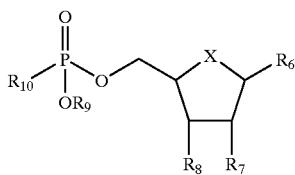

wherein $R_6$ is adenine, guanine, cytosine, thymine, or uracil, optionally substituted by 1, 2, or 3 Y; wherein each Y is independently halo, hydroxy $(C_1-C_6)$alkyl, $(C_3-C_6)$cycloalkyl, $(C_1-C_6)$alkoxy, $(C_3-C_6)$cycloalkyloxy, $(C_1-C_6)$alkanoyl, $(C_1-C_6)$alkanoyloxy, trifluoromethyl, hydroxy$(C_1-C_6)$alkyl, —$(CH_2)_{1-4}P(=O)(OR_k)_2$ aryl, aryl$(C_1-C_6)$alkyl, or $NR_mR_n$, and wherein any aryl ring may optionally be substituted with 1, 2, or 3 halo, hydroxy, $(C_1-C_6)$alkyl, $(C_3-C_6)$cycloalkyl, $(C_1-C_6)$alkoxy, $(C_3-C_6)$cycloalkyloxy, $(C_1-C_6)$alkanoyl, $(C_1-C_6)$alkanoyloxy, trifluoromethyl, trifluoromethoxy, nitro, cyano, or amino;

one of $R_7$ and $R_8$ is —$NR(R_o)C(=O)N(R_q)$, or —$N(R_o)C(=O)OR_r$, and the other is hydrogen, halo, hydroxy, $(C_1-C_6)$alkyl, $(C_3-C_6)$cycloalkyl, $(C_1-C_6)$alkoxy, $(C_3-C_6)$cycloalkyloxy, $(C_1-C_6)$alkanoyloxy, trifluoromethyl, azido, cyano, or $RN_sR_t$;

$R_9$ is hydrogen, $(C_1-C_6)$alkyl, $(C_3-C_6)$cycloalkyl, aryl $(C_1-C_6)$alkyl, or 2-cyanoethyl, wherein any aryl ring may optionally be substituted by 1, 2, or 3 halo, hydroxy, $(C_1-C_6)$alkyl, $(C_3-C_6)$cycloalkyl, $(C_1-C_6)$alkoxy, $(C_3-C_6)$cycloalkyloxy, $(C_1-C_6)$alkanoyl, $(C_1-C_6)$alkanoyloxy, trifluoromethyl, trifluoromethoxy, nitro, cyano, or amino;

$R_{10}$ is an amino acid or a peptide;

X is oxy, thio, or methylene;

each $R_k$ is independently hydrogen or $(C_1-C_6)$alkyl;

$R_m$ and $R_n$ are each independently hydrogen, $(C_1-C_6)$alkyl, $(C_3-C_6)$cycloalkyl, phenyl, benzyl, phenethyl, or $(C_1-C_6)$alkanoyl; or $R_m$ and $R_n$ together with the nitrogen to which they are attached are pyrrolidino, piperidino or morpholino;

$R_o$ is hydrogen, $(C_1-C_6)$alkyl, $(C_3-C_6)$cycloalkyl, phenyl, benzyl, or phenethyl;

$R_p$ and $R_q$ are each independently hydrogen, $(C_1-C_6)$alkyl, $(C_3-C_6)$cycloalkyl, phenyl, benzyl, or phenethyl; or $R_p$ and $R_q$ together with the nitrogen to which they are attached are pyrrolidino, piperidino or morpholino; and $R_r$ is hydrogen, $(C_1-C_6)$alkyl, $(C_3-C_6)$cycloalkyl, phenyl, benzyl, or phenethyl; and $R_s$ and $R_t$ are each independently hydrogen, $(C_1-C_6)$alkyl, $(C_3-C_6)$cycloalkyl, phenyl, benzyl, phenethyl, or $(C_1-C_6)$alkanoyl; or $R_s$ and $R_t$ together with the nitrogen to which they are attached are pyrrolidino, piperidino or morpholino;

or a pharmaceutically acceptable salt thereof.

The invention also provides a compound of formula V:

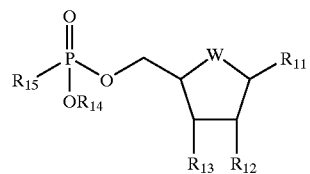

wherein $R_{11}$ is adenine, guanine, cytosine, thymine, or uracil, optionally substituted by 1, 2, or 3 U; wherein each U is independently halo, hydroxy, $(C_1-C_6)$alkyl, $(C_3-C_6)$cycloalkyl, $(C_1-C_6)$alkoxy, $(C_3-C_6)$cycloalkyloxy, $(C_1-C_6)$alkanoyl, $(C_1-C_6)$alkanoyloxy, trifluoromethyl, hydroxy$(C_1-C_6)$alkyl, —$(CH_2)_{1-4}P(=O)(OR_w)_2$ aryl, aryl$(C_1-C_6)$alkyl, or $NR_xR_y$;

one of $R_{12}$ and $R_{13}$ is azido and the other is hydrogen, halo, hydroxy, $(C_1-C_6)$alkyl, $(C_3-C_6)$cycloalkyl, $(C_1-C_6)$alkoxy, $(C_3-C_6)$cycloalkyloxy, $(C_1-C_6)$alkanoyl, $(C_1-C_6)$alkanoyloxy, trifluoromethyl, azido, cyano, —$N(R_z)C(=O)N(R_{aa})(R_{ab})$, —$N(R_z)C(=O)OR_{ac}$, or $NR_{ad}R_{ae}$;

$R_{14}$ is hydrogen, $(C_1-C_6)$alkyl, $(C_3-C_6)$cycloalkyl, aryl, aryl$(C_1-C_6)$alkyl, or 2-cyanoethyl, wherein any aryl ring may optionally be substituted by 1, 2, or 3 halo, hydroxy, $(C_1-C_6)$alkyl, $(C_3-C_6)$cycloalkyl, $(C_1-C_6)$alkoxy, $(C_3-C_6)$cycloalkyloxy, $(C_1-C_6)$alkanoyl, $(C_1-C_6)$alkanoyloxy, trifluoromethyl, trifluoromethoxy, nitro, cyano, or amino;

$R_{15}$ is an amino acid or a peptide;

W is oxy, thio, or methylene;

each $R_w$ is independently hydrogen or $(C_1-C_6)$alkyl;

$R_x$ and $R_y$ are each independently hydrogen, $(C_1-C_6)$alkyl, $(C_3-C_6)$cycloalkyl, phenyl, benzyl, phenethyl, or $(C_1-C_6)$alkanoyl; or $R_x$ and $R_y$ together with the nitrogen to which they are attached are pyrrolidino, piperdino or morpholino;

$R_z$ is hydrogen, $(C_1-C_6)$alkyl, $(C_3-C_6)$cycloalkyl, phenyl, benzyl, or phenethyl;

$R_{aa}$ and $R_{ab}$ are each independently hydrogen, $(C_1-C_6)$alkyl, $(C_3-C_6)$cycloalkyl, phenyl, benzyl, or phenethyl; or $R_{aa}$ and $R_{ab}$ together with the nitrogen to which they are attached are pyrrolidino, piperidino or morpholino; and $R_{ac}$ is hydrogen, $(C_1-C_6)$alkyl, $(C_3-C_6)$cycloalkyl, phenzyl, benzyl, or phenethyl; and $R_{ad}$ and $R_{ae}$ are each independently hydrogen, $(C_1-C_6)$alkyl, $(C_3-C_6)$cycloalkyl, phenyl, benzyl, phenethyl, or $(C_1-C_6)$alkanoyl; or $R_{ad}$ and $R_{ae}$ together with the nitrogen to which they are attached are pyrrolidino, piperidino or morpholino;

or a pharmaceutically acceptable salt thereof.

The invention also provides a compound of formula VII:

$$\text{VII}$$

[Structure: $R_{20}$—P(=O)(OR$_{19}$)—O—CH$_2$—[ring with W, $R_{16}$, $R_{17}$, $R_{18}$]]

wherein $R_{16}$ is adenine, guanine, cytosine, thymine, 3-deazaadenine, or uracil, optionally substituted by 1, 2, or 3 U; wherein each is independently halo, hydroxy, $(C_1-C_6)$alkyl, $(C_3-C_6)$cycloalkyl, $(C_1-C_6)$alkoxy, $(C_3-C_6)$cycloalkyloxy, $(C_1-C_6)$alkanoyl, $(C_1-C_6)$alkanoyloxy, trifluoromethyl, hydroxy$(C_1-C_6)$alkyl, —(CH$_2$)$_{1-4}$P(=O)(OR$_w$)$_2$ aryl, aryl$(C_1-C_6)$alkyl, or NR$_x$R$_y$;

one of $R_{17}$ and $R_{18}$ is hydroxy and the other is hydrogen, halo, hydroxy, $(C_1-C_6)$alkyl, $(C_3-C_6)$cycloalkyl, $(C_1-C_6)$alkoxy, $(C_3-C_6)$cycloalkyloxy, $(C_1-C_6)$alkanoyl, $(C_1-C_6)$alkanoyloxy, trifluoromethyl, azido, cyano, —N(R$_z$)C(=O)N(R$_{aa}$)(R$_{ab}$), —N(R$_z$)C(=O)OR$_{ac}$, or NR$_{ad}$R$_{ae}$;

R is hydrogen, (C—C)alkyl, (C—C)cycloalkyl, aryl, aryl (C—C$_6$)alkyl, or 2-cyanoethyl, wherein any aryl ring may optionally be substituted by 1, 2, or 3 halo, hydroxy, $(C_1-C_6)$alkyl, $(C_3-C_6)$cycloalkyl, $(C_1-C_6)$alkoxy, $(C_3-C_6)$cycloalkyloxy, $(C_1-C_6)$alkanoyloxy, $(C_1-C_6)$alkanoyloxy, trifluoromethyl, trifluoromethoxy, nitro, cyano, or amino;

$R_{20}$ is an amino acid or a peptide;

W is oxy, thio, or methylene;

each $R_w$ is independently hydrogen or $(C_1-C_6)$alkyl;

$R_x$ and $R_y$ are each independently hydrogen, $(C_1-C_6)$alkyl, $(C_3-C_6)$cycloalkyl, phenyl, benzyl, phenethyl, or $(C_1-C_6)$alkanoyl; or $R_x$ and $R_y$ together with the nitrogen to which they are attached are pyrrolidino, piperdino or morpholino;

$R_z$ is hydrogen, $(C_1-C_6)$alkyl, $(C_3-C_6)$cycloalkyl, phenyl, benzyl, or phenethyl;

$R_{aa}$ and $R_{ab}$ are each independently hydrogen, $(C_1-C_6)$alkyl, $(C_3-C_6)$cycloalkyl, phenyl, benzyl, or phenethyl; or $R_{aa}$ and $R_{ab}$ together with the nitrogen to which they are attached are pyrrolidino, piperdino or morpholino; and $R_{ac}$ is hydrogen, $(C_1-C_6)$alkyl, $(C_3-C_6)$cycloalkyl, phenyl, benzyl, or phenethyl; and $R_{ad}$ and $R_{ae}$ are each independently hydrogen, $(C_1-C_6)$alkyl, $(C_3-C_6)$cycloalkyl, phenyl, benzyl, pheneyl, or $(C_1-C_6)$alkanoyl; or $R_{ad}$ and $R_{ae}$ together with the nitrogen to which they are attached are pyrrolidino, piperidino or morpholino;

or a pharmaceutically acceptable salt thereof.

The invention also provides a compound of formula II wherein $R_{6-R9}$ have any of the values described herein, and wherein $R_{10}$ is a nitrogen linked radical of formula III as described hereinabove.

The invention also provides a compound of formula V wherein $R_{11}-R_{14}$ have any of the values described herein, and wherein $R_{15}$ is a nitrogen linked radical of formula III as described hereinabove.

The invention also provides a compound of formula VII wherein $R_{16}-R_{19}$ have any of the values described herein, and wherein $R_{20}$ is a nitrogen linked radical of formula III as described hereinabove.

The invention also provides a compound of formula II wherein $R_6-R_9$ have any of the values described herein, and wherein $R_{10}$ is a nitrogen linked radical of formula VI as described hereinabove.

The invention also provides a compound of formula V wherein $R_{11}-R_{14}$ have any of the values described herein, and wherein $R_{15}$ is a nitrogen linked radical of formula VI as described hereinabove.

The invention also provides a compound of formula VII wherein $R_{16}-R_{19}$ have any of the values described herein, and wherein $R_{20}$ is a nitrogen linked radical of formula VI as described hereinabove.

The invention also provides a pharmaceutical composition comprising a compound of formula I, formula II, formula V, or formula VII, or a pharmaceutically acceptable salt thereof, in combination with a pharmaceutically acceptable diluent or carrier.

Additionally, the invention provides a therapeutic method for preventing or treating a viral infection comprising administering to a mammal in need of such therapy, an effective amount of a compound of formula I, formula II, formula V, or formula VII (preferably a compound of formula I or formula II); or a pharmaceutically acceptable salt thereof.

The invention also provides a composition of matter comprising a compound of formula I, formula II, formula V, or formula VII (preferably a compound of formula I or formula II); or a pharmaceutically acceptable salt thereof and a reagent (e.g. a peptide, a saccharide, a polyclonal antibody, a monoclonal antibody) that is capable of targeting the compound to a virus.

The invention also provides a composition of matter comprising a compound of formula I, formula II, formula V, or formula VII (preferably a compound of formula V or formula VII); or a pharmaceutically acceptable salt thereof and a reagent (e.g. a peptide, a saccharide, a polyclonal antibody, a monoclonal antibody) that is capable of targeting the compound to a tumor or cancer cell.

The invention provides a compound of formula I or formula II for use in medical therapy (preferably for use as an antiviral agent or for use in treating HIV), as well as the use of a compound of formula I or formula II for the manufacture of a medicament for the treatment of a pathological condition or symptom associated with viral infection (e.g. HIV) in a mammal, such as a human.

The invention provides a compound of formula V or VII for use in medical therapy (preferably for use as an anticancer or antitumor agent), as well as the use of a compound of formula V or VII for the manufacture of a medicament for the treatment of a pathological condition or symptom associated with cancer (e.g. a cancerous tumor) in a mammal, such as a human.

The invention also provides processes and novel intermediates disclosed herein that are useful for preparing compounds of formula I, formula II, formula V, and formula VII. Some of the compounds of formula I, formula II, formula V, or formula VII are useful to prepare other compounds of formula I, formula II, formula V, or formula VII.

The invention also provides a therapeutic method comprising treating breast cancer by administering to a mammal in need for such therapy, an effective amount of a compound of formula VII or a pharmaceutically acceptable salt thereof.

BRIEF DESCRIPTION OF THE FIGURES

FIG. 2 Illustrates the synthesis of representative compounds of the invention.

FIG. 4 Illustrates starting materials useful for preparing compounds of the invention.

FIG. 8 Illustrates compounds of the invention.

DETAILED DESCRIPTION

Figure 1:
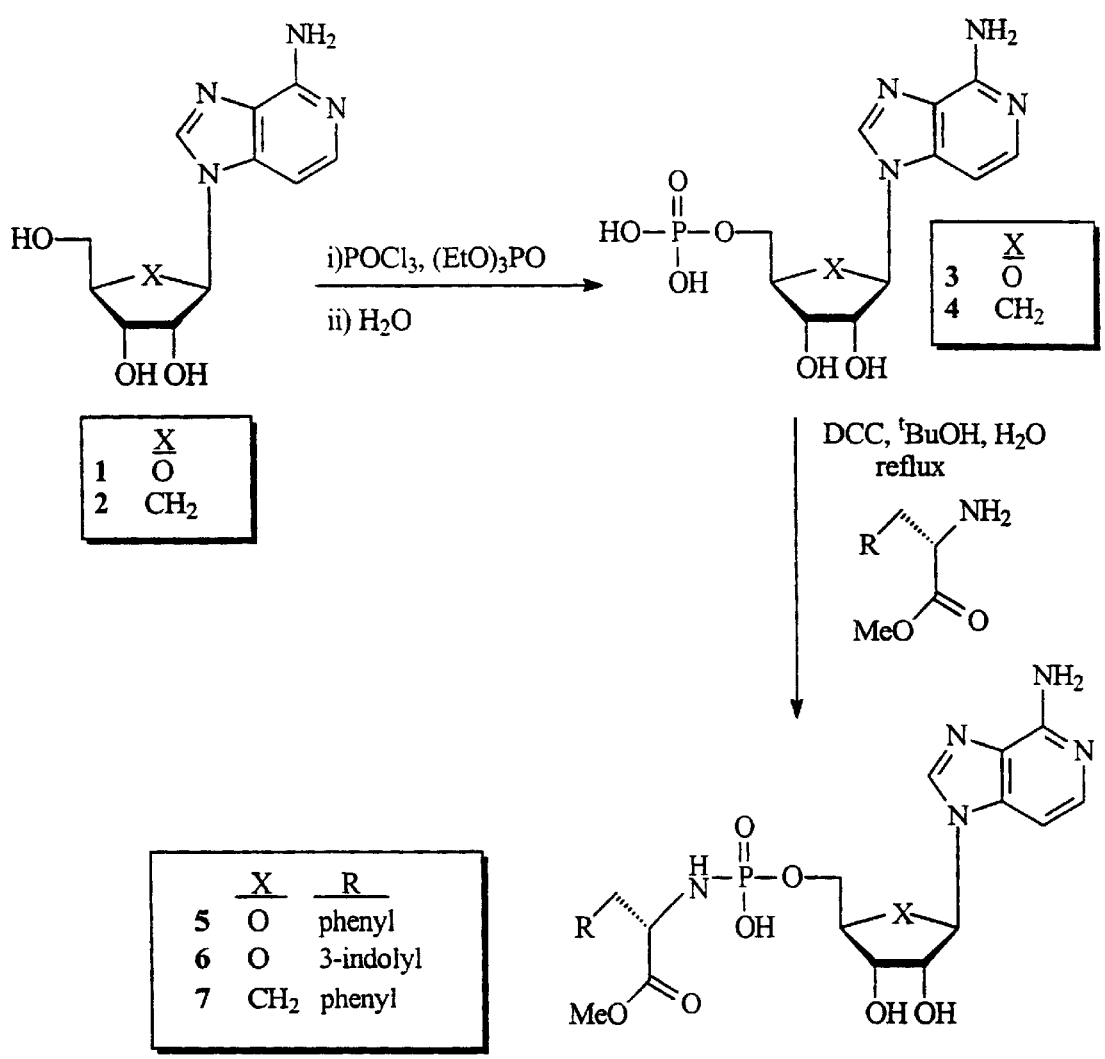
FIG. 1 Illustrates the synthesis of representative compounds of the invention.

The following definitions are used, unless otherwise described: halo is fluoro, chloro, bromo, or iodo. Alkyl, alkoxy, etc. denote both straight and branched groups; but reference to an individual radical such as "propyl" embraces only the straight chain radical, a branched chain isomer such as "isopropyl" being specifically referred to. Aryl denotes a phenyl radical or an ortho-fused bicyclic carbocyclic radical having about nine to ten ring atoms in which at least one ring is aromatic. Heteroaryl encompasses a radical attached via a ring carbon of a monocyclic aromatic ring containing five or six ring atoms consisting of carbon and one to four heteroatoms each selected from the group consisting of non-peroxide oxygen, sulfur, and N(X) wherein X is absent or is H, O, $(C_1-C_4)$alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

The term "amino acid," comprises the residues of the natural amino acids (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g. phosphoserine, phosphothreonine, phosphotyosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, -methylalanine, para-benzoylphenylalanine, phenylglycine, propargylglycine, sarcosine, and tert-butylglycine). The term also comprises natural and unnatural amino acids protected at the carboxy terminus (e.g. as a $(C_1-C_6)$alkyl, phenyl or benzyl ester or as an amide). Other suitable carboxy protecting groups are known to those skilled in the art (See for example T. W. Green, *Protecting Groups In Organic Synthesis*; Wiley: New York, 1981, and references cited therein). An amino acid can be linked to the remainder of a compound of the invention through the carboxy terminus, the amino terminus, or through any other convenient point of attachment. Preferably, when $R_5$, $R_{10}$, $R_{15}$, or $R_{20}$ is an amino acid, the amino acid is linked to phosphorous through the amino nitrogen, forming a phosphoramidate.

The term "peptide" describes a sequence of 2 to 25 amino acids (e.g. as defined hereinabove) or peptidyl residues. The sequence may be linear or cyclic. A peptide can be linked to the remainder of a compound of formula I through the carboxy terminus, the amino terminus, or through any other convenient point of attachment. Preferably a peptide comprises 2 to 25, or 5 to 20 amino acids. Peptide derivatives can be prepared using techniques that are well known in the art, for example, using solid phase peptide synthesis techniques. Preferably, when $R_5$, $R_{10}$, $R_{15}$, or $R_{20}$ is a peptide, the peptide is linked to phosphorous through the N-terminal nitrogen, forming a phosphoramidate.

The term "saccharide" includes monosaccharides, disaccharides, trisaccharides and polysaccharides. The term includes glucose, sucrose, fructose and ribose, as well as deoxy sugars such as deoxyribose and the like. A number of saccharides as well as methods for their preparation are known in the art. A saccharide can conveniently be linked to the remainder of a compound of formula I, II, V, or VII through an ether bond.

The term "viral infection" includes human immunodeficiency virus (HIV), herpes simplex virus-2 (HSV-2), varicellazoster, vaccinia, human cytomegalovirus, ebola, hepatitis B (HBV), and the like.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or steroisomeric form, or mixtures thereof, of a compound of the invention, which posses the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine antiviral activity using the standard tests described herein, or using other similar tests which are well known in the art. For example, substitutents at the 2' and 3' positions of the nucleosides of the invention can have any stereo orientation.

Specific values listed below for radicals, substituents, and ranges, are for illustration only; they do not exclude other defined values or other values within defined ranges for the radicals and substituents.

Specifically, $(C_1-C_6)$alkyl can be methyl, ethyl, propyl, isopropyl, butyl, iso-butyl, sec-butyl, pentyl, 3-pentyl, or hexyl; $(C_3-C_6)$cycloalkyl can be cyclopropyl, cyclobutyl, cyclopentyl, or cyclohexyl; $(C_3-C_6)$cycloalkyl$(C_1-C_6)$alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; $(C_1-C_6)$alkoxy can be methoxy, ethoxy, propoxy, isopropoxy, butoxy, iso-butoxy, sec-butoxy, pentoxy, 3-pentoxy, or hexyloxy; $(C_1-C_6)$alkanoyl can be acetyl, propanoyl or butanoyl; hydroxy$(C_1-C_6)$alkyl can be hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl; $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_2-C_6)$alkanoyloxy can be acetoxy, propanoyloxy, butanoyloxy, isobutanoyloxy, pentanoyloxy, or hexanoyloxy; aryl can be phenyl, indenyl, or naphthyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

A specific value for $R_6$ is adenine, guanine, cytosine, thymine, or uracil, optionally substituted by 1, 2, or 3 Y; wherein each Y is independently halo, hydroxy, $(C_1-C_6)$alkyl, $(C_3-C_6)$cycloalkyl, $(C_1-C_6)$alkoxy, $(C_3-C_6)$cycloalkyloxy, $(C_1-C_6)$alkanoyl, $(C_1-C_6)$alkanoyloxy, trifluoromethyl, hydroxy$(C_1-C_6)$alkyl, —$(CH_2)_{1-4}P(=O)(OR_k)_2$ aryl, aryl$(C_1-C_6)$alkyl, or $NR_mR_n$, and wherein any aryl ring may optionally be substituted with 1, 2, or 3 halo, hydroxy, $(C_1-C_6)$alkyl, $(C_3-C_6)$cycloalkyl, $(C_1-C_6)$alkoxy, $(C_3-C_6)$cycloalkyloxy, $(C_1-C_6)$alkanoyl, $(C_1-C_6)$alkanoyloxy, trifluoromethyl, trifluoromethyl, trifluoromethoxy, nitro, cyano, or amino.

A specific value for $R_{11}$ is adenine, guanine, cytosine, thymine, or uracil, optionally substituted by 1, 2, or 3 U; wherein each U is independently halo, hydroxy, $(C_1-C_6)$alkyl, $(C_3-C_6)$cycloalkyl, $(C_1-C_6)$alkoxy, $(C_3-C_6)$cycloalkyloxy, $(C_1-C_6)$alkanoyl, $(C_1-C_6)$alkanoyloxy, trifluoromethyl, hydroxy$(C_1-C_6)$alkyl, —$(CH_2)_{1-4}P(=O)OR(OR_w)_2$ aryl, aryl$(C_1-C_6)$alkyl, or $NR_xR_y$.

A specific value for $R_h$ is hydrogen, $(C_1-C_6)$alkyl, $(C_3-C_6)$cycloalkyl, $(C_3-C_6)$cycloalkyl$(C_1-C_6)$alkyl, $(C_1-C_6)$alkyl-S—$(C_1-C_6)$alkyl-, aryl, heteroaryl, aryl$(C_1-C_6)$alkyl, or heteroaryl$(C_1-C_6)$alkyl; wherein any aryl or heteroaryl may optionally be substituted with 1, 2, or 3 Z; $R_j$ is hydrogen, $(C_1-C_6)$alkyl, phenyl, benzyl, or phenethyl; and wherein each Z is independently halo, hydorxy, $(C_1-C_6)$alkyl, $(C_3-C_6)$cycloalkyl, $(C_1-C_6)$alkoxy, $(C_3-C_6)$cycloalkyloxy, $(C_1-C_6)$alkanoyl, $(C_1-C_6)$alkanoyloxy, trifluoromethyl, trifluoromethoxy, nitro, cyano, or amino. Preferably, the carbon bearing $R_h$ has the (S) configuration.

A specific value for $R_1$ is hydrogen or $NR_aR_b$.

A specific group of compounds of formula I are compounds wherein $R_2$ and $R_3$ are each independently hydrogen, hydroxy, azido, or $NR_cR_d$.

A specific value for $R_2$ is hydrogen.

A specific value for $R_2$ is halo, hydroxy, $(C_1-C_6)$alkanoyl, trifluoromethyl, azido, cyano, or $NR_cR_d$.

A specific value for $R_2$ is azido.

A specific value for $R_2$ is $NR_cR_d$.

A specific value for $R_3$ is hydrogen.

A specific value for $R_3$ is halo, hydroxy, $(C_1-C_6)$alkanoyl, trifluoromethyl, azido, cyano, or $NR_cR_d$.

A specific value for $R_3$ is azido.

A specific value for $R_3$ is $NR_cR_d$.

A specific value for $R_4$ is hydrogen.

A specific value for $R_5$ is an amino acid.

A specific value for X is oxy.

A specific value for X is thio.

A specific value for X is methylene.

A specific group of compounds are compounds wherein $R_a$ and $R_b$ are each hydrogen.

A specific group of compounds are compounds wherein $R_c$ and $R_d$ are each hydrogen.

A specific group of compounds are compounds wherein $R_2$ is $NR_cR_d$; $R_3$ is hydrogen; $R_c$ is —$C(=O)N(R_e)(R_f)$; and $R_d$ is hydrogen.

A specific group of compounds are compounds wherein $R_2$ is hydrogen; $R_3$ is $NR_cR_d$; $R_c$ is —$C(=O)N(R_e)(R_f)$; and $R_d$ is hydrogen.

A specific group of compounds are compounds wherein $R_2$ is $NR_cR_d$; $R_3$ is hydrogen; and Rc is —$C(=O)OR_g$.

A specific group of compounds are compounds wherein $R_3$ is $NR_cR_d$; $R_2$ is hydrogen; and $R_c$ is —$C(=O)OR_g$.

A specific value for $R_h$ is hydrogen, $(C_1-C_6)$alkyl, aryl, heteroaryl, aryl$(C_1-C_6)$alkyl, or heteroaryl$(C_1-C_6)$alkyl; wherein any aryl or heteroaryl may optionally be substituted with 1, 2, or 3 Z.

A specific value for $R_h$ is hydrogen, $(C_1-C_6)$alkyl, phenylmethyl, or 3-indolylmethyl.

A specific value for $R_h$ is phenylmethyl.

A specific value for $R_h$ is 3-indolylmethyl.

A specific value for $R_j$ is $(C_1-C_6)$alkyl.

A specific value for $R_j$ is methyl, ethyl propyl, or isopropyl.

A specific group of compounds are compounds wherein the carbon bearing $R_h$ has the (S) absolute configuration.

A specific group of compounds are compounds wherein the carbon bearing $R_h$ has the (R) absolute configuration.

A specific value for $R_{ah}$ is hydrogen, $(C_1-C_6)$alkyl, aryl, heteroaryl, aryl$(C_1-C_6)$alkyl, or heteroaryl$(C_1-C_6)$alkyl; wherein any aryl or heteroaryl may optionally be substituted with 1, 2, or 3 Z.

A specific value for $R_{ah}$ is hydrogen, $(C_1-C_6)$alkyl, phenylmethyl, or 3-indolylmethyl.

A specific value for $R_{ah}$ is phenylmethyl.

A specific value for $R_{ah}$ is 3-indolylmethyl.

A specific value for $R_{ai}$ and $R_{aj}$ are each independently hydrogen, $(C_1-C_6)$alkyl, or $(C_3-C_6)$cycloalkyl.

A specific value for $R_{ai}$ is hydrogen and $R_{aj}$ is methyl, cyclopropyl, or cyclohexyl.

A specific group of compounds are compounds wherein the carbon bearing $R_{ah}$ has the (S) absolute configuration.

A specific group of compounds are compounds wherein the carbon bearing $R_{ah}$ has the (R) absolute configuration.

A specific compound of formula I is the compound 3-deaza adenosine-5-N-(1-carbomethoxy-2-phenylethyl)phosphoramidate; 3-deaza adenosine-5-N-(1-carbomethoxy-2indolyethyl)phosphoramidate; 3-deaza aristeromycin-5-N-(1-carbomethoxy-2phenylethyl)phosphoramidate; 3-deaza adenosine-5-N-(1-methylaminocarbonyl-2phenylethyl)phosphoramidate; or 3-deaza adenosin-5-N-{1methylamino-carbonyl-2-(3-indolyl)ethyl}-phosphoramidate; or a pharmaceutically acceptable salt thereof.

A specific value for $R_6$ is a nitrogen linked radical of formula IV:

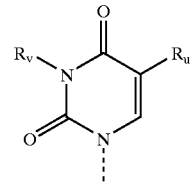

IV wherein $R_u$ is hydrogen, halo, $(C_1-C_6)$alkyl, $(C_3-C_6)$cycloalkyl, or trifluoromethyl; and $R_v$ is hydrogen, $(C_1-C_6)$alkyl, $(C_3-C_6)$cycloalkyl, trifluoromethyl, hydroxy$(C_1-C_6)$alkyl, or -$(CH_2)_{1-4}P(=O)(OR_k)_2$.

A specific group of compounds are compounds wherein one of $R_7$ and $R_8$ is -$N(R_o)C(=O)N(R_p)(R_q)$.

A specific value for $R_7$ is —$N(R_o)C(=O)N(R_p)(R_q)$.

A specific value for $R_8$ is —$N(R_o)C(=O)N(R_p)(R_q)$.

A specific value for R$_{10}$ is an amino acid.
A specific value for R$_{10}$ is a peptide.
A specific value for R$_{11}$ is a nitrogen linked radical of formula VI:

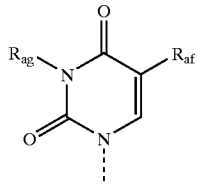

VI wherein R$_{af}$ is hydrogen, halo, (C$_1$–C$_6$)alkyl, (C$_3$–C$_6$) cycloalkyl, or trifluoromethyl; and R$_{ag}$ is hydrogen, (C$_1$–C$_6$) alkyl, (C$_3$–C$_6$)cycloalkyl, trifluoromethyl, hydroxy(C$_1$–C$_6$) alkyl, or —(CH$_2$)$_{1-4}$P(=O)(OR$_w$)$_2$.

A specific value for R$_{12}$ is azido.
A specific value for R$_{13}$ is azido.
A specific value for R$_{15}$ is an amino acid.
A specific value for R$_{15}$ is a peptide.
A specific group of compounds are compounds wherein R$_{11}$ is thymine; R$_{12}$ hydrogen; R$_{13}$ is azido; R$_{14}$ is hydrogen; R$_{15}$ is N-linked phyenlalanine; and W is oxy; or a pharmaceutically acceptable salt thereof.

A specific value for R$_{16}$ is a nitrogen linked radical of formula VI:

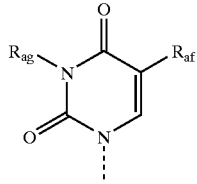

VI wherein R$_{af}$ is fluoro; and R$_{ag}$ is hydrogen.
A specific value for R$_{17}$ is hydroxy.
A specific value for R$_{18}$ is hydroxy.
A specific value for R$_{20}$ is an amino acid.
A specific value for R$_{20}$ is an L-amino acid.
A specific value for R$_{20}$ is a peptide.
A specific compound is a compound of formula VII wherein R$_{16}$ is 5-fluorouracil; R$_{17}$ is hydrogen; R$_{18}$ is hydroxy; R$_{19}$ is hydrogen; R$_{20}$ N-linked L-phenylalanine; and W is oxy; or a pharmaceutically acceptable salt thereof.

A specific compound is a compound of formula VII wherein R$_{16}$ 5-fluorouracil; R$_{17}$ is hydrogen; R$_{18}$ is hydroxy; R$_{19}$ is hydrogen; R$_{20}$ is N-linked L-tryptophan; and W is oxy; or a pharmaceutically acceptable salt thereof.

A specific compound is the compound 3'-Azido-3'-deoxythymidine—
5'-methylaminoglycinylphosphoramidate;
3'-Azido-3'-deoxythymidine-5'-methylamino-L-alaninylphosphoramidate;
3'-Azido-3'-deoxythymidine-5'-methylamino-L-valinylphosphoramidate;
3'-Azido-3'-deoxythymidine-5'-methylamino-L-leucinyl-phosphoramidate;
3'-Azido-3'-deoxythymidine-5'-methylamino-L-phenylalninyl-phosphoramidate;
3'-Azido-3'-deoxythymidine-5'-methylamino-D-phenylalaninyl-phosphoramidate;
3'-Azido-3'-deoxythymidine-5'-methylamino-L-tyrosinylphosphoramidate;
3'-Azido-3'-deoxythymidine-5'-methylamino-L-tryptophanyl-phosphoramidate;
3'-Azido-3'-deoxythymidine-5'-methylamino-D-tryptophanyl-phosphoramidate;
3'-Azido-3'-deoxythymidine-5'-ethylamino-L-tryptophanyl-phosphoramidate;
3'-Azido-3'-deoxythymidine-5'-isopropylamino-L-tryptophanyl-phosphoramidate;
3'-Azido-3'-deoxythymidine-5'-cyclopropylamino-L-tryptophanyl-phosphoramidate;
or 3'-Azido-3'-deoxythymidine-5'-cyclohexylamino-L-tryptophanyl-phosphoramidate; or a pharmaceutically acceptable salt thereof.

Processes for preparing compounds of formula I, II, V, and VII are provided as further embodiments of the invention and are illustrated by the following procedures in which the meanings of the generic radicals are as given above unless otherwise qualified.

Figure 9:
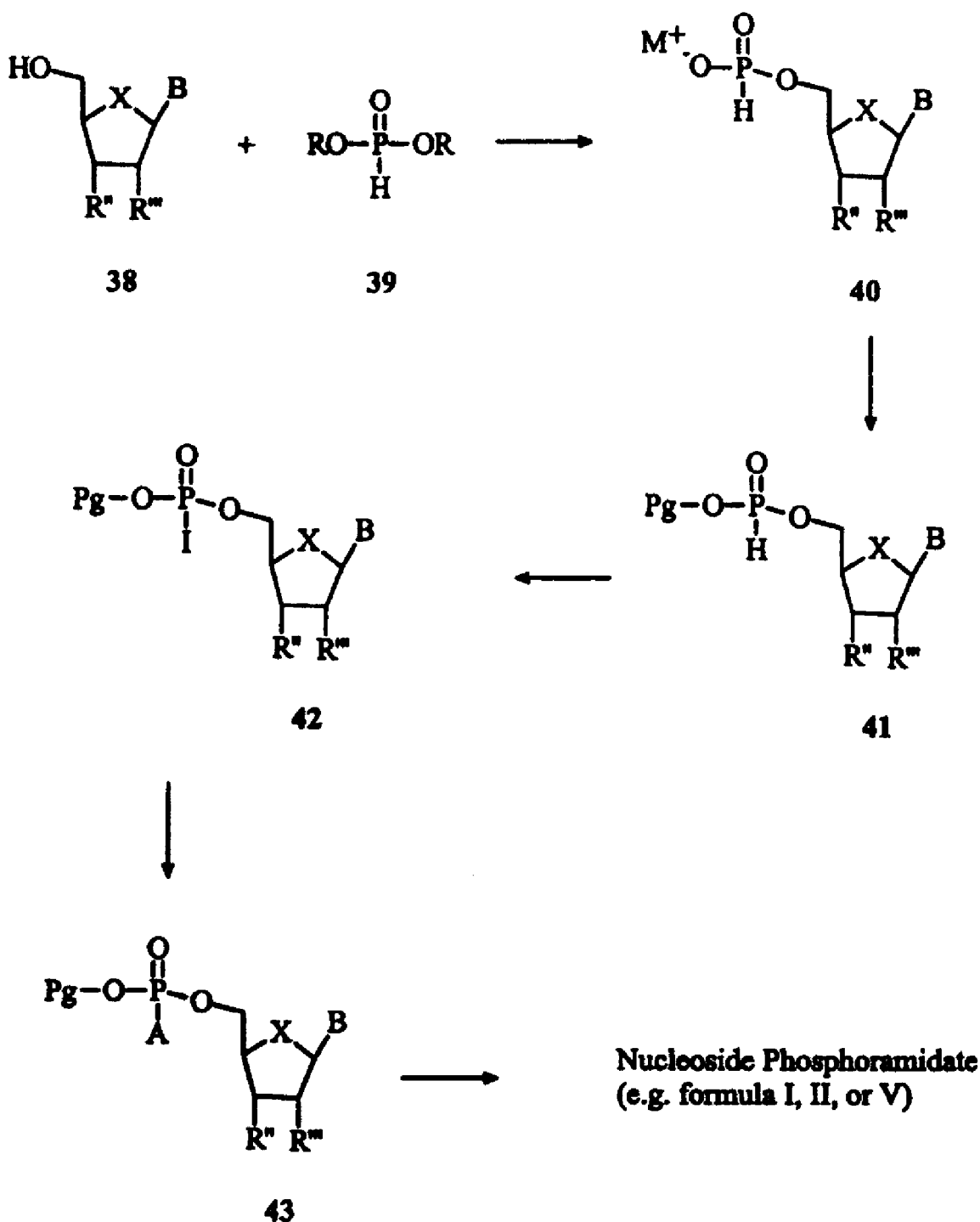
FIG. 9 Illustrates the preparation of compounds of the invention.

As illustrated in FIG. 9, a compound of formula I, II, V, and VII can be prepared from a corresponding compound of formula 43 by removal of the hydroxy protecting group "pg" (e.g. a silyl protecting group such as a trimethylsilyl group). For example, the reaction can be carried out by aqueous hydrolysis as described in Example 1.

A compound of formula I, II, V, or VII wherein R$_5$, R$_{10}$, R$_{15}$ or R$_{20}$ is an amino acid or a peptide wherein the carboxy terminus is protected as an amide (e.g. an alkyl or benzyl amide) can be prepared from a corresponding compound wherein R$_5$, R$_{10}$, R$_{15}$, or R$_{20}$ is amino acid or a peptide wherein the carboxy terminus is protected as an ester, by reaction with the requsite amine under suitable conditions. The reaction can conveniently be carried out under conditions similar to those described in Example 4.

The preparation of amino acid phosphoramidates of 3-deaza adenosine (1, DZA) and 3-deaza aristeromycin (2, DZAri) is shown in FIG. 1. Direct phosphorylation of DZA and DZAri was accomplished using phosphorus oxychloride in triethylphosphate, yielding the monophosphates 3 and 4 in 81% and 67%, respectively (Yoshikawa et al., *Tetrahedron Lett.*, 50:5065–5068 (1967); Yoshikawa et al., *Bull. Chem. Soc. Jpn.*, 42:3505–3508 (1969). Construction of the phosphoramidates was based on a procedure by Moffatt and Khorana, in which they describe the dicyclohexylcarbodiimide (DCC)-mediated coupling of adenosine 5-monophosphate to p-anisidine (Moffatt et al., *J. Am. Chem. Soc.*, 83:649–658 (1961)). The monophosphates (3 and 4) were then coupled with DCC in refluxing tert-BuOH/H$_2$O to the carbomethoxy esters of L-phenylalamine and L-tryptophan.

The crude product mixtures were purified by reverse phase HPLC on a C8 semi-prep column, to give 5–7 in a yield of 8–30%.

Compounds of the invention can conveniently be prepared using a combination of solution and solid phase synthesis. As shown in FIG. 2 representative compounds of Formula II can be prepared using a Multipin™ modular synthesis format with a SynPhase crown carboxypolystyrene resin, which is commercially available from Chiron Technologies, Inc.

The alcohol (8) can be coupled to the pin by treatment with DIPCDI and a catalytic amount of DMAP. The attached nucleosides can be deprotonated with either sodium hydride or potassium carbonate followed by the addition of the appropriate electrophile. Next, the azido group can be reduced in the presence of dithiothreitol, followed by treatment with the appropriate substituted isocyanate. After separation from the reaction solution, the nucleoside can be liberated from the resin by treatment with ammonia. Following evaporation, the nucleosides can be resuspended in an appropriate buffer for biological testing. In addition, gram quantities of the compounds of the invention can be obtained by a similar protocol employing batch quantities of the resin.

Figure 3:
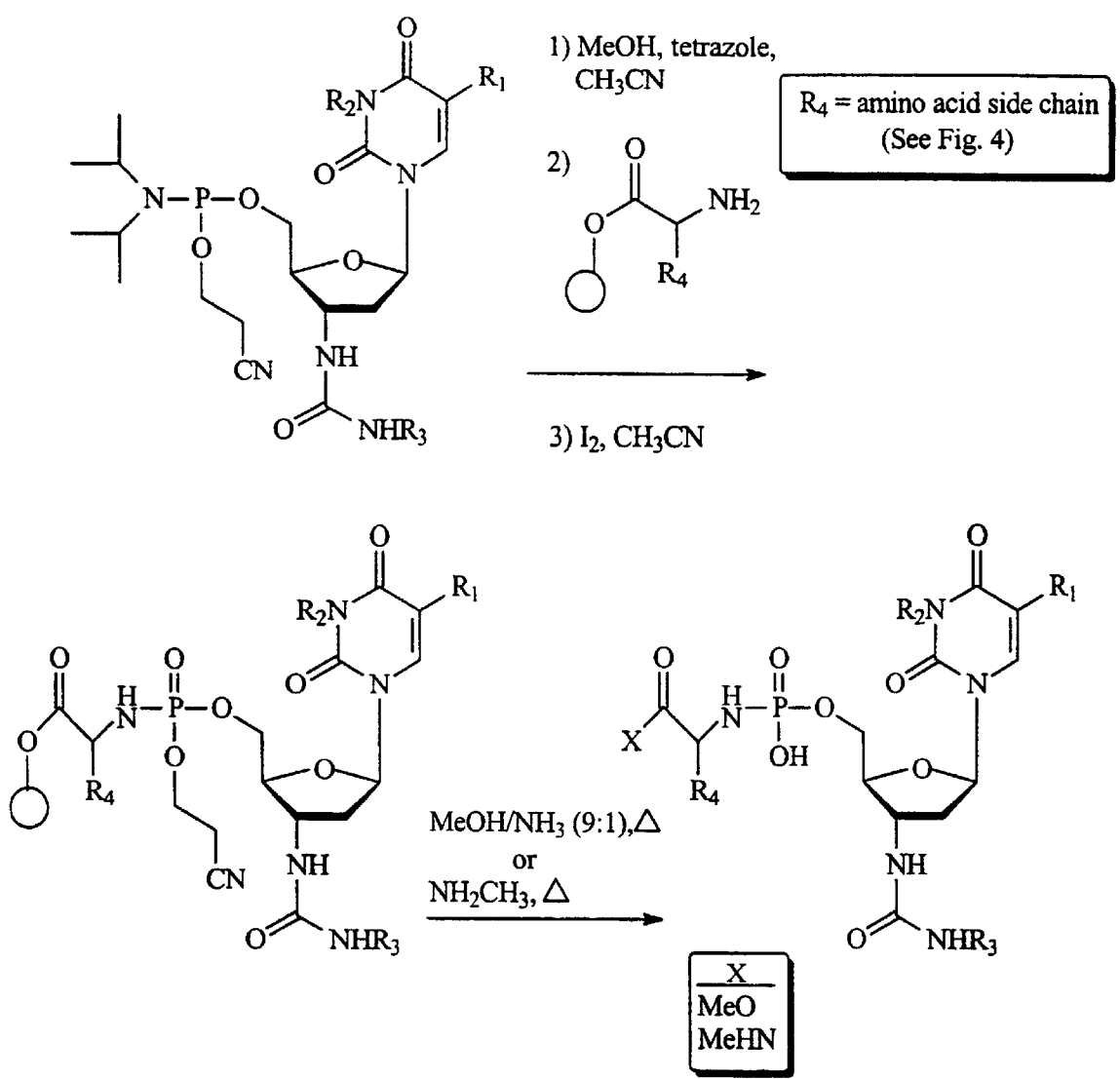
FIG. 3 Illustrates the synthesis of representative compounds of the invention.

Other compounds of the invention can be prepared as illustrated in FIG. 3. Using the same Multipin™ modular synthesis format described above, resin pins can be acylated with one of 24 commercially available (Aldrich Chemical Co. and CHEM-IMPEX INTERNATIONAL, Inc.) natural or unnatural BOC protected amino acids (shown in FIG. 4). Following deprotection with trifluoro acetic acid (TFA), the amino acid resin can be treated with a separately prepared phosphoramidite, which has been activated with tetrazole and methanol. Nucleosides that contain a free hydroxyl group at the 5-position can be prepared as the acetylated derivatives before conversion to phosphoramidites. The bound phosphite products can be treated with iodine to afford the corresponding phosphoramidates. After separation from the reaction mixture, the cyano ethyl protecting group can be removed and the phosphoramidates cleaved from the resin in a methanol/ammonia (9:1) solution to yield the corresponding methyl esters or an excess of methyl amine to yield the corresponding methyl amides. Acetylated nucleosides can also be deprotected during this step. Following evaporation en vacuo, the nucleoside phosphoramidates can be resuspended in an appropriate buffer for biological testing. If desired, gram quantities can be prepared by a similar synthetic procedure with batch quantities of the resin or by solution phase chemistry.

Compounds of formula V can be prepared using procedures similar to those described herein for the preparation of compounds of formula I or II, or can be prepared using procedures similar to those described in T. W. Abraham et al. *J. Med Chem.* 1996, 39, 4569–4575.

The invention also provides a general method for preparing nucleoside phosphoramidates (e.g. compounds of formula I, II, V, and VII as well as others). As illustrated in FIG. 9, reaction of a nucleoside of formula 38, wherein B is any suitable nucleoside base and R" and R"' are each independently hydrogen, halo, hydroxy, $(C_1-C_6)$alkyl, $(C_3-C_6)$cycloalkyl, $(C_1-C_6)$alkoxy, $(C_3-C_6)$cycloalkyloxy, $(C_1-C_6)$alkanoyl, $(C_1-C_6)$alkanoyloxy, trifluoromethyl, azido, cyano, or $NR_cR_d$, with a phosphite of formula 39, wherein each R is independently a suitable radical (e.g. $(C_1-C_6)$ alkyl, aryl, benzyl, or phenethyl, and preferably wherein each R is phenyl), yields an H-phosphate salt of formula 40 wherein ($m^+$) is a suitable counterion (e.g. triethylammonium); protection of the oxygen in compound 40 with a suitable protecting group "Pg" (e.g. a silyl protecting group such as trimethylsilyl or tert-butyldimethylsilyl) gives a compound of formula 41; treatment with iodine gives a highly reactive compound of formula 42, which can conveniently be reacted directly with an amino acid or peptide to give the nucleoside phosphoramidate (e.g. a compound of formula I, II, V, or VII).

Suitable protecting groups "Pg" are known in the art, for example see T. W. Greene, *Protecting Groups In Organic Synthesis;* Wiley: New York, 1981, and references cited therein. It may also be convenient to protect other functionalities in the intermediate compounds formula 38–43 with suitable protecting groups that can be removed at a convenient point in the synthetic scheme.

The invention also provides a process for preparing a compound of formula I wherein $R_4$ is hydrogen, comprising deprotecting a corresponding compound of formula 44:

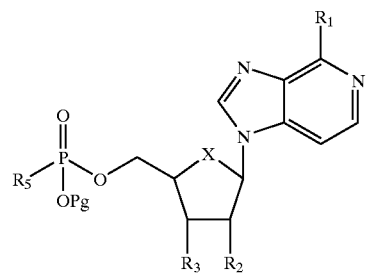

wherein Pg is a suitable removable protecting group.

The invention also provides a process for protecting a compound of formula II wherein $R_9$ is hydrogen comprising deprotecting a corresponding compound of formula 45:

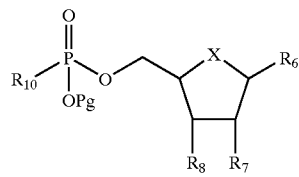

wherein Pg is a suitable removable protecting group.

The invention also provides a process for preparing a compound of formula V, wherein $R_{14}$ is hydrogen, comprising deprotecting a corresponding compound of formula 46:

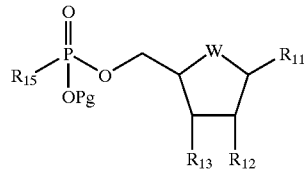

wherein Pg is a suitable removable protecting group.

The invention also provides a process for preparing a compound of formula VII, wherein $R_{19}$ is hydrogen, comprising deprotecting a corresponding compound of formula 47:

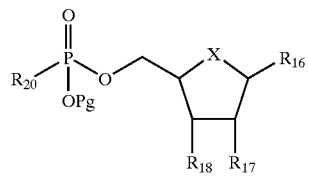

wherein Pg is a suitable removable protecting group.

The invention also provides novel intermediates of formula 40, 41, 42, and 43 that are useful to prepare nucleoside phosphoramidated (e.g. to compounds of formula I, II, V, or VII. Preferably, the radicals B, R", R"', and A have any of the values, specific values or preferred values defined herein for a corresponding radical in a nucleoside of formula I, II, V, or VII.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, -ketoglutarate, and -glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

A compound of the invention may be targeted to a particular virus by attaching the compound to a reagent which is capable of binding to the virus (e.g. a virally encoded polypeptide). Suitable reagents include saccharides, peptides, polyclonal antibodies, and monoclonal antibodies. The compound-reagent complex or conjugate may further comprise a linker that attaches the compound to the reagent. The linker can be, for example, an alkyl or ester based linker group. Examples of suitable linkers include $-(CH_2)_{0-6}-O-(CH_2)_{0-6}-$, $-(CH_2)_{1-12}-$, $-OC(=O)(CH_2)_{1-12}-$, $-OC(=O)(CH_2)_{1-12}-$, and $-OC(=O)CH_2)_{1-10}C(=O)O-$. As would be apparent to one skilled in the art, the nature of the linker is not critical, provided the linker is suitably stable for the intended use. Thus, other linkers of approximately the same length (e.g. about 2–100 or about 5–50) can also be used. A reagent can conveniently be linked to a compound of the invention, for example, by replacing $R_1$–$R_{15}$, $R_h$, $R_j$, $R_u$, or $R_v$, with a bond to the desired reagent or to the linker.

Similarly, a compound of the invention may be targeted to a particular tumor or cancer cell by attaching the compound to a reagent which is capable of binding to the tumor or cancer cell. Suitable reagents include saccharides, peptides, polyclonal antibodies, and monoclonal antibodies. The compound-reagent complex or conjugate may further comprise a linker (e.g. a linker as described above) that attaches the compound to the reagent.

The compounds of the invention can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimible edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustainied-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage from must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monosterate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acids salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known in the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,939,949.

Generally, the concentration of the compound(s) of formula I in a liquid composition, such as a lotion, will be from about 0.1–25 wt-%, preferably from about 0.5–10 wt-%. The concentration in a semi-solid or solid composition such as a gel or a powder will be about 0.1–5 wt-%, preferably about 0.5–2.5 wt-%.

The amount of the compound, or an active salt or derivative thereof, required for use in treatment will vary not only with the particular salt selected but also with the route of administration, the nature of the condition being treated and the age and condition of the patient and will be ultimately the discretion of the attendant physician of clinician.

In general, however, a suitable dose will be in the range of from about 0.5 to about 100 mg/kg, e.g., from about 10 to about 75 mg/kg of body weight per day, such as 3 to about 50 mg per kilogram body weight of the recepient per day, preferably in the range of 6 to 90 mg/kg/day, most preferably in the range of 15 to 60 mg/kg/day.

The compound is conveniently administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 $\mu$M, preferably, about 1 to 50 $\mu$M, most preferably, about 2 to about 30 $\mu$M. This may be achieved, for example, by the intravenous injection of a 0.05 to 5% solution of the active ingredient, optionally in saline, or orally administered as a bolus containing about 1–100 mg of the active ingredient. Desirable blood levels may be maintained by continuous infusion to provide about 0.01–5.0 mg/kg/hr or by intermittent infusions containing about 0.4–15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops in to the eye.

Generally the phosphoramidate compounds of the invention are less toxic and have greater anti-cancer or anti-viral activity than the corresponding parent nucleosides. Additionally, phosphoramidates of the invention may be more soluable, more stable, have greater half-lives in vivo, or have better tissue distribution than the corresponding parent nucleosides. For example, representative phosphoramidate monoesters of AZT have been found to have at least five times the half-life and at least 10 times the tissue distribution of AZT.

The ability of a compound of the invention to act as an antiviral agent may be determined using pharmacological models which are well known to the art, or using Test A or B described below.

Test A.

The antiviral activity of representative compounds of the invention was determined with matched HIV-1 isolates and a laboratory HIV-1 strain as previously described (D. L. Mayers et al., *Proc. Natl. Acad. Sci., USA* 1995, 92, 215–219; and C. R. Wagner et al., *Bioorganic and Medicinal Chemistry Letters*, 1995, 5, 1819–1824). As can be seen in Table 1, the phosphoramidiates, 5, 6 and 7 (FIG. 1), were able to effectively inhibit HIV-1 viral growth in peripheral blood lymphocytes. The tryptophan phosphoramidate, 6, is nearly forty-fold more active than DZA, while the phenylalanine derivative, 5, is nearly ten-fold more active than DZA. As was observed for AZT-phosphoramidates, the DZA phosphoramidates exhibited no detectable cytotoxicity to PBMCs at concentrations as high as 10 $\mu$M, while the $CC_{80}$ for DZA is 1 $\mu$M. Surprisingly, unlike DZA, phosphoramidates of DZA did not exhibit activity against AZT resistant HIV-1. Consequently, the mechanism of action of 5 and 6, probably involves direct inhibition of HIV-1 reverse transcriptase and not modulation of cellular transcription factors, as has been observed for the nucleotide. In addition, preliminary experiments have demonstrated that 7 has comparable antiviral activity to DZAri.

TABLE 1

| HIV-1 isolate | Mean $IC_{50}$ (nM) in PBLs | | | | | |
|---|---|---|---|---|---|---|
| | AZT | DZA | DZAri | 5 | 6 | 7 |
| A012 pre-AZT | 1.2 | 144 | 141 | 9.3 | 4.4 | n.d. |
| A012 post-AZT | >1000 | 165 | 365 | >10,000 | >10,000 | n.d. |
| LAI | 4.0 | n.d. | n.d. | n.d. | n.d. | 400 |
| G910 AZTr | 700 | n.d. | n.d. | n.d. | n.d. | 10,000 |

All values are the average of three separate experiments. Variance was 10% or less for the reported averages.

Test B.

The antiviral properties of compounds of the invention can also be determined in PBMCs using a procedure similar to that described by E. I. McIntee, et al. *J. Med. Chem.*, 1997, 40, 3323–3331. Antiviral data for representative compounds of the invention is shown in Table 2.

TABLE 2

Antiviral Activity of representative compounds of the invention in PBMC's

[Structure: phosphoramidate with R, R', N, P(=O)(OH)-O-CH2-furanose ring with N3 and thymine-like base with CH3]

| Compound | IC$_{50}$ (μm) PBMC's Donor 1 | IC$_{50}$ (μm) PBMC's Donor 2 |
|---|---|---|
| 9  | 0.300 | 0.350 |
| 10 | 1.0   | 1.0   |
| 11 | 30    | 15    |
| 12 | 0.050 | 0.085 |
| 27 | 0.180 | 0.250 |
| 28 | 0.900 | 0.100 |
| 30 | 0.7   | 1.8   |
| 31 | 0.400 | 0.18  |
| AZT| 0.003 | 0.010 |

The results from Test A and Test B demonstrate that representative compounds of the invention possess antiviral properties. In Test B, it was unexpectedly, found that certain phosphoramidates comprising D-amino acids demonstrated equal or sometimes greater antiviral activity than the corresponding phosphoramidate comprising the corresponding L-amino acid (e.g. compare compounds 12 and 11, and compounds 31 and 30). This is contrary to previous reports that have suggested that nucleosides comprising D-amino acids have diminished antiviral activity compared to corresponding nucleosides comprising the corresponding L-amino acid.

The data from Tests A and B demonstrates that compounds of the invention are useful as antiviral agents. Compounds of the invention are specifically useful for treating viral infections. Additionally, compounds of the invention may be useful as pharmacological tools for the further investigation of the mechanism of action of antiviral nucleosides and analogs thereof.

Compounds of formula I and II, as well as compounds of formula V wherein $R_{15}$ is an amino acid in the D form (e.g. compounds 12 and 31) are particularly useful as antiviral agents.

The ability of a compound of the invention to act as an anticancer agent may be determined using pharmacological models which are well known to the art, or using Test C, D, E, F, or G described below.

Text C.

Figure 5:
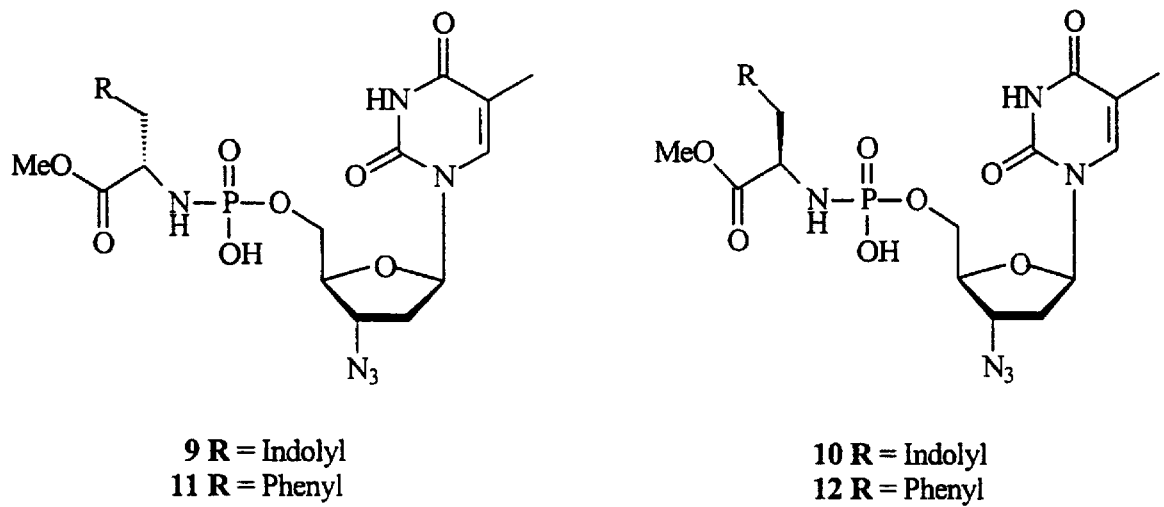
FIG. 5 Illustrates representative compounds of formula V.

Before testing there biological activity of the phosphoramidate monoesters, 9–12 (FIG. 5), the stability of these compounds in culture media and human serum was determined. The rates of decomposition of the phosphoramidates in serum was determined by incubating each compound at a concentration of 100 mM in 20% fetal calf or 20% human serum, pH 7.2 at 37° C. followed by analysis of the remaining phosphoramidates by reverse-phase HPLC at 14 hrs, 24 hrs, 40 hrs, and 60 hrs.

The rate of decomposition for the four phosphoramidates was shown to be negligible over two and a half days, $10^{-10}$ mol/hr in fetal calf and human serum. Typically, >99% of the added phosoramidate remained intact after incubation in culture media or human serum for two and a half days. Consequently, unlike 5-phosphorylated nucleosides, the phosphoramidates are not rapidly degraded by an endogenous blood phosphohydrolases or phosphorylases.

Analysis of the pH dependence of the stability of compound 9 revealed that appreciable hydrolysis was only observable at pH values of 2.0 for example, the t½ at pH 2.0 for 9 in phosphate buffer was found to be 1.5 hrs.

Compounds 9–12 were tested for cytotoxicity and compared to AZT (CC$_{50}$=10±5 nM) (Table 2). Both the L-tryptophan and L-phenylalanine phosphoramidates were shown to be considerably less toxic to leukemia and peripheral blood mononuclear cells (PBMC's), but reasonably toxic toward breast cancer cells. The tryptophan derivative 9 was shown to be three-fold less toxic than AZT (CC$_{50}$=30±10 nM) in MCF7 cells, while the phenylalanine phosphoramidate 11 was 40-fold less toxic (IC$_{50}$=400±50 nM). When compared to phosphoramidates containing D-phenylalanine and D-tryptophan, the activity of the L-tryptophan derivative 9 was shown to be >3000-fold more toxic than the D-tryptophan derivative 10 and at least 100-fold more toxic than the D-phenylalanine derivative 12. In addition, cells incubated with 9 and 12 were shown to contain substantial amounts of the intact phosphoramidates and phosphorylated AZT. Although approximately 13-fold less intracellular phosphorylated AZT was observed for cells treated with either 9 or 12 than for cells treated with AZT. Thus, the activity of the phosphoramidates appears to depend on the chemical structure of the amino acid side chain and at least partially on the amount of conversion to intracellular phosphorylated AZT. Both 9 and 11 are one of two orders of magnitude more soluble in water than AZT, as demonstrated by the Log P values, implying that increased lipophilicity is not necessary for biological activity (Table 3).

TABLE 3

Cytotoxicity of Phosphoramidates of AZT and Quantitation of the Amount of Intracellular AZT, Total Phosphorylated AZT and Parent Phosphoramidate

| | | (ng/million cells)[a] | | | |
|---|---|---|---|---|---|
| Compound | CC$_{50}$ (nm) MCF-7 cells | Total Phosphorylated AZT | Phosphoramidate | AZT | Log P |
| AZT | 10   | 710  | —    | 127.4 | 0.1244 |
| 9   | 30   | 53   | 57   | 0.744 | −1.03  7 |
| 10  | >100 | n.d. | n.d. | n.d.  | n.d. |
| 11  | 400  | 59   | 79   | 8.3   | −2.4209 |
| 12  | >100 | n.d. | n.d. | n.d.  | n.d. |

[a]Cells were incubated with 100 mM compound for 17 hr and the intracellular amounts determined by RPHPLC-RIA.

Test D.

The in vivo anti-breast tumor activity of AZT and compound 9 against rat mammary carcinomas, was evaluated as follows. Fifty-day old female Sprague-Dawley rats with an average weight of 170 g we given 50 mg/kg of methyl nitroso urea in 1 mL of water by i.p. injections over a period of one week. One hundred percent of the rats developed mammary tumors between 2 to 3 months after treatment. Once a week, the rats were lightly anesthesized with ether and the tumors were measured in 2 dimensions with a caliper. The tumor volume was calculated based on an ellipsoid tumor shape with the following equation: $v=4/3 P r_1 2r_2$, where $r^1$ is the minor radius. The rats were selected after at least one tumor pet rat had reached 1 cm in a single dimension. The rats were divided into control and experimental groups. Each experimental rat was matched with a control rat with similar sized tumors and the overall number of tumors at the beginning of the experiment was approximately the same for both groups. The animals were divided into 4 treatment groups with 5 animals in each group, and injected i.p. daily for the duration of the experiment. Tumor size and weight was determined weekly.

Figure 6:
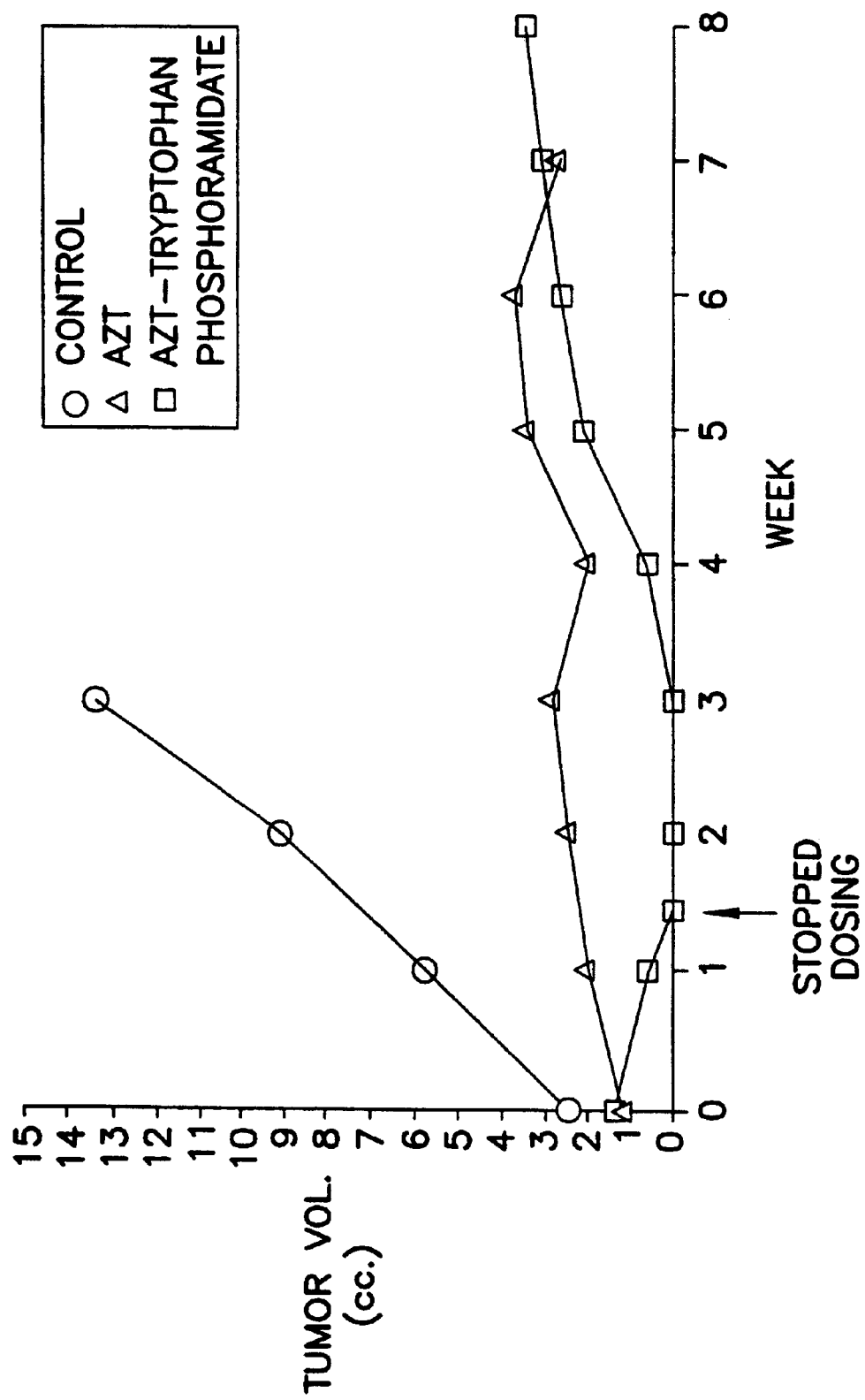
FIG. 6 shows the effect of AZT and representative compounds of the invention on rat mammary tumor growth.
Figure 7:
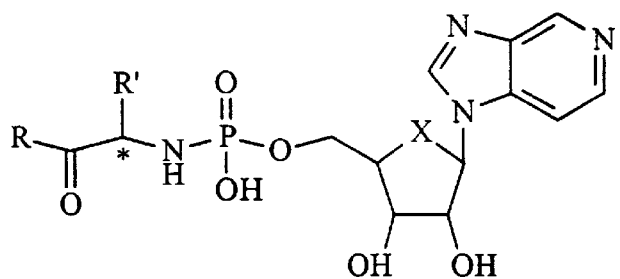
FIG. 7 Illustrates compounds of the invention.

Tumor volumes of control and treated rats were measured and plotted on a growth curve (FIG. 6). For the control animals, the tumor size approximately doubled in volume every seven days. No further measurements could be taken from the control group after three weeks, since it became necessary to euthanize the animals because of tumor ulceration. All animals in the treatment groups gained weight throughout the experiment and exhibited no obvious behavioral or physical symptoms of toxicity.

AZT was able to reduce the rate of tumor growth by nearly 80%, whereas 9 was able to not only reduce the rate of tumor growth but cause complete tumor registration in ten days. These results demonstrate that a phosphoramidate of a nucleoside can significantly reduce the rate of mammary tumor growth and tumor size in vivor.

Test E.

Representative compounds of the invention were evaluated for growth inhibitory activity in MCF-7 cells in culture. The cells were maintained in RPMI 1640 medium supplemented with 20% heat-inactivated fetal bovine serum, penicillin (100 U/mL), and streptomycin (100 mg/mL). Typically, 24-well and 6-well plates were used to culture 25,000–100,000 and 200,000–500,000 cells, respectively. Various concentrations of the compounds were added and the cells cultured with and without compound at 37 C. in 10% $CO_2$-90% air environment for 48 hours, at which time portions were counted for cell proliferation and viability by the tryptan-blue day exclusion method. Results are shown in Table 4.

TABLE 4

Anti-Breast Cancer Activity of Representative Compounds of The Invention

| Compound | $CC_{50}$ ($\mu$m) MCF-7 |
| --- | --- |
| 9 | 0.030 |
| 10 | >100 |
| 11 | 0.400 |
| 12 | >100 |
| 17 | >100 |
| 19 | 6.0 |
| 20 | 7.5 |
| 21 | >100 |
| 27 | 1.5 |
| 28 | >100 |
| 30 | 0.025 |
| 31 | >100 |
| 35 | 7.5 |
| AZT | 0.008 |

Test F.

The stability of representative compounds of formula VII was compared to the stability of known compounds 5-fluorouracil (FU) and 5-fluorodeoxyuridine (FUdR) using a procedure similar to that described by T. W. Abraham, et al. *J. Med. Chem.*, 1996, 39, 4569–4575. The results are shown in Table 5.

TABLE 5

Stability in Cell Media and Human Plasma

| Compound | Half-life (hours) Cell Media 37 C | Half-life Human Plasma 37 C |
| --- | --- | --- |
| 36 | >48 | >120 |
| 37 | >48 | >120 |
| FUdR | >48 | 5–10 minutes |

Test G.

The activity of representative compounds of formula VII against MCF-7 breast cancer cells and CEM T-cell leukemia cells were determined using a procedure similar to that described by C. R. Wagner, et al. *Cancer Research*, 1997, 57, 2341–2345. The results are shown in Table 6.

TABLE 6

Activity of Representative Compounds of Formula VII Against MCF-7 Breast Cancer Cells and CEM T-cell Leukemia Cells.

| Compound | $CC_{50}$ ($\mu$M) MCF-7 | $CC_{50}$ ($\mu$M) CEM |
| --- | --- | --- |
| 36 | 0.045 | 0.32 |
| 37 | 0.025 | 0.32 |
| 38 | >100 | n.d. |
| 39 | >100 | n.d. |
| FUdR | 11.0 | 0.001 |
| FU | 1.6 | 3.7 |

Results from Test F demonstrate that representative compounds of formula VII unexpectedly possess significantly greater stability in human plasma than the compound FUdR. Because of this stability, compounds of formula VII may be superior to FUdR for treating cancer (e.g. breast cancer). Additionally, results from Test G demonstrate that representative compounds of formula VII (e.g. compounds 36 and 37) unexpectedly possess significantly improved activity against breast cancer cells compared to the compounds FUdR and FU.

The results from Test C, Test D, Test E, Test F, and Test G demonstrate the representative compounds of the invention possess anticancer properties and thus may be useful for treating cancer (e.g. breast cancer). Preferred compounds for treating cancer include compounds of formula I and II wherein $R_2$ and $R_7$ are hydroxy. Other preferred compounds for treating cancer are compounds of formula V wherein $R_{15}$ is an L-amino acid that comprises an aromatic group (e.g. aryl or heteroaryl) in the side chain. Other preferred compounds for treating cancer are compounds of formula VII wherein $R_{20}$ is an L-amino acid that comprises an aromatic group (e.g. aryl or heteroaryl) in the side chain.

The invention will now be illustrated by the following non-limiting Examples, wherein unless otherwise stated: NMR ($^1$H and $^{31}$P) spectra were recorded on Varian VXR-300 and GE Omega-300 spectrometers; an external standard of 85% $H_3PO_4$ was used for all $^{31}$P-NMR spectra; ESI mass spectra were obtained on a Finnigan TSQ 7000 mass spectrometer; analytical TLC was performed on Analtech Silica Gel GHLF (0.25 mm) or Machery-Nagel Polygram Sil G/UV$_{254}$ (0.2 mm) plates; concentration under reduced pressure refers to solvent removal on a Buchi rotary evaporator; high vacuum refers to <$10^{-2}$ psi attained with a DuoSeal mechanical pump; all solvents were reagent grade and used as received unless noted; and 3deaza adenosine and 3-deaza aristeromycin (which can be prepared using procedures similar to those described by J. A. Montgomery, et al. *J. Med. Chem.,* 1982, 25 626–629; and J. A. Montgomery, et al., *Hetrocycl. Chem.,* 1977, 14, 195, were obtained from Walter Reed Army Institute of Research, Washington, D.C.

EXAMPLE 1

3-Deaza adenosine-5-N-(1-carbomethoxy-2-phenylethyl) phosphoramidate (5)

To flask containing 3-deaza adenosine-5-monophosphate (3) (55 mg, 0.16 mmol) was added phenylalanine methyl ester (240 mg, 1.12 mmol), DCC (165 mg, 0.8 mmol), $^t$BuOH (5 mL), and water (1 mL). A reflux condenser was attached to the flask and the reaction heated in a boiling water bath for 4 h. After cooling to room temperature, the solvents were removed under reduced pressure. The resulting residue was resuspended in a mixture of water (20 mL) and ether (10 mL) and extracted with ether (1×10 mL). The aqueous phase was then lyophilized. The resulting solid was then subjected to purification by C-8 semi-prep HPLC (250 mm×10 Econosphere C8 10 µm). The HPLC system consisted of a Spectra-Physics SP8800 ternary HPLC pump and SP4600 integrator; a Kratos-Spectraflow 757 absorbance detector; and a Rheodyne manual injector. The compound was eluted by using a gradient of water (solvent A) and acetonitrile (solvent B) and monitored at 255 nm. The gradient ran at 5 mL/min and changed linearly from 94% A to 60% A over the first 15 min then held constat at 60% A for 2 min. The column was then washed by changing linearly back to 95% A. The fraction containing the phosphoramidate was collected from 9.3 min to 12.7 min. and lyophilized to give a white fluffy solid (24 mg, 30% yield). $R_f$=0.22 in $CHCl_3$:MeOH:$H_2O$ (5:3:0.5). $^1$H-NMR ($CD_3OD$): 8.51 (1H, s, H8), 7.65 (1H, d, H2), 7.30 (1H, m, H3), 7.22–7.08 (5H, m, Phe), 5.87 (1H, m, H1), 4.51 (1H, m, H2), 4.26 (1H, m, H3), 4.16 (1H, m, H4), 3.93 (1H, m, C$\underline{H}$CO$_2$Me), 3.86 (2H, m, H5), 3.59 (3H, s, CO$_2$CH$_3$), 2.93 (2H, m, PheCH$_2$). $^{31}$P-NMR (CD$_3$OD): 6.12. HPLC: $t_R$ 13.15 min.$^1$ The intermediate compound (3) was prepared as follows.
a. 3-Deaza adenosine-5-monophosphate (3). Triethyl phosphate (3mL) was placed in a dry flask and cooled to 0° C. in an ice bath under nitrogen. Distilled phosphorus oxychloride (177 µL, 1.9 mmol) was added, and then 3-deaza adenosine (1) (50 mg, 0.19 mmol) was added in one portion. The reaction mixture was stirred for 10 h at 0° C. then poured into a beaker containing crushed ice (10 mL) and the pH adjusted to 7.5 with sodium hydroxide (2 M). The aqueous solution was then extracted with chloroform (3×15 mL) and then ether (2×15 mL). The aqueous portion was then applied to a deactivated charcoal column (6 g, 1.5 cm×10 cm). The column was eluted with water (150 mL) then with 1.5 N ammonium hydroxide in ethanol—water (1:1) (200 mL). The latter eluant was concentrated to dryness and then taken up in water (0.5 mL) and then applied onto an ion-exchange column (BioRad AG-50W-X8, H$^+$, 0.75 in.×6 in.). The column was washed with water (60 mL) then the product eluted with formic acid (2 N). Fractions containing the product were combined and lyophilized. The product was isolated as a yellowish solid (53 mg, 81% yield). $^1$H-NMR (D$_2$O): 8.42 (1H, s, H8), 7.45 (1H, m, H2), 7.20 (1H, m, H3), 5.96 (1H, m, H1), 4.51 (1H, m, H2), 4.35 (1H, m, H3), 4.13 (3H, m, H4, H5). $^{31}$P-NMR (D$_2$O: 0.62. HPLC $t_R$ 1.23 min.$^1$ The title compound can also be prepared using the following procedure.

Triethylammonium 3-deazaadenosine-5'-phosphite (53) (92 mg, 0.214 mmol) was dissolved in 5 mL of dry pyridine and treated with TMSCl (163 µL, 1.28 mmol) under Ar. After 5 minutes, a solution of iodine (82 mg, 0.321 mmol) in 2 mL of pyrdine was added dropwise, via cannula, until the reaction color changed from yellow to a reddish-brown color. At this point, addition of the iodine solution was stopped. After 5 minutes, phenylalanine methyl ester (HCl salt, 92 mg, 0.428 mmol) and Et$_3$N (0.30 mL, 2.14 mmol) was added. After stirring for 50 min, the reaction mixture was concentrated under reduced pressure. The resulting syrup was partitioned between 1N NH$_4$OH solution and CHCl$_3$. The aqueous portion was then extracted with additional portions of CHCl$_3$ to remove unreacted amino acid methyl ester. The aqueous portion was then concentrated to give crude phosphoramidate which was passed through a small Amberlite (IRP-64) ion exchange column, eluting with H$_2$O, and the desired fractions were concentrated under reduced pressure. Flash chromatography (SiO$_2$, 5:3:0.5 CHCl$_3$/MeOH/H$_2$O) gave the desired product (39 mg) as a white solid. (MS, ESI) 508 (M+H); $^1$H NMR (D$_2$O, 300 MHz) 8.257 (s, 1H), 7.436 (d,J=6.8 Hz, 1H), 7.039 (d, J=6.8 Hz, 1H), 6.983–6.813 (m, 5H), 5,785 (d J=6.6 Hz, 1H), 4.416 (m, 1H), 4.181 (dd, J=2.9, 5.3 Hz, 1H), 4.094 (t, J=2.6 Hz, 1H), 3.720–3.546 (m, 3H), 3.433 (s, 3H), 2.688 (dd, J=7.0, 13.9 Hz, 1H), 2.626 (dd, J=7.3, 13.9 Hz, 1H); $^{31}$P NMR (D$_2$O, 121 MHz) 6.354.

The intermediate triethylammonium 3-deazaadenosine-5'-phosphite (53) can be prepared as follows.
b. 3-Deaza-2',3-O-ethoxymethylene adenosine (51). A suspension of 3-deazaadenosine (50, 300 mg, 1.13 mmol) in 4 mL of DMF was treated with triethyl orthoformate (0.56 mL, 3.39 mmol) and 1.44 mL of a 1.16 M solution of HCL in DMF (1.67 mmol). The solution become homogeneous and was stirred for 2 hours. Triethylamine (about 0.5 mL) was then added and the reaction mixture was filtered. The filtrate was concentrated under reduced pressure and the resulting material was purified by flash chromatography (SiO$_2$), 7% MeOH/CHCl$_3$ containing 0.2% NH$_4$OH) to give the ethoxymethylene compound.
c. Triethylamminium 3-deaza-2',3-O-ethyoxymethylene adenosine-5'-phosphite (52). Compound 51 was treated with diphenyl phosphite using a procedure similar to that described in Example 6, sub-part a, to give the adenosine-5'-phosphite.
d. Triethylamminium 3-deazaadenosine-5'-phosphite (53) Compound 52 was hydrolyzed under acidic conditions using dowex resin to give the deprotected adenosine salt.

EXAMPLE 2

3-Deaza adenosine-5-N-(1-carbomethoxy-2-indol-3-ylethyl)- phosphoramidate (6)

To a flask containing 3-deaza adenosine-5-monophosphate (3) (53 mg, 0.15 mmol) was added phenylalanine methyl ester (229 mg, 1.05 mmol), DCC (1.55 mg, 0.75 mmol), $^1$BuOH (5 mL), and water (1 mL). A reflux condenser was attached to the flask and the reaction heated in a boiling water bath for 4 h. After cooling to room temperature, the solvents were removed under reduced pressure. The resulting residue was resuspended in a mixture of water (20 mL) and extracted with ether (2×10 mL). The aqueous phase was then lyophilized. The resulting solid was then subjected to purification by C-8 semi-prep HPLC (250 mm×10 mm Econosphere C8 10 µm). The HPLC system and gradient were identical to the one described above. The fraction containing the phosphoramidate was collected from 13.0 min to 17.0 min. and lyophilized to give a white fluffy solid (15 mg, 19% yield). $R_f$=0.23 in $CHCl_3$:MeOH:$H_2O$ (5:3:0.5). $^1$H-NMR ($CD_3OD$): 8.42 (1H, s, H8), 7.55 (2H, m, H2, indole H4), 7.42 (1H, d, indole H7), 7.30–7.01 (4H, m, H3, indole H2, 5, 6), 5.86 (1H, m, H1), 4.49 (1H, m, H2), 4.20 (1H, m, H3), 4.13 (1H, m, H4), 4.00 (1H, m, C$\underline{H}CO_2Me$), 3.84 (2H, m, H5), 3.67 (3H, s, $CO_2CH_3$), 3.00 (2H, m, indoleCH$_2$). $^{31}$P-NMR ($CD_3OD$): 6.286. HPLC: $t_R$ 14.14 min.$^1$ The intermediate compound 4 was prepared as follows.

a. 3-Deaza aristeromycin-5-monophosphate (4). Triethyl phosphate (3 mL) was placed in a dry flask and cooled to 0° C. in an ice bath under nitrogen. Distilled phosphorus oxychloride (177 μL, 1.9 mmol) was added, then 3-deaza aristeromycin (2) (50 mg, 0.19 mmol) was added in one portion. The reaction mixture was stirred for 10 h at 0° C. then poured in to a beaker containing crushed ice (10 mL) and the pH adjusted to 7.5 with sodium hydroxide (2 M). The aqueous solution was then extracted with chloroform (3×15 mL) and then ether (2×15 mL). The aqueous portion was then applied to a deactivated charcoal column (6 g, 1.5 cm×10 cm). The column was eluted with water (150 mL) then with 1.5 N ammonium hydroxide in ethanol—water (1:1) (200 mL). The latter eluent was concentrated to dryness and then taken up in water (0.5 mL) and then applied onto an ion-exchange column (BioRad (AG-50W-X8, H$^+$, 0.75 in.×6 in.). The column was washed with water (60 mL) then the product eluted with formic acid (2N). Fractions containing the product was combined and lyophilized. The product was isolated as brownish solid (44 mg, 67% yield). $^1$H-NMR ($D_2O$): 8.42 (1H, s, H8), 7.55 (1H, d, H2), 7.20 (1H, m, H3), 4.72 (1H, m, H1), 4.33 (1H, m, H2), 4.09–3.90 (3H, m, H3, H6), 2.6–2.4 (2H, m, H4, H5), 1.9 (1H, m, H5). $^-$P-NMR ($D_2O$): 0.84.

The title compound can also be prepared as follows.

Compound 53 (119 mg, 0.276 mmol) was dissolved in 5 mL of dry pyridine and treated with TMSCl (210 μL, 1.66 mmol) under Ar. After 5 minutes, a solution of iodine (106 mg, 0.416 mmol) in 2mL of pyridine was added dropwise, via cannula, until the reaction color changed from yellow to a reddish-brown color. At this point, addition of the iodine solution was stopped. After 5 minutes, tryptophan methyl ester (HCl salt, 106 mg, 0.416 mmol) and $Et_3N$ (0.38 mL, 3.12 mmol) were added. After stirring for 60 minutes, the reaction mixture was concentrated under reduced pressure. The resulting syrup was partitioned between 1N $NH_4OH$ solution and $CHCl_3$. The aqueous portion was then extracted with additional portions of $CHCl_3$ to remove unreacted amino acid methyl ester. The aqueous portion was then concentrated to give crude phosphoramidate which was passed through a small Amberlite (IRP-64) ion exchange column, eluting with $H_2O$, and the desired fractions were concentrated under reduced pressure. Flash chromatography ($SiO_2$, 5:3:0.5 $CHCl_3$/MeOH/$H_2O$ containing 1% $NH_4OH$) gave the desired product (56 mg) as a white solid. (MS, ESI) 547 (M+H); $^1$H NMR ($D_2O$/$d_5$-pyridine, 300 MHz) 7.922 (s, 1H), 6.915 (d,J=6.6 Hz, 1H), 6.750 (m, 1H), 6.603 (m, 1H), 6.569 (s, 1H), 6.392–6.355 (m, 2H), 6.203–6.100 (M, 1H), 5.311 (d J=6.4 Hz, 1H), 4.083 (m, 1H), 3.973 (m, 1H), 3.771 (m, 1H), 3.697 (m, 1H), 3.559–3.433 (m, 2H), 2.727 (s, 3H), 2.523 (dd, J=5.7, 14.4 Hz, 1H), 2.449 (dd, J=7.0, 14.4 Hz, 1H); $^{31}$P NMR ($D_2O$, 81 MHz) 5.654.

EXAMPLE 3

3-Deaza aristeromycin-5-N-(1-carbomethoxy-2-phenylethyl)-phosphoramidate (7)

To a flask containing 3-deaza aristeromycin-5-monophosphate (4) (44 mg, 0.13 mmol) was added phenylalanine methyl ester (196 mg, 0.91 mmol), DCC (134 mg, 0.65 mmol), $^t$BuOH (5 mL), and water (1 mL). A reflux condenser was attached to the flask and the reaction heated in a boiling water bath for 7.5 h. After cooling to room temperature, the solvents were removed under reduced pressure. The resulting residue was resuspended in a mixture of water (20 mL) and ether (10 mL) and extracted with ether (1×10 mL). The aqueous phase was then lyophilized. The resulting solid was then subjected to purification C-8 semi-prep HPLC (250 mm×10 mm Econosphere C8 10 μm). The HPLC system was identical to the one described above. The compound was eluted by using a gradient of water (solvent A) and acetonitrile (solvent B) and monitored at 216 nm. The gradient ran at 4 mL/min and changed linearly from 90% A to 30% A over the first 10 min. then held constant at 30% A for 3 min. The column was then washed by changing linearly back to 90% A. The fraction containing the phosphoramidate was collected from 6.0 min to 10.0 min. and lyophilized to give a white fluffy solid (5 mg, 7.6% yield). $R_f$=0.23 in $CHCl_2$:MeOH:$H_2O$ (5:3:0.5). $^1$H-NMR ($CD_3OD$): 8.38 (1H, d, H8), 7.62 (1H, d, H2), 7.30–7.10 (6H, m, H3, Phe), 4.71 (1H, m, H1), 4.30 (1H, m, H2), 4.05 (1H, m, H3), 3.60 (1H, m, C$\underline{H}CO_2Me$), 3.52 (2H, d, H6), 3.28 (3H, s, $CO_2CH_3$), 2.95 (2H, m, PheCH$_2$), 2.35 (1H, m, H4), 2.20 (1H, m, H5), 1.92 (1H, m, H5). $^{31}$P-NMR ($CD_3OD$): 6.672. ESI-MS: m/e [M+H]$^+$ 506.2, [M+H CH$_3$]$^+$ 491.3, [M+H OCH$_3$]$^+$ 475.4 [M+H ring]$^+$ 372.2.

The purity of compounds 5 and 6 was also assessed by their analytical HPLC profile. Compounds were subjected to HPLC analysis on a 4.6×250 mm 5 μm Spherisorb reverse-phase C8 column. The HPLC system was identical to the one described above. Compounds were eluted using a gradient of 50 mM ammonium acetate (solvent A) and acetonitrile (solvent B) and monitored at 255 nm. The gradient ran at 1.5 mL/min and changed linearly from 95% A to 90% A over the first 5 min. From 5 to 15 min the gradient increased linearly to 70% A and from 15 to 18 min the gradient changed back to 95% A. The relative amounts of impurities were determined by comparing the peak area of the nucleoside and nucleotide to the area of the compound being evaluated. Purity was expressed as a percent of total area.

EXAMPLE 4

3-Deaza adenosine-5-N-(1-methylaminocarbonyl-2-phenylethyl) phosphoramidate (14)

Compound 5 (22 mg) was dissolved in 2 mL of 10 M methyl amine in methanol and stirred in a sealed vial for 6 d. The reaction mixture was then concentrated under reduced pressure. Flash chromatography ($SiO_2$, 5:3:0.5 $CHCl_3$/MeOH/$H_2O$ containing 0.5% conc. $NH_4OH$) gave the desired product (20 mg) as a white solid. (MS, ESI) 507 (M+H); $^1$H NMR ($D_2O$, 300 MHz) 8.189 (s, 1H), 7.407 (d, J=6.8 Hz, 1H), 6.999–6.857 (m, 6H), 5.732 (d, J=6.4 Hz, 1H), 4.357 (m, 1H), 4.085 (dd, J=2.9, 5.1 Hz, 1H), 4.032 (t, J=2.6 Hz, 1H), 3.596–3.491 (m, 2H), 3.405 (m, 1H), 2.707 (dd, J=4.9, 13.6 Hz, 1H), 2.572 (dd, J=7.6, 13.6 Hz, 1H), 2.464 (s, 3H); $^{31}$P NMR ($D_2O$, 121 MHz) 5.857.

EXAMPLE 5

3-Deaza adenosine-5-N-[1-methylaminocarbonyl-2-(3-indolyl)ethyl] phosphoramidate (16)

Compound 6 (30 mg) was dissolved in 1mL of 10 M methyl amine in methanol and stirred in a sealed vial for 5 days. The reaction mixture was then concentrated under reduced pressure. Flash chromatography (SiO$_2$, 5:3:0.5 CHCl$_3$/MeOH/H$_2$O containing 0.5% conc. NH$_4$OH) gave the desired product (30 mg) as a white solid. (MS, ESI) 546 (M+H); $^1$H NMR (D$_2$O, 300 MHz) 8.003 (s, 1H), 7.361 (d, J=6.1 Hz, 1H), 7.167 (d, J=8.1 Hz, 1H), 7.061 (d, J=8.1 Hz, 1H), 6.869 (s, 1H), 6.817–6.735 (m, 2H), 6.613 (m, 1H), 5.605 (d, J=6.2 Hz, 1H), 4.264 (m, 1H), 4.022 (dd, J=3.4, 5.2 Hz, 1H), 3.959 (t, J=2.6 Hz, 1H), 3.633 (m, 1H), 3.549 (m, 1H), 3.415 (m, 1H), 2.850 (dd, J=5.9, 14.5 Hz, 1H), 2.747 (dd, J=7.0, 14.5 Hz, 1H), 2.428 (s, 3H); $^{31}$P NMR (D$_2$O, 81 MHz) 6.194.

EXAMPLE 6

3'-Azido-3'-deoxythymidine-5'-methoxyglycinyl phosphoramidate (17)

Compound 40 (190 mg, 0.439 mmol) was dissolved in 7 mL of dry pyridine and treated with TMSCl (167 μL, 1.32 mmol) under Ar. After 5 minutes, a solution of iodine (167 mg, 0.659 mmol) in 3 mL of pyridine was added dropwise, via cannula, until the reaction color changed from yellow to a reddish-brown color. At this point, addition of the iodine solution was stopped. After 5 minutes, glycine methyl ester (HCl salt, 110 mg, 0.878 mmol) and Et$_3$N (0.43 mL, 3.08 mmol) were added. After stirring for 30 minutes, the reaction mixture was concentrated under reduced pressure. The resulting syrup was partitioned between 1N NH$_4$OH solution and CHCl$_3$. The aqueous portion was then extracted with additional portions of CHCl$_3$ to remove unreacted amino acid methyl ester. The aqueous portion was then concentrated to give crude phosphoramidate which was passed through a small Amberlite (IRP-64) ion exchange column, eluting with H$_2$O, and the desired fractions were concentrated under reduced pressure. Flash chromatography SiO$_2$, 5:2:0.25 CHCl$_3$/MeOH/H$_2$O containing 0.5% conc. NH$_4$OH) gave the desired product (94 mg) as a slightly pink colored solid. $^1$H NMR (D$_2$O, 300 MHz) 7.550 (d, J=1 Hz, 1H), 6.091 (t, J=6.7 Hz, 1H), 4.311 (m, 1H), 3.978 (m, 1H), 3.935–3.787 (m, 2H), 3.505 (s, 3H), 3.465 (d, J=11.5 Hz, 2H), 2.354–2.303 (m, 2H), 1.753 (d, J=1 Hz, 3H); $^{31}$P NMR (D$_2$O, 121 MHz) 7.855.

The intermediate triethylammonium phosphite (40) was prepared as follows (FIG. 9).

a. Triethylammonium 3'-azido-3'-deoxythymidine-5'-phosphite (40). A solution of AZT (755 mg, 2.83 mmol) dissolved in 7 mL of dry pyridine was added dropwise over 40 minutes to a stirred solution of diphenyl phosphite (541 μL, 2.83 mmol) in 8 mL of dry pyridine under an Argon atmosphere. After stirring for 2 h, Et$_3$N (3 mL) and H$_2$O (3 mL) were added and stirring was continued for 15 minutes. The reaction mixture was then concentrated under reduced pressure. The resulting residue was dissolved in H$_2$O and extracted with CH$_2$Cl$_2$ (4×). The aqueous portion was then concentrated under reduced pressure. The resulting solid was then purified by flash chromatography (SiO$_2$, 9:1 CHCl$_3$/MeOH followed by 5:2:0.25 CHCl$_3$/MeOH/ H$_2$O containing 0.5% NH$_4$OH) to give the desired product (840 mg) as a colorless solid. $^1$H NMR (D$_2$O, 300 MHz) 7.522 (d, J=1.1 Hz, 1H), 6.604 (d, J=638 Hz, 1H), 6.090 (t, J=6.7 Hz, 1H), 4.326 (m, 1H), 4.009 (m, 1H), 3.933 (m, 2H), 3.023 (q, J=7.3 Hz, 6H), 2.328 (m, 2H), 1.736 (d, J=1.1 Hz, 3H), 1.100 (t, J=7.3 Hz, 9H); $^{31}$P NMR (D$_2$O, 121 MHz) 6.856.

EXAMPLE 7

3'-Azido-3'-deoxythymidine-5'-methoxy-L-alaninylphosphoramidate (19)

Compound 40 (160 mg, 0.370 mmol) was dissolved in 6 mL of dry pyridine and treated with TMSCl (141 μL, 1.11 mmol) under Ar. After 5 minutes, a solution of iodine (141 mg, 0.555 mmol) in 2 mL of pyridine was added dropwise, via cannula, until the reaction color changed from yellow to a reddish-brown color. At this point, addition of the iodine solution was stopped. After 5 minutes, alanine methyl ester (HCl salt, 103 mg, 0.740 mmol) and Et$_3$N (0.36 mL, 2.59 mmol) were added. After stirring for 40 minutes, the reaction mixture was concentrated under reduced pressure. The resulting syrup was partitioned between 1N NH$_4$OH solution and CHCl$_3$. The aqueous portion was then extracted with additional portions of CHCl$_3$ to remove unreacted amino acid methyl ester. The aqueous portion was then concentrated to give crude phosphoramidate which was passed through a small Amberlite (IRP-64) ion exchange column, eluting with H$_2$O, and the desired fractions were concentrated under reduced pressure. Flash chromatography (SiO$_2$, 5:2:0.25 CHCl$_3$/MeOH/H$_2$O containing 0.5% conc. NH$_4$OH) gave the desired product (79 mg) as a white solid. $^1$H NMR (D$_2$O, 300 MHz) 7.557 (d, J=1.1 Hz, 1H), 6.085 (t, J=6.7 Hz, 1H), 4.298 (m, 1H), 3.993 (m, 1H), 3.898–3.776 (m, 2H), 3.620 (m, 1H), 3.536 (s, 3H), 2.331 (m, 2H), 1.760 (d, J=1.1 Hz, 3H), 1.141 (d, J=6.9 Hz, 3H); $^{31}$P NMR (D$_2$O, 121 MHz) 6.626.

EXAMPLE 8

3'-Azido-3'-deoxythymidine-5'-methoxy-L-valinylphosphoramidate (20)

Compound 40 (290 mg, 0.670 mmol) was dissolved in 6 mL of dry pyridine and treated with TMSCl (255 μL, 2.01 mmol) under Ar. After 5 minutes, a solution of iodine (255 mg, 1.01 mmol) in 4 mL of pyridine was added dropwise, via cannula, until the reaction color changed from yellow to a reddish-brown color. At this point, addition of the iodine solution was stopped. After 5 minutes, valine methyl ester (HCl salt, 225 mg, 1.34 mmol) and Et$_3$N (0.65 mL, 4.7 mmol) were added. After stirring for 15 minutes, the reaction mixture was concentrated under reduced pressure. The resulting syrup was partitioned between 1N NH$_4$OH solution and CHCl$_3$. The aqueous portion was then extracted with additional portions of CHCl$_3$ to remove unreacted amino acid methyl ester. The aqueous portion was then concentrated to give crude phosphoramidate which was passed through a small Amberlite (IRP-64) ion exchange column, eluting with H$_2$O, and the desired fractions were concentrated under reduced pressure. Flash chromatography (SiO$_2$, 5:2:0.25 CHCl$_3$/MeOH/H$_2$O containing 0.5% conc. NH$_4$OH) gave the desired product (85 mg) as a white solid. $^1$H NMR (D$_2$O, 300 MHz) 7.573 (d, J=1.1 Hz, 1H), 6.077 (t, J=6.7 Hz, 1H), 4.293 (m, 1H), 3.994 (m, 1H), 3.907–3.752 (m, 2H), 3.550 (s, 3H), 3.338 (m, 1H), 2.328 (m, 2H), 1.778 (d, J=1.1 Hz, 3H), 1.772 (m, 1H), 0.725 (d, J=6.8 Hz, 3H), 0.715 (d, J=6.8 Hz, 3H); $^{31}$P NMR (D$_2$O, 121 MHz) 7.166.

EXAMPLE 9

3'-Azido-3'-deoxythymidine-5'-methoxy-L-leucinylphosphoramidate (21)

Compound 40 (287 mg, 0.663 mmol) was dissolved in 6 mL of dry pyridine and treated with TMSCl (250 μL, 1.97 mmol) under Ar. After 5 minutes, a solution of iodine (253 mg, 1.00 mmol) in 4 mL of pyridine was added dropwise, via cannula, until the reaction color changed from yellow to a reddish-brown color. At this point, addition of the iodine solution was stopped. After 5 minutes, leucine methyl ester (HCl salt, 240 mg, 1.32 mmol) and Et$_3$N (0.65 mL, 4.7 mmol) were added. After stirring for 80 minutes, the reaction mixture was concentrated under reduced pressure. The resulting syrup was partitioned between 1N NH$_4$OH solution and CHCl$_3$. The aqueous portion was then extracted with additional portions of CHCl$_3$ to remove unreacted amino acid methyl ester. The aqueous portion was then concentrated to give crude phosphoramidate which was passed through a small Amberlite (IRP-64) ion exchange column, eluting with H$_2$O, and the desired fractions were concentrated under reduced pressure. Flash chromatography (SiO$_2$, 5:2:0.25 CHCl$_3$/MeOH/H$_2$O containing 0.5% conc. NH$_4$OH) gave the desired product (98 mg) as a white solid. $^1$H NMR (D$_2$O, 300 MHz) 7.600 (d, J=1.1 Hz, 1H), 6.086 (t, J=6.8 Hz, 1H), 4.303 (m, 1H), 3.987 (m, 1H), 3.895–3.747 (m, 2H), 3.538 (m, 1H), 3.538 (s, 3H), 2.324 (m, 2H), 1.771 (d, J=1.1 Hz, 3H), 1.485 (m, 1), 1.335–1.278 (m, 2H), 0.672 (d, J=6.6 Hz, 6H); $^{31}$P NMR (D$_2$O, 121 MHz) 6.701.

EXAMPLE 10

3'-Azido-3'-deoxythymidine-5'-methoxy-L-tyrosinylphosphoramidate (22)

Compound 40 (243 mg, 0.561 mmol) was dissolved in 7 mL of dry pyridine and treated with TMSCl (213 μL, 1.69 mmol) under Ar. After 5 minutes, a solution of iodine (214 mg, 0.842 mmol) in 3 mL of pyridine was added dropwise, via cannula, until the reaction color changed from yellow to a reddish-brown color. At this point, addition of the iodine solution was stopped. After 5 minutes, tyrosine methyl ester (219 mg, 1.12 mmol) and Et$_3$N (0.40 mL, 2.81 mmol) were added. After stirring for 60 minutes, the reaction mixture was concentrated under reduced pressure. The resulting syrup was partitioned between 1N NH$_4$OH solution and CHCl$_3$. The aqueous portion was then extracted with additional portions of CHCl$_3$ to remove unreacted amino acid methyl ester. The aqueous portion was then concentrated to give crude phosphoramidate which was passed through a small Amberlite (IRP-64) ion exchange column, eluting with H$_2$O, and the desired fractions were concentrated under reduced pressure. Flash chromatography (SiO$_2$, 5:2:0.25 CHCl$_3$/MeOH/H$_2$O containing 0.5% conc. NH$_4$OH) gave the desired product (149 mg) as a white solid. $^1$H NMR (D$_2$O, 300 MHz) 7.401 (s, 1H), 6.859 (d, J=7.3 Hz, 2H), 6.547 (d, J=8.2 Hz, 2H), 6.000 (t, J=6.6 Hz, 1H), 4.119 (m, 1H), 3.845 (m, 1H), 3.647 (m, 1H), 3.620–3.540 (m, 2H), 3.486 (s, 3H), 2.718 (dd, J=6.2, 13.5 Hz, 1H), 2.591 (dd, J=7.7, 13.5 Hz, 1H), 2.230 (m, 1H), 2.105 (m, 1H), 1.662 (s, 3H); $^{31}$P NMR (D$_2$O, 121 MHz) 6.487.

EXAMPLE 11

3'-Azido-3'-deoxythymidine-5'-methylaminoglycinylphosphoramidate (23)

Compound 17 (35 mg) was dissolved in 2 mL of 10 M methyl amine in methanol and stirred in a sealed vial for 5 d. The reaction mixture was then concentrated under reduced pressure. Flash chromatography (SiO$_2$, 5:2.5:0.37 CHCl$_3$/MeOH/H$_2$O containing 0.5% conc. NH$_4$OH) gave the desired product (32 mg) was awhite solid. $^1$H NMR (D$_2$O, 300 MHz) 7.538 (d, J=1.1 Hz, 1H), 6.089 (t, J=6.7 Hz, 1H), 4.302 (m, 1H), 3.993 (m, 1H), 3.920–3.785 (m, 2H), 3.305 (d, J=11.2 Hz, 2H), 2.571 (s, 3H), 2.323 (m, 2H), 1.735 (d, J=1.1 Hz, 3H); $^{31}$P NMR (D$_2$O, 121 MHz) 7.956.

EXAMPLE 12

3'-Azido-3'-deoxythymidine-5'-methylamino-L-alaninylphosphoramidate (24)

Compound 19 (49 mg) was dissolved in 2 mL of 10 M methyl amine in methanol and stirred in a sealed vial for 5 d. The reaction mixture was then concentrated under reduced pressure. Flash chromatography (SiO$_2$, 5:2.5:0.37 CHCl$_3$/MeOH/H$_2$O containing 0.5% conc. NH$_4$OH) gave the desired product (41 mg) was awhite solid. $^1$H NMR (D$_2$O, 300 MHz) 7.5487 (d, J=1.1 Hz, 1H), 6.083 (t, J=6.8 Hz, 1H), 4.283 (m, 1H), 3.988 (m, 1H), 3.889–3.757 (m, 2H), 3.440 (m, 1H), 2.566 (s, 3H), 2.313 (m, 2H), 1.733 (d, J=1.1 Hz, 3H), 1.120 (d, J=7.1 Hz, 3H); $^{31}$P NMR (D$_2$O, 121 MHz) 6.685.

EXAMPLE 13

3'-Azido-3'-deoxythymidine-5'-methylamino-L-valinylphosphoramidate (25)

Compound 20 (62 mg) was dissolved in 2 mL of 10 M methyl amine in methanol and stirred in a sealed vial for 50 d. The reaction mixture was then concentrated under reduced pressure. Flash chromatography (SiO$_2$, 5:2:0.25 CHCl$_3$/MeOH/H$_2$O containing 0.5% conc. NH$_4$OH) gave the desired product (40 mg) was awhite solid. $^1$H NMR (D$_2$O, 300 MHz) 7.567 (d, J=1.1 Hz, 1H), 6.082 (t, J=6.8 Hz, 1H), 4.257 (m, 1H), 3.999 (m, 1H), 3.895–3.738 (m, 2H), 3.220 (m, 1H), 2.583 (s, 3H), 2.318 (m, 2H), 1.828 (m, 1H), 1.762 (d, J=1.1 Hz, 3H), 0.759 (d, J=6.8 Hz, 3H), 0.692 (d, J=6.8 Hz, 3H); $^{31}$P NMR (D$_2$O, 121 MHz) 6.851.

EXAMPLE 14

3'-Azido-3'-deoxythymidine-5'-methylamino-L-leucinyl-phosphoramidate (26)

Compound 21 (38 mg) was dissolved in 2 mL of 10 M methyl amine in methanol and stirred in a sealed vial for 50 d. The reaction mixture was then concentrated under reduced pressure. Flash chromatography (SiO$_2$, 5:2:0.25 CHCl$_3$/MeOH/H$_2$O containing 0.5% conc. NH$_4$OH) gave the desired product (25 mg) was awhite solid. $^1$H NMR (D$_2$O, 300 MHz) 7.588 (d, J=1.1 Hz, 1H), 6.081 (t, J=6.8 Hz, 1H), 4.275 (m, 1H), 3.995 (m, 1H), 3.896–3.746 (m, 2H), 3.403 (m, 1H), 2.570 (s, 3H), 2.320 (m, 2H), 1.753 (d, J=1.1 Hz, 3H), 1.504 (m, 1H), 1.352–1.225 (m, 2H), 0.693 (d, J=6.6 Hz, 6H); $^{31}$P NMR (D$_2$O, 121 MHz) 6.359.

EXAMPLE 15

3'-Azido-3'-deoxythymidine-5'-methylamino-L-phenylalaninylphosphoramidate (27)

Compound 40 (258 mg, 0.593 mmol) was dissolved in 8 mL of dry pyridine and treated with TMSCl (226 μL, 1.78 mmol) under Ar. After 5 minutes, a solution of iodine (226 mg, 0.890 mmol) in 2 mL of pyridine was added dropwise, via cannula, until the reaction color changed from yellow to a reddish-brown color. At this point, addition of the iodine solution was stopped. After 5 minutes, phenylalanine methyl amide (195 mg, 1.10 mmol) and Et$_3$N (0.41 mL, 2.94 mmol) were added in 2 mL of pyridine. After stirring for 30 minutes, the reaction mixture was concentrated under reduced pressure. The resulting syrup was partitioned between 1N NH$_4$OH solution and CHCl$_3$. The aqueous portion was then extracted with additional portions of CHCl$_3$ to remove unreacted amino acid methyl amide. The aqueous portion was then concentrated to give crude phosphoramidate which was passed through a small Amberlite (IRP-64) ion exchange column, eluting with H$_2$O, and the desired fractions were concentrated under reduced pressure. Flash chromatography (SiO$_2$, 5:2:0.25 CHCl$_3$/MeOH/H$_2$O containing 0.5% conc. NH$_4$OH) gave the desired product (81 mg) as a white solid. $^1$H NMR (D$_2$O, 300 MHz) 7.442 (d, J=1.0 Hz, 1H), 7.178–7.061 (m, 5H), 6.007 (t, J=6.7 Hz, 1H), 4.120 (m, 1H), 3.832 (m, 1H), 3.634 (m, 1H), 3.517–3.383 (m, 2H), 2.877 (ddd, J=1.8, 5.5, 13.7 Hz, 1H), 2.685 (dd, J=8.1, 13.7 Hz, 1H), 2.540 (s, 3H), 2.259 (m, 1H), 2.139 (m, 1H), 1.716 (d, J=1.0 Hz, 3H)); $^{31}$P NMR (D$_2$O, 121 MHz) 5.734.

EXAMPLE 16

3'-Azido-3'-deoxythymidine-5'-methylamino-D-phenylalaninylphosphoramidate (28)

Compound 40 (311 mg, 0.718 mmol) was dissolved in 7 mL of dry pyridine and treated with TMSCl (273 µL, 2.15 mmol) under Ar. After 5 minutes, a solution of iodine (273 mg, 1.08 mmol) in 3 mL of pyridine was added dropwise, via cannula, until the reaction color changed from yellow to a reddish-brown color. At this point, addition of the iodine solution was stopped. After 5 minutes, D-phenylalanine methyl amide (256 mg, 1.44 mmol) and Et$_3$N (0.50 mL, 3.59 mmol) were added. After stirring for 45 minutes, the reaction mixture was concentrated under reduced pressure. The resulting syrup was partitioned between 1N NH$_4$OH solution and CHCl$_3$. The aqueous portion was then extracted with additional portions of CHCl$_3$ to remove unreacted amino acid methyl amide. The aqueous portion was then concentrated to give crude phosphoramidate which was passed through a small Amberlite (IRP-64) ion exchange column, eluting with H$_2$O, and the desired fractions were concentrated under reduced pressure. Flash chromatography (SiO$_2$, 5:2:0.25 CHCl$_3$/MeOH/H$_2$O containing 0.5% conc. NH$_4$OH) gave the desired product (175 mg) as a white solid. $^1$H NMR (D$_2$O, 300 MHz) 7.387 (d, J=1.1 Hz, 1H), 7.193–7.032 (m, 5H), 6.022 (t, J=6.7 Hz, 1H), 4.066 (m, 1H), 3.807 (m, 1H), 3.653–3.532 (m, 2H), 3.295 (m, 1H), 2.822–2.687 (m, 2H), 2.470 (s, 3H), 2.308–2.169 (m, 2H), 1.657 (d, J=1.1 Hz, 3H); $^{31}$P NMR (D$_2$O, 121 MHz) 5.713.

EXAMPLE 17

3'-Azido-3'-deoxythymidine-5'-methylamino-L-tyrosinylphosphoramidate (29)

Compound 22 (51 mg) was dissolved in 2 mL of 10 M methyl amine in methanol and stirred in a sealed vial for 5 d. The reaction mixture was then concentrated under reduced pressure. Flash chromatography (SiO$_2$, 5:2.5:0.37 CHCl$_3$/MeOH/H$_2$O containing 0.5% conc. NH$_4$OH) gave the desired product (36 mg) as awhite solid. $^1$H NMR (D$_2$O, 300 MHz) 7.401 (d, J=1.0 Hz, 1H), 6.932 (d, J=8.6 Hz, 2H), 6.581 (d, J=8.6 Hz, 2H), 5.978 (t, J=6.6 Hz, 1H), 4.040 (m, 1H), 3.807 (m, 1H), 3.550 (m, 1H), 3.483–3.400 (m, 2H), 2.799 (m, 1H), 2.542 (s, 3H), 2.534 (m, 1H), 2.240 (m, 1H), 2.093 (m, 1H), 1.696 (d, J=1.0 Hz, 3H); $^{31}$P NMR (D$_2$O, 121 MHz) 5.761.

EXAMPLE 18

3'-Azido-3'-deoxythymidine-5'-methylamino-L-tryptophanylphosphoramidate (30)

3'-Azido-3'-deoxythymidine-5'-phosphate (140 mg, 0.403 mmol) was disolved in 5 mL of t-butanol and 1 mL of H$_2$O. Dicyclohexylcarbodiimide (415 mg, 2.30 mmol) and tryptophan methyl amide (500 mg, 2.30 mmol) were added and the reaction mixture was heated to reflux. After 5 hours, the reaction mixture was cooled and concentrated under reduced pressure. The resulting syrup was dissolved in water and extracted with diethylether (3×) to remove unreacted amino acid methyl amide. The aqueous portion was concentrated to give material that was purified by flash chromatography (SiO$_2$, 5:2:0.37 CHCl$_3$/MeOH/H$_2$O) to give the desired product (211 mg) as a white solid. $^1$H NMR (D$_2$O, 300 MHz) 7.470 (dd, J=0.7, 7.9 Hz, 1H), 7.258 (dd, J=0.7, 8.1 Hz, 1H), 7.219 (s, 1H), 7.086 (s, 1H), 7.011 (dd, J=7.1, 8.1 Hz, 1H), 6.904 (dd, J=7.1, 7.9 Hz, 1H), 5.850 (t, J=6.6 Hz, 1H), 4.019 (m, 1H), 3.778 (m, 1H), 3.721 (m, 1H), 3.584–3.444 (m, 2H), 3.122 (m, 1H), 2.846 (dd, J=8.2, 14.6 Hz, 1H), 2.615 (s, 3H), 2.095 (m, 1H), 1.853 (m, 1H), 1.619 (s, 3H); $^{31}$P NMR (D$_2$O, 121 MHz) 6.054.

The straring material 3'-azido-3'-deoxythymidine-5'-phosphate can be prepared using a procedure similar to that described by E. I. McIntee, et al. *J. Med. Chem.*, 1997, 40, 3323–3331.

EXAMPLE 19

3'-Azido-3'-deoxythymidine-5'-methylamino-D-tryptophanylphosphoramidate (31)

Compound 40 (411 mg, 0.949 mmol) was dissolved in 7 mL of dry pyridine and treated with TMSCl (360 µL, 2.84 mmol) under Ar. After 5 minutes, a solution of iodine (360 mg, 1.42 mmol) in 3 mL of pyridine was added dropwise, via cannula, until the reaction color changed from yellow to a reddish-brown color. At this point, addition of the iodine solution was stopped. After 5 minutes, D-tryptophan methyl amide (280 mg, 1.29 mmol) and Et$_3$N (0.66 mL, 4.75 mmol) were added. After stirring for 165 minutes, the reaction mixture was concentrated under reduced pressure. The resulting syrup was partitioned between 1N NH$_4$OH solution and CHCl$_3$. The aqueous portion was then extracted with additional portions of CHCl$_3$ to remove unreacted amino acid methyl amide. The aqueous portion was then concentrated to give crude phosphoramidate which was passed through a small Amberlite (IRP-64) ion exchange column, eluting with H$_2$O, and the desired fractions were concentrated under reduced pressure. Flash chromatography (SiO$_2$, 5:2:0.25 CHCl$_3$/MeOH/H$_2$O containing 0.5% conc. NH$_4$OH) gave the desired product (211 mg) as a white solid. $^1$H NMR (D$_2$O, 300 MHz) 7.425 (d, J=7.9 Hz, 1H), 7.267 (d, J=7.3 Hz, 1H), 7.193 (d, J=1.1 Hz, 1H), 7.020 (s, 1H), 7.007 (m, 1H), 6.885 (m, 1H), 5.860 (t, J=6.8 Hz, 1H), 3.779 (m, 1H), 3.725 (m, 1H), 3.647–3.552 (m, 2H), 3.177 (m, 1H), 3.025 (m, 1H), 2.835 (dd, J=7.5, 14.5 Hz, 1H), 2.472 (s, 3H), 2.121 (m, 1H), 1.862 (m, 1H), 1.525 (d, J=1.1 Hz, 1H); $^{31}$P NMR (D$_2$O, 121 MHz) 6.028.

EXAMPLE 20

3'-Azido-3'-deoxythymidine-5'-ethylamino-L-tryptophanylphosphoramidate (32)

Compound 40 (138 mg, 0.319 mmol) was dissolved in 5 mL of dry pyridine and treated with TMSCl (121 µL, 0.957 mmol) under Ar. After 5 minutes, a solution of iodine (122 mg, 0.479 mmol) in 2 mL of pyridine was added dropwise, via cannula, until the reaction color changed from yellow to a reddish-brown color. At this point, addition of the iodine solution was stopped. After 5 minutes, tryptophan ethyl amide (111 mg, 0.479 mmol) and Et$_3$N (0.22 mL, 1.60 mmol) were added. After stirring for 40 minutes, the reaction mixture was concentrated under reduced pressure. The resulting syrup was partitioned between 1N NH$_4$OH solution and CHCl$_3$. The aqueous portion was then extracted with additional portions of CHCl$_3$ to remove unreacted amino acid ethyl amide. The aqueous portion was then concentrated to give crude phosphoramidate which was passed through a small Amberlite (IRP-64) ion exchange column, eluting with $H_2O$, and the desired fractions were concentrated under reduced pressure. Flash chromatography ($SiO_2$, 5:2:0.25 $CHCl_3/MeOH/H_2O$ containing 0.5% conc. $NH_4OH$) gave the desired product (103 mg) as a white solid. $^1H$ NMR ($D_2O$, 300 MHz) 7.433 (d, J=7.9 Hz, 1H), 7.221 (d, J=8.1 Hz, 1H), 7.207 (s, 1H), 7.030 (s, 1H), 6.978 (m, 1H), 6.871 (m, 1H), 5.832 (t, J=6.6 Hz, 1H), 4.012 (m, 1H), 3.768 (m, 1H), 3.691 (m, 1H), 3.538 (m, 2H), 3.053 (m, 1H), 3.010 (q, J=7.3 Hz, 2H), 2.855 (dd, J=7.5, 14.5 Hz, 1H), 2.080 (m, 1H), 1.868 (m, 1H), 1.575 (s, 3H), 0.837 (t, J=7.3 Hz, 3H); $^{31}P$ NMR ($D_2O$, 121 MHz) 6.140.

EXAMPLE 21

3'-Azido-3'-deoxythymidine-5'-isopropylamino-L-tryptophanylphosphoramidate (33)

Compound 40 (116 mg, 0.268 mmol) was dissolved in 5 mL of dry pyridine and treated with TMSCl (102 μL, 0.804 mmol) under Ar. After 5 minutes, a solution of iodine (102 mg, 0.402 mmol) in 2 mL of pyridine was added dropwise, via cannula, until the reaction color changed from yellow to a reddish-brown color. At this point, addition of the iodine solution was stopped. After 5 minutes, tryptophan isopropyl amide (98 mg, 0.402 mmol) and $Et_3N$ (0.19 mL, 1.34 mmol) were added. After stirring for 60 minutes, the reaction mixture was concentrated under reduced pressure. The resulting syrup was partitioned between 1N $NH_4OH$ solution and $CHCl_3$. The aqueous portion was then extracted with additional portions of $CHCl_3$ to remove unreacted amino acid isopropyl amide. The aqueous portion was then concentrated to give crude phosphoramidate which was passed through a small Amberlite (IRP-64) ion exchange column, eluting with $H_2O$, and the desired fractions were concentrated under reduced pressure. Flash chromatography ($SiO_2$, 5:2:0.25 $CHCl_3/MeOH/H_2O$ containing 0.5% conc. $NH_4OH$) gave the desired product (44 mg) as a white solid. $^1H$ NMR ($D_2O$, 300 MHz) 7.426 (d, J=7.9 Hz, 1H), 7.232 (s, 1H), 7.219 (d, J=7.9 Hz, 1H), 7.010 (s, 1H), 6.975 (m, 1H), 6.872 (m, 1H), 5.857 (t, J=6.7 Hz, 1H), 4.051 (m, 1H), 3.793 (m, 1H), 3.713–3.624 (m, 2H), 3.583 (m, 2H), 3.011 (dd, J=5.5, 14.6 Hz, 1H), 2.882 (dd, J=7.1, 14.6 Hz, 1H), 2.110 (m, 1H), 1.929 (m, 1H), 1.566 (s, 3H), 0.837 (d, J=6.1 Hz, 3H), 0.816 (d, J=6.1 Hz, 3H); $^{31}P$ NMR ($D_2O$, 121 MHz) 6.161.

EXAMPLE 22

3'-Azido-3'-deoxythymidine-5'-cyclopropylamino-L-tryptophanylphosphoramidate (34)

Compound 40 (166 mg, 0.383 mmol) was dissolved in 5 mL of dry pyridine and treated with TMSCl (146 μL, 1.15 mmol) under Ar. After 5 minutes, a solution of iodine (146 mg, 0.575 mmol) in 2 mL of pyridine was added dropwise, via cannula, until the reaction color changed from yellow to a reddish-brown color. At this point, addition of the iodine solution was stopped. After 5 minutes, tryptophan cyclopropyl amide (140 mg, 0.575 mmol) and $Et_3N$ (268 μL, 1.92 mmol) were added. After stirring for 75 minutes, the reaction mixture was concentrated under reduced pressure. The resulting syrup was partitioned between 1N $NH_4OH$ solution and $CHCl_3$. The aqueous portion was then extracted with additional portions of $CHCl_3$ to remove unreacted amino acid methyl amide. The aqueous portion was then concentrated to give crude phosphoramidate which was passed through a small Amberlite (IRP-64) ion exchange column, eluting with $H_2O$, and the desired fractions were concentrated under reduced pressure. Flash chromatography ($SiO_2$, 5:2:0.25 $CHCl_3/MeOH/H_2O$ containing 0.5% conc. $NH_4OH$) gave the desired product (98 mg) as a white solid. $^1H$ NMR ($D_2O$, 300 MHz) 7.409 (d, J=7.9 Hz, 1H), 7.211 (d, J=7.3 Hz, 1H), 7.201 (d, J=1.0 Hz, 1H), 6.991 (s, 1H), 6.970 (m, 1H), 6.865 (m, 1H), 5.824 (t, J=6.6 Hz, 1H), 4.021 (m, 1H), 3.771 (m, 1H), 3.664 (m, 1H), 3.554 (m, 2H), 2.996 (m, 1H), 2.845 (dd, J=7.3, 14.5 Hz, 1H), 2.341 (m, 1H), 2.078 (m, 1H), 1.876 (m, 1H), 1.560 (d, J=1.0 Hz, 3H), 0.506 (m, 2H), 0.179 (m, 2H); $^{31}P$ NMR ($D_2O$, 121 MHz) 6.113.

EXAMPLE 23

3'-Azido-3'-deoxythymidine-5'-cyclohexylamino-L-tryptophanylphosphoramidate (35)

Compound 40 (207 mg, 0.478 mmol) was dissolved in 7 mL of dry pyridine and treated with TMSCl (182 μL, 1.43 mmol) under Ar. After 5 minutes, a solution of iodine (182 mg, 0.717 mmol) in 3 mL of pyridine was added dropwise, via cannula, until the reaction color changed from yellow to a reddish-brown color. At this point, addition of the iodine solution was stopped. After 5 minutes, tryptophan cyclohexyl amide (204 mg, 0.717 mmol) and $Et_3N$ (0.33 mL, 2.39 mmol) were added. After stirring for 45 minutes, the reaction mixture was concentrated under reduced pressure. The resulting syrup was partitioned between 1N $NH_4OH$ solution and $CHCl_3$. The aqueous portion was then extracted with additional portions of $CHCl_3$ to remove unreacted amino acid cyclohexyl amide. The aqueous portion was then concentrated to give crude phosphoramidate which was passed through a small Amberlite (IRP-64) ion exchange column, eluting with $H_2O$, and the desired fractions were concentrated under reduced pressure. Flash chromatography ($SiO_2$, 7:2:0.25 $CHCl_3/MeOH/H_2O$ containing 0.5% conc. $NH_4OH$) gave the desired product (156 mg) as a white solid. $^1H$ NMR ($D_2O$, 300 MHz) 7.415 (d, J=7.9 Hz, 1H), 7.262 (d, J=1.0 Hz, 1H), 7.224 (d, J=8.1 Hz, 1H), 6.996 (s, 1H), 6.976 (m, 1H), 6.875 (m, 1H), 5.878 (t, J=6.7 Hz, 1H), 4.084 (m, 1H), 3.812 (m, 1H), 3.694 (m, 1H), 3.633 (m, 2H), 3.282 (m, 1H), 2.961 (m, 2H), 2.133 (m, 1H), 1.986 (m, 1H), 1.560 (d, J=1.0 Hz, 3H), 1.473–1.341 (m, 5H), 1.107–0.94 (m, 2H), 0.924–0.745 (m, 3H); $^{31}P$ NMR ($D_2O$, 121 MHz) 6.242.

EXAMPLE 24

3-Azido-3-deoxythymidine-5-methoxy-L-phenylalaninylphosphoramidate (11)

Compound 40 (277 mg, 0.640 mmol) and phenylalanine methyl ester (HCl salt, 276 mg, 1.28 mmol) were subjected to a procedure similar to that described in Example 6. Flash chromatography ($SiO_2$, 5:2:0.25 $CHCl_3/MeOH/H_2O$ containing 0.5% conc. $NH_4OH$) gave the title compound (216 mg, 64%) as a white solid. $^1H$ NMR ($D_2O$, 300 MHz) 7.424 (s, 1H), 7.120–6.974 (m, 5H), 5.998 (t, J=6.7 Hz, 1H), 4.153 (m, 1H), 3.843 (m, 1H), 3.728 (m, 1H), 3.585 (m, 2H), 3.491 (s, 3H), 2.794 (m, 1H), 2.699 (m, 1H), 2.219 (m, 1H), 2.116 (m, 1H), 1.675 (s, 3H); $^{31}P$ NMR ($D_2O$, 121 MHz) 6.370; HRMS (FAB m/z calcd for $C_{13}H_{20}N_6O_8P$ $(M+H)^+$ 419.1080, found 419.1103.

EXAMPLE 25

3-Azido-3-deoxythymidine-5-methoxy-L-trytophanyl-phosphoramidate (9)

Compound 40 (218 mg, 0.503 mmol) and tryptophan methyl ester (HCl salt, 258 mg, 1.01 mmol) were subjected to a procedure similar to that described in Example 6. Flash chromatography (SiO$_2$, 5:2:0.25 CHCl$_3$/MeOH/H$_2$O containing 0.5% conc. NH$_4$OH) gave the title compound (198 mg, 70%) as a white solid. $^1$H NMR (D$_2$O, 300 MHz) 7.222 (d, J=7.9 Hz, 1H), 7.103 (d, J=8.1 Hz, 1H), 7.072 (s, 1H), 6.880 (s, 1H), 6.857 (t, J=7.7 Hz, 1H), 6.729 (t, J=7.5 Hz, 1H), 5.690 (t, J=6.6 Hz, 1H), 3.883 (m, 1H), 3.763 (m, 1H), 3.635 (m, 1H), 3.527 (m, 2H), 3.448 (s, 3H), 2.899 (m, 1H), 2.765 (m, 1H), 1.857 (m, 1H), 1.682 (m, 1H), 1.493 (s, 3H); $^{31}$P NMR (D$_2$O, 121 MHz) 6.412; HRMS (FAB) m/z calcd for C$_{13}$H$_{20}$N$_6$O$_8$P (M+H)$^+$ 419.1080, found 419.1103.

EXAMPLE 26

3-Azido-3-deoxythymidine-5-methoxy-D-phenylalaninylphosphoramidate (12)

Compound 40 (340 mg, 0.785 mmol) and D-phenylalanine methyl ester (HCl salt, 339 mg, 1.57 mmol) were subjected to a procedure similar to that described in Example 6. Flash chromatography (SiO$_2$, 5:2:0.25 CHCl$_3$/MeOH/H$_2$O containing 0.5% conc. NH$_4$OH) gave the title compound (282 mg, 68%) as a white solid. $^1$H NMR (D$_2$O, 300 MHz) 7.415 (s, 1H), 7.1580–6.998 (m, 5H), 5.995 (t, J=6.8 Hz, 1H), 4.118 (m, 1H), 3.808 (m, 1H), 3.738 (m, 1H), 3.661 (m, 1H), 3.467 (m, 1H), 3.403 (s, 3H), 2.754 (m, 2H), 2.212 (m, 2H), 1.679 (s, 3H); $^{31}$P NMR (D$_2$O, 121 MHz) 6.204; HRMS (FAB) m/z calcd for C$_{13}$H$_{20}$N$_6$O$_8$P (M+H)$^+$ 419.1080, found 419.1103.

EXAMPLE 27

3-Azido-3-deoxythymidine-5-methoxy-D-trytophanyl-phosphoramidate (10)

Compound 40 (312 mg, 0.721 mmol) and D-tryptophan methyl ester (HCl salt, 367 mg, 1.44 mmol) were subjected to a procedure similar to that described in Example 6. Flash chromatography (SiO$_2$, 5:2:0.25 CHCl$_3$/MeOH/H$_2$O containing 0.5% conc. NH$_4$OH) gave the title compound (256 mg, 63%) as a white solid. $^1$H NMR (D$_2$O, 300 MHz) 7.299 (d, J=7.9 Hz, 1H), 7.182 (d, J=8.1 Hz, 1H), 7.141 (s, 1H), 6.939 (s, 1H), 6.930 (dd, J=7.0, 8.1 Hz, 1H), 6.816 (t, J=7.0 7.9 Hz, 1H), 5.773 (t, J=6.8 Hz, 1H), 3.851–3.741 (m, 2H), 3.691 (m, 1H), 3.605 (m, 1H), 3.357 (s, 3H), 3.332 (m, 1H), 2.882 (m, 2H), 2.002 (m, 1H), 1.815 (m, 1H), 1.504 (s, 3H); $^{31}$P NMR (D$_2$O, 121 MHz) 6.396; HRMS (FAB) m/z calcd for C$_{13}$H$_{20}$N$_6$O$_8$P (M+H)$^+$ 419.1080, found 419.1103.

EXAMPLE 28

Using procedures similar to those described by T. W. Abraham, et al. *J. Med. Chem.*, 1996, 39, 4569–4575 the following compounds of formula VII were prepared:

5-fluoro-2'deoxy-5'-uridyl N-((L)-1-carbomethoxy-2-phenylethyl)phosphoramidate (36);

5-fluoro-2'deoxy-5'-uridyl N-((L)-1-carbomethoxy-2-indol-3-ylethyl)phosphoramidate (37)

5-fluoro-2'deoxy-5'-uridyl N-((D)-1-carbomethoxy-2-phenylethyl)phosphoramidate (38); and 5-fluoro-2'deoxy-5'-uridyl N-((D)-1-carbomethoxy-2-phenylethyl)phosphoramidate (39)

EXAMPLE 29

The following illustrate representative pharmaceutical dosage forms, containing a compound of formula I formula II, or formula V ('Compound X'), for therapeutic or prophylactic use in humans.

| (i) Tablet 1 | mg/tablet |
|---|---|
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |
| (ii) Tablet 2 | mg/tablet |
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |
| (iii) Capsule | mg/capsule |
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |
| (iv) Injection 1 (1 mg/ml) | mg/ml |
| 'Compound X' (free acid form) | 1.0 |
| Dibasic sodium phosphate | 12.0 |
| Monobasic sodium phosphate | 0.7 |
| Sodium chloride | 4.5 |
| 1.0 N Sodium hydroxide solution (pH adjustment to 7.0–7.5) | q.s. |
| Water for injection | q.s. ad 1 mL |
| (v) Injection 2 (10 mg/ml) | mg/ml |
| 'Compound X' (free acid form) | 10.0 |
| Monobasic sodium phosphate | 0.3 |
| Dibasic sodium phosphate | 1.1 |
| Polyethylene glycol 400 | 200.0 |
| 01 N Sodium hydroxide solution (pH adjustment to 7.0–7.5) | q.s. |
| Water for injection | q.s. ad 1 mL |
| (vi) Aerosol | mg/can |
| 'Compound X' | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A therapeutic method comprising inhibiting cancer cell growth by administering to a mammal in need of such therapy, an effective amount of a compound of formula V:

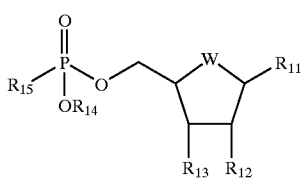

V

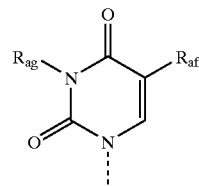

VI wherein
- $R_{11}$ is adenine, guanine, cytosine, thymine, 3-deazaadenine, or uracil, optionally substituted by 1, 2, or 3 U; wherein each U is independently halo, hydroxy, $(C_1-C_6)$alkyl, $(C_3-C_6)$cycloalkyl, $(C_1-C_6)$alkoxy, $(C_3-C_6)$cycloalkyloxy, $(C_1-C_6)$alkanoyl, $(C_1-C_6)$alkanoyloxy, trifluoromethyl, hydroxy$(C_1-C_6)$alkyl, $-(CH_2)_{1-4}P(=O)(OR_k)_2$, aryl, aryl$(C_1-C_6)$alkyl, or $NR_xR_y$;
- one or $R_{12}$ and $R_{13}$ is azido and the other is hydrogen, halo, hydroxy, $(C_1-C_6)$alkyl, $(C_3-C_6)$cycloalkyl, $(C_1-C_6)$alkoxy, $(C_3-C_6)$cycloalkyloxy, $(C_1-C_6)$alkanoyl, $(C_1-C_6)$alkanoyloxy, trifluoromethyl, azido, cyano, $-N(R_z)C(=O)N(R_{aa})(R_{ab})$, $-N(R_z)C(=O)OR_{ac}$, or $NR_{ad}R_{ae}$
- $R_{14}$ is hydrogen, $(C_1-C_6)$alkyl, $(C_3-C_6)$cycloalkyl, aryl, aryl$(C_1-C_6)$alkyl, or 2-cyanoethyl, wherein any aryl ring may optionally be substituted by 1, 2, or 3 halo, hydroxy, $(C_1-C_6)$alkyl, $(C_3-C_6)$cycloalkyl, $(C_1-C_6)$alkoxy, $(C_3-C_6)$cycloalkyloxy, $(C_1-C_6)$alkanoyl, $(C_1-C_6)$alkanoyloxy, trifluoromethyl, trifluoromethoxy, nitro, cyano, or amino;
- $R_{15}$ is an amino acid or a peptide;
- W is oxy, thio, or methylene;
- each $R_v$ is independently hydrogen or $(C_1-C_6)$alkyl;
- $R_x$ and $R_y$ are each independently hydrogen, $(C_1-C_6)$alkyl, $(C_3-C_6)$cycloalkyl, phenyl, benzyl, phenethyl, or $(C_1-C_6)$alkanoyl; or $R_x$ and $R_y$ together with the nitrogen to which they are attached are pyrrolidino, piperidino or morpholino;
- $R_z$ is hydrogen, $(C_1-C_6)$alkyl, $(C_3-C_6)$cycloalkyl, phenyl, benzyl, or phenethyl;
- $R_{aa}$ and $R_{ab}$ are each independently hydrogen, $(C_1-C_6)$alkyl, $(C_3-C_6)$cycloalkyl, phenyl, benzyl, or phenethyl; or $R_{aa}$ and $R_{ab}$ together with the nitrogen to which they are attached are pyrrolidino, piperidino or morpholino; and
- $R_{ac}$ is hydrogen, $(C_1-C_6)$alkyl, $(C_3-C_6)$cycloalkyl, phenyl, benzyl, or phenethyl; and
- $R_{ad}$ and $R_{ae}$ are each independently hydrogen, $(C_1-C_6)$alkyl, $(C_3-C_6)$cycloalkyl, phenyl, benzyl, phenethyl, or $(C_1-C_6)$alkanoyl; or $R_{ad}$ and $R_{ae}$ together with the nitrogen to which they are attached are pyrrolidino, piperidino or morpholino;
or a pharmaceutically acceptable salt thereof.

2. The method of claim 1 wherein $R_{11}$ is adenine, guanine, cytosine, thymine, or uracil, optionally substituted by 1, 2, or 3 U; wherein each U is independently halo, hydroxy, $(C_1-C_6)$alkyl, $(C_3-C_6)$cycloalkyl, $(C_1-C_6)$alkoxy, $(C_3-C_6)$cycloalkyloxy, $(C_1-C_6)$alkanoyl, $(C_1-C_6)$alkanoyloxy, trifluoromethyl, hydroxy$(C_1-C_6)$alkyl, $-(CH_2)_{1-4}P(=O)(OR_k)_2$, aryl, aryl$(C_1-C_6)$alkyl, or $NR_xR_y$.

3. The method of claim 1 wherein $R_{11}$ is a nitrogen linked radical of formula VI:

wherein $R_{af}$ is hydrogen, halo, $(C_1-C_6)$alkyl, $(C_3-C_6)$cycloalkyl, or trifluoromethyl; and $R_{ag}$ is hydrogen, $(C_1-C_6)$alkyl, $(C_3-C_6)$cycloalkyl, trifluoromethyl, hydroxy$(C_1-C_6)$alkyl, or $-(CH_2)_{1-4}P(=O)(OR_w)_2$.

4. The method of claim 1 wherein $R_{12}$ is azido.
5. The method of claim 1 wherein $R_{13}$ is azido.
6. The method of claim 1 wherein $R_{15}$ is an amino acid.
7. The method of claim 1 wherein $R_{15}$ is a peptide.
8. The method of claim 5 wherein $R_{11}$ is thymine; $R_{12}$ is hydrogen; $R_{14}$ is hydrogen; $R_{15}$ in N-linked phenylalanine; and W is oxy; or a pharmaceutically acceptable salt thereof.
9. The method of claim 1 wherein $R_{15}$ is a nitrogen linked radical of formula III:

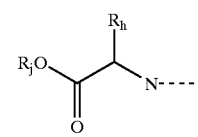

III wherein $R_h$ is hydrogen, $(C_1-C_6)$alkyl, $(C_3-C_6)$cycloalkyl, $(C_3-C_6)$cycloalkyl$(C_1-C_6)$alkyl, $(C_1-C_6)$alkyl-S—$(C_1-C_6)$alkyl-, aryl, heteroaryl, aryl$(C_1-C_6)$alkyl, or heteroaryl$(C_1-C_6)$alkyl; wherein any aryl or heteroaryl may optionally be substituted with 1, 2, or 3 Z; $R_j$ is hydrogen, $(C_1-C_6)$alkyl, phenyl, benzyl, or phenethyl; and wherein each Z is independently halo, hydroxy, $(C_1-C_6)$alkyl, $(C_3-C_6)$cycloalkyl, $(C_1-C_6)$alkoxy, $(C_3-C_6)$cycloalkyloxy, $(C_1-C_6)$alkanoyl, $(C_1-C_6)$alkanoyloxy, trifluoromethyl, trifluoromethoxy, nitro, cyano, or amino.

10. The method of claim 1 wherein $R_{15}$ is a nitrogen linked radical of formula VI:

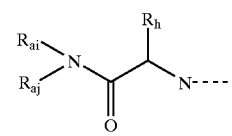

VI wherein $R_{ah}$ is hydrogen, $(C_1-C_6)$alkyl, $(C_3-C_6)$cycloalkyl, $(C_3-C_6)$cycloalkyl$(C_1-C_6)$alkyl, $(C_1-C_6)$alkyl-S—$(C_1-C_6)$alkyl-, aryl, heteroaryl, aryl$(C_1-C_6)$alkyl, or heteroaryl$(C_1-C_6)$alkyl; wherein any aryl or heteroaryl may optionally be substituted with 1, 2, or 3 Z; $R_{ai}$ and $R_{aj}$ are each independently hydrogen, $(C_1-C_6)$alkyl, $(C_3-C_6)$cycloalkyl, $(C_3-C_6)$cycloalkyl$(C_1-C_6)$alkyl, phenyl, benzyl, or phenethyl; and each Z is independently halo, hydroxy, $(C_1-C_6)$alkyl, $(C_3-C_6)$cycloalkyloxy, $(C_1-C_6)$alkoxy, $(C_3-C_6)$cycloalkyloxy, $(C_1-C_6)$alkanoyl, $(C_1-C_6)$alkanoyloxy, trifluoromethyl, trifluoromethoxy, nitro, cyano, or amino.

11. The method of claim 10 wherein $R_{ah}$ is hydrogen, $(C_1-C_6)$alkyl, aryl, heteroaryl, aryl$(C_1-C_6)$alkyl, or heteroaryl$(C_1-C_6)$alkyl; wherein any aryl or heteroaryl may optionally be substituted with 1, 2, or 3 Z.

12. The method of claim 10 wherein $R_{ah}$ is hydrogen, $(C_1-C_6)$alkyl, phenylmethyl, or 3-indolylmethyl.

13. The method of claim 10 wherein $R_{ah}$ is phenylmethyl.

14. The method of claim 10 wherein $R_{ah}$ is 3-indolylmethyl.

15. The method of claim 10 wherein $R_{ai}$ and $R_{aj}$ are each independently hydrogen, $(C_1-C_6)$alkyl, or $(C_3-C_6)$ cycloalkyl.

16. The method of claim 10 wherein $R_{ai}$ is hydrogen and $R_{aj}$ is methyl, cyclopropyl, or cyclohexyl.

17. The method of claim 10 wherein the carbon bearing $R_{ah}$ has the (S) absolute configuration.

18. The method of claim 10 wherein the carbon bearing $R_{ah}$ has the (R) absolute configuration.

19. A composition of matter comprising compound of formula V:

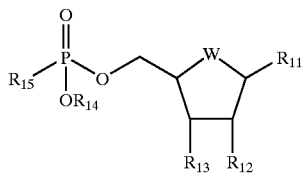

wherein $R_{11}$ is adenine, guanine, cytosine, thymine, or uracil, optionally substituted by 1, 2, or 3 U; wherein each U is independently halo, hydroxy, $(C_1-C_6)$alkyl, $(C_3-C_6)$ cycloalkyl, $(C_1-C_6)$alkoxy, $(C_3-C_6)$cycloalkyloxy, $(C_1-C_6)$alkanoyl, $(C_1-C_6)$alkanoyloxy, trifluoromethyl, hydroxy$(C_1-C_6)$alkyl, $-(CH_2)_{1-4}P(=O)(OR_w)_2$, aryl, aryl$(C_1-C_6)$alkyl, or $NR_xR_y$;

one of $R_{12}$ and $R_{13}$ is azido and the other is hydrogen, halo, hydroxy, $(C_1-C_6)$alkyl, $(C_3-C_6)$cycloalkyl, $(C_1-C_6)$alkoxy, $(C_3-C_6)$cycloalkyloxy, $(C_1-C_6)$ alkanoyl, $(C_1-C_6)$alkanoyloxy, trifluoromethyl, azido, cyano, $-N(R_z)C(=O)N(R_{aa})(R_{ab})$, $-N(R_z)C(=O)OR_{ac}$, or $NR_{ad}R_{ae}$;

$R_{14}$ is hydrogen, $(C_1-C_6)$alkyl, $(C_3-C_6)$cycloalkyl, aryl, aryl$(C_1-C_6)$alkyl, or 2-cyanoethyl, wherein any aryl ring may optionally be substituted by 1, 2, or 3 halo, hydroxy, $(C_1-C_6)$alkyl, $(C_3-C_6)$cycloalkyl, $(C_1-C_6)$ alkoxy, $(C_3-C_6)$cycloalkyloxy, $(C_1-C_6)$alkanoyl, $(C_1-C_6)$alkanoyloxy, trifluoromethyl, trifluoromethoxy, nitro, cyano, or amino;

$R_{15}$ is an amino acid or a peptide;

W is oxy, thio, or methylene;

each $R_w$ is independently hydrogen or $(C_1-C_6)$alkyl;

$R_x$ and $R_y$ are each independently hydrogen, $(C_1-C_6)$ alkyl, $(C_3-C_6)$cycloalkyl, phenyl, benzyl, phenethyl, or $(C_1-C_6)$alkanoyl; or $R_x$ and $R_y$ together with the nitrogen to which they are attached are pyrrolidino, piperidino or morpholino;

$R_z$ is hydrogen, $(C_1-C_6)$alkyl, $(C_3-C_6)$cycloalkyl, phenyl, benzyl, or phenethyl;

$R_{aa}$ and $R_{ab}$ are each independently hydrogen, $(C_1-C_6)$ alkyl, $(C_3-C_6)$cycloalkyl, phenyl, benzyl, or phenethyl; or $R_{aa}$ and $R_{ab}$ together with the nitrogen to which they are attached are pyrrolidino, piperidino or morpholino; and $R_{ac}$ is hydrogen, $(C_1-C_6)$alkyl, $(C_3-C_6)$cycloalkyl, phenyl, benzyl, or phenethyl; and $R_{ad}$ and $R_{ae}$ are each independently hydrogen, $(C_1-C_6)$ alkyl, $(C_3-C_6)$cycloalkyl, phenyl, benzyl, phenethyl, or $(C_1-C_6)$alkanoyl; or $R_{ad}$ and $R_{ae}$ together with the nitrogen to which they are attached are pyrrolidino, piperidino or morpholino;

or a pharmaceutically acceptable salt thereof;

linked to a reagent that is capable of targeting the compound to a tumor or cancer cell; wherein the reagent is a peptide, polyclonal antibody, or monoclonal antibody.

20. A compound of formula I:

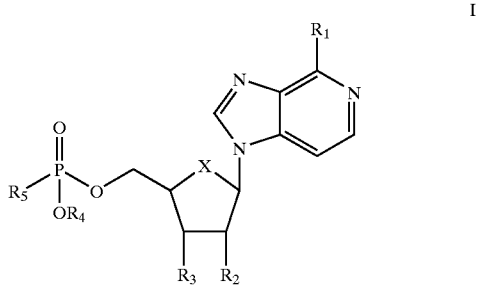

wherein $R_1$ is hydrogen, halo, hydroxy, $(C_1-C_6)$alkyl, $(C_3-C_6)$ cycloalkyl, $(C_1-C_6)$alkoxy, $(C_3-C_6)$cycloalkyloxy, $(C_1-C_6)$alkanoyl, $(C_1-C_6)$alkanoyloxy, trifluoromethyl, or $NR_aR_b$;

$R_2$ and $R_3$ are each independently hydrogen, halo, hydroxy, $(C_1-C_6)$alkyl, $(C_3-C_6)$cycloalkyl, $(C_1-C_6)$ alkoxy, $(C_3-C_6)$cycloalkyloxy, $(C_1-C_6)$alkanoyl, $(C_1-C_6)$alkanoyloxy, trifluoromethyl, azido, cyano, or $NR_cR_d$;

$R_4$ is hydrogen, $(C_1-C_6)$alkyl, $(C_3-C_6)$cycloalkyl, aryl, aryl$(C_1-C_6)$alkyl, or 2-cyanoethyl, wherein any aryl ring may optionally be substituted with 1, 2, or 3 halo, hydroxy, $(C_1-C_6)$alkyl, $(C_3-C_6)$cycloalkyl, $(C_1-C_6)$ alkoxy, $(C_3-C_6)$cycloalkyloxy, $(C_1-C_6)$alkanoyl, $(C_1-C_6)$alkanoyloxy, trifluoromethyl, trifluoromethoxy, nitro, cyano, or amino;

$R_5$ is an amino acid or a peptide;

X is oxy, thio, or methylene;

$R_a$ and $R_b$ are each independently hydrogen, $(C_1-C_6)$ alkyl, $(C_3-C_6)$cycloalkyl, phenyl, benzyl, phenethyl, or $(C_1-C_6)$alkanoyl; or $R_a$ and $R_b$ together with the nitrogen to which they are attached are pyrrolidino, piperidino or morpholino;

$R_c$ and $R_d$ are each independently hydrogen, $(C_1-C_6)$ alkyl, $(C_3-C_6)$cycloalkyl, phenyl, benzyl, phenethyl, $(C_1-C_6)$alkanoyl, $-C(=O)N(R_e)(R_f)$, or $-C(=O)$ $OR_g$; or $R_c$ and $R_d$ together with the nitrogen to which they are attached are pyrrolidino, piperidino or morpholino;

$R_e$ and $R_f$ are each independently hydrogen, $(C_1-C_6)$ alkyl, $(C_3-C_6)$cycloalkyl, phenyl, benzyl, or phenethyl; or $R_e$ and $R_f$ together with the nitrogen to which they are attached are pyrrolidino, piperidino or morpholino; and $R_g$ is hydrogen, $(C_1-C_6)$alkyl, $(C_3-C_6)$cycloalkyl, phenyl, benzyl, or phenethyl;

or a pharmaceutically acceptable salt thereof.

21. The compound of claim 20 wherein $R_1$ is hydrogen or $NR_aR_b$.

22. The compound of claim 20 wherein $R_2$ and $R_3$ are each independently hydrogen, hydroxy, azido or $NR_cR_d$.

23. The compound of claim 20 wherein $R_2$ is hydrogen.

24. The compound of claim 20 wherein $R_2$ is halo, hydroxy, $(C_1-C_6)$alkanoyl, trifluoromethyl, azido, cyano, or $NR_cR_d$.

25. The compound of claim 20 wherein $R_2$ is azido.
26. The compound of claim 20 wherein $R_2$ is $NR_cR_d$.
27. The compound of claim 20 wherein $R_3$ is hydrogen.
28. The compound of claim 20 wherein $R_3$ is halo, hydroxy, $(C_1-C_6)$alkanoyl, trifluoromethyl, azido, cyano, or $NR_cR_d$.
29. The compound of claim 20 wherein $R_3$ is azido.
30. The compound of claim 20 wherein $R_3$ is $NR_cR_d$.
31. The compound of claim 20 wherein $R_4$ is hydrogen.
32. The compound of claim 20 wherein $R_5$ is an amino acid.
33. The compound of claim 20 wherein X is oxy.
34. The compound of claim 20 wherein X is thio.
35. The compound of claim 20 wherein X is methylene.
36. The compound of claim 20 wherein $R_a$ and $R_b$ are each hydrogen.
37. The compound of claim 20 wherein $R_c$ and $R_d$ are each hydrogen.
38. The compound of claim 20 wherein $R_2$ $NR_cR_d$; $R_5$ is hydrogen; $R_c$ is $-C(=O)N(R_a)(R_f)$; and $R_d$ is hydrogen.
39. The compound of claim 20 wherein $R_2$ is hydrogen; $R_3$ is $NR_cR_d$; $R_c$ is $-C(=O)N(R_e)(R_f)$; and $R_d$ is hydrogen.
40. The compound of claim 26 wherein $R_3$ is hydrogen; and $R_e$ is $-C(=O)OR_g$.
41. The compound of claim 30 wherein $R_2$ is hydrogen; and $R_c$ is $-C(=O)OR_g$.
42. The compound of claim 20 wherein $R_5$ is a nitrogen linked radical of formula III:

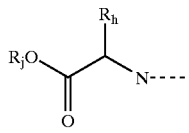

III wherein $R_h$ is hydrogen, $(C_1-C_6)$alkyl, $(C_3-C_6)$cycloalkyl, $(C_3-C_6)$cycloalkyl$(C_1-C_6)$alkyl, $(C_1-C_6)$alkyl-S—$(C_1-C_6)$alkyl-, aryl, heteroaryl, aryl$(C_1-C_6)$alkyl, or heteroaryl$(C_1-C_6)$alkyl; wherein any aryl or heteroaryl may optionally be substituted with 1, 2 or 3 Z; $R_j$ is hydrogen, $(C_1-C_6)$alkyl, phenyl, benzyl, or phenethyl; and wherein each Z is independently halo, hydroxy, $(C_1-C_6)$alkyl, $(C_3-C_6)$cycloalkyl, $(C_1-C_6)$alkoxy, $(C_3-C_6)$cycloalkyloxy, $(C_1-C_6)$alkanoyl, $(C_1-C_6)$alkanoyloxy, trifluoromethyl, trifluoromethoxy, nitro, cyano, or amino.

43. The compound of claim 20 wherein $R^5$ is nitrogen-linked radical of formula VI:

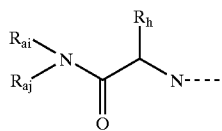

VI wherein $R_{ah}$ is hydrogen, $(C_1-C_6)$alkyl, $(C_3-C_6)$cycloalkyl, $(C_3-C_6)$cycloalkyl$(C_1-C_6)$alkyl, $(C_1-C_6)$alkyl-S—$(C_1-C_6)$alkyl-, aryl, heteroaryl, aryl$(C_1-C_6)$alkyl, or heteroaryl$(C_1-C_6)$alkyl; wherein any aryl or heteroaryl may optionally be substituted with 1, 2 or 3 Z; $R_{ai}$ and $R_{aj}$ are each independently hydrogen, $(C_1-C_6)$alkyl, $(C_3-C_6)$cycloalkyl, $(C_3-C_6)$cycloalkyl$(C_1-C_6)$alkyl, phenyl, benzyl, or phenethyl; and each Z is independently halo, hydroxy, $(C_1-C_6)$alkyl, $(C_3-C_6)$cycloalkyl, $(C_1-C_6)$alkoxy, $(C_3-C_6)$cycloalkyloxy, $(C_1-C_6)$alkanoyl, $(C_1-C_6)$alkanoyloxy, trifluoromethyl, trifluoromethoxy, nitro, cyano, or amino.

44. The compound of claim 43 wherein $R_{ah}$ is hydrogen, $(C_1-C_6)$alkyl, aryl, heteroaryl, aryl$(C_1-C_6)$alkyl, or heteroaryl$(C_1-C_6)$alkyl; wherein any aryl or heteroaryl may optionally be substituted with 1, 2, or 3 Z.
45. The compound of claim 43 wherein $R_{ah}$ is hydrogen, $(C_1-C_6)$alkyl, phenylmethyl, or 3-indolylmethyl.
46. The compound of claim 43 wherein $R_{ah}$ is phenylmethyl.
47. The compound of claim 43 wherein $R_{ah}$ is 3-indolylmethyl.
48. The compound of claim 43 wherein $R_{ai}$ and $R_{aj}$ are each independently hydrogen, $(C_1-C_6)$alkyl, or $(C_3-C_6)$cycloalkyl.
49. The compound of claim 43 wherein $R_{ai}$ is hydrogen and $R_{aj}$ is methyl, cyclopropyl, or cyclohexyl.
50. The compound of claim 43 wherein the carbon bearing $R_{ah}$ has the (S) absolute configuration.
51. The compound of claim 43 wherein the carbon bearing $R_{ah}$ has the (R) absolute configuration.
52. The compound of claim 42 wherein the carbon bearing $R_h$ has the (S) configuration.
53. The compound of formula II:

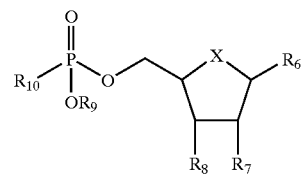

II wherein $R_6$ is adenine, guanine, cytosine, thymine, 3-deazaadenine, or uracil, optionally substituted by 1, 2, or 3 Y; wherein each Y is independently halo, hydroxy, $(C_1-C_6)$alkyl, $(C_3-C_6)$cycloalkyl, $(C_1-C_6)$alkoxy, $(C_3-C_6)$cycloalkyloxy, $(C_1-C_6)$alkanoyl, $(C_1-C_6)$alkanoyloxy, trifluoromethyl, hydroxy$(C_1-C_6)$alkyl, $-(CH_2)_{1-4}P(=O)(OR_k)_2$, aryl, aryl$(C_1-C_6)$alkyl, or $NR_mR_n$, and wherein any aryl ring may optionally be substituted with 1, 2, or 3 halo, hydroxy, $(C_1-C_6)$alkyl, $(C_3-C_6)$cycloalkyl, $(C_1-C_6)$alkoxy, $(C_3-C_6)$cycloalkyloxy, $(C_1-C_6)$alkanoyl, $(C_1-C_6)$alkanoyloxy, trifluoromethyl, trifluoromethoxy, nitro, cyano, or amino one of $R_7$ and $R_8$ is $-N(R_b)C(=O)N(R_p)(R_q)$, or $N(R_o)C(=O)OR_r$, and the other is hydrogen, halo, hydroxy, $(C_1-C_6)$alkyl, $(C_3-C_6)$cycloalkyl, $(C_1-C_6)$alkoxy, $(C_3-C_6)$cycloalkyloxy, $(C_1-C_6)$alkanoyl, $(C_1-C_6)$alkanoyloxy, trifluoromethyl, azido, cyano, or $NR_aR_c$ $R_9$ is hydrogen, $(C_1-C_6)$alkyl, $(C_3-C_6)$cycloalkyl, aryl, aryl$(C_1-C_6)$alkyl, or 2-cyanoethyl, wherein any aryl ring may optionally be substituted by 1, 2, or 3 halo, hydroxy, $(C_1-C_6)$alkyl, $(C_3-C_6)$cycloalkyl, $(C_1-C_6)$alkoxy, $(C_3-C_6)$cycloalkyloxy, $(C_1-C_6)$alkanoyl, $(C_1-C_6)$alkanoyloxy, trifluoromethyl, trifluoromethoxy, nitro, cyano, or amino;

$R_{10}$ is an amino acid or a peptide;

X is oxy, thio, or methylene;

each $R_k$ is independently hydrogen or $(C_1-C_6)$alkyl;

$R_m$ and $R_n$ are each independently hydrogen, $(C_1-C_6)$alkyl, $(C_3-C_6)$cycloalkyl, phenyl, benzyl, phenethyl, or $(C_1-C_6)$alkanoyl; or $R_m$ and $R_n$ together with the nitrogen to which they are attached are pyrrolidino, piperidino or morpholino;

$R_o$ is hydrogen, $(C_1-C_6)$alkyl, $(C_3-C_6)$cycloalkyl, phenyl, benzyl, or phenethyl;

$R_p$ and $R_q$ are each independently hydrogen, $(C_1-C_6)$alkyl, $(C_3-C_6)$cycloalkyl, phenyl, benzyl, or phenethyl; or $R_p$ and $R_q$ together with the nitrogen to which they are attached are pyrrolidino, piperidino or morpholino; and $R_r$ is hydrogen, $(C_1-C_6)$alkyl, $(C_3-C_6)$cycloalkyl, phenyl, benzyl, or phenethyl; and $R_s$ and $R_t$ are each independently hydrogen, $(C_1-C_6)$alkyl, $(C_3-C_6)$cycloalkyl, phenyl, benzyl, phenethyl, or $(C_1-C_6)$alkanoyl; or $R_s$ and $R_t$ together with the nitrogen to which they are attached are pyrrolidino, piperidino or morpholino;

or a pharmaceutically acceptable salt thereof.

54. The compound of claim 53 wherein $R_6$ is adenine, guanine, cytosine, thymine, or uracil, optionally substituted by 1, 2, or 3 Y; wherein each Y is independently halo, hydroxy, $(C_1-C_6)$alkyl, $(C_3-C_6)$cycloalkyl, $(C_1-C_6)$alkoxy, $(C_3-C_6)$cycloalkyloxy, $(C_1-C_6)$alkanoyl, $(C_1-C_6)$alkanoyloxy, trifluoromethyl, hydroxy$(C_1-C_6)$alkyl, $-(CH_2)_{1-4}P(=O)(OR_k)_2$, aryl, aryl$(C_1-C_6)$alkyl, or $NR_mR_n$, and wherein any aryl ring may optionally be substituted with 1, 2, or 3 halo, hydroxy, $(C_1-C_6)$alkyl, $(C_3-C_6)$cycloalkyl, $(C_1-C_6)$alkoxy, $(C_3-C_6)$cycloalkyloxy, $(C_1-C_6)$alkanoyl, $(C_1-C_6)$alkanoyloxy, trifluoromethyl, trifluoromethyl, nitro, cyano, or amino.

55. The compound of claim 53 wherein $R_6$ is a nitrogen linked radical of formula IV:

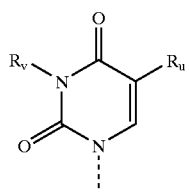

IV wherein $R_u$ is hydrogen, halo, $(C_1-C_6)$alkyl, $(C_3-C_6)$cycloalkyl, or trifluoromethyl; and $R_v$ is hydrogen, $(C_1-C_6)$alkyl, $(C_3-C_6)$cycloalkyl, trifluoromethyl, hydroxy$(C_1-C_6)$alkyl, or $-(CH_2)(C_1-C_6)$, or $-(CH_2)_{1-4}P(=O)(OR_k)_2$.

56. The compound of claim 53 wherein one of $R_7$ and $R_8$ is $-N(R_nC(=O)N(R_p)(R_q)$.

57. The compound of claim 53 wherein $R_7$ is $-N(R_oC(=O)N(R_p)(R_q)$.

58. The compound of claim 53 wherein $R_8$ is $-N(R_oC(=O)N(R_p)(R_q)$.

59. The compound of claim 58 wherein $R_{10}$ is an amino acid.

60. The compound of claim 58 wherein $R_{10}$ is a peptide.

61. The compound of claim 53 wherein $R_{10}$ is a nitrogen linked radical of formula III:

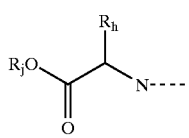

III wherein $R_h$ is hydrogen, $(C_1-C_6)$alkyl, $(C_3-C_6)$cycloalkyl, $(C_3-C_6)$cycloalkyl$(C_1-C_6)$alkyl, $(C_1-C_6)$alkyl-S—$(C_1-C_6)$alkyl-, aryl, heteroaryl, aryl$(C_1-C_6)$alkyl, or heteroaryl $(C_1-C_6)$alkyl; wherein any aryl or heteroaryl may optionally be substituted with 1, 2 or 3 Z; $R_j$ is hydrogen, $(C_1-C_6)$alkyl, phenyl, benzyl, or phenethyl; and wherein each Z is independently halo, hydroxy, $(C_1-C_6)$alkyl, $(C_3-C_6)$cycloalkyl, $(C_1-C_6)$alkoxy, $(C_3-C_6)$cycloalkyloxy, $(C_1-C_6)$alkanoyl, $(C_1-C_6)$alkanoyloxy, trifluoromethyl, trifluoromethoxy, nitro, cyano, or amino.

62. The compound of claim 53 wherein $R_{10}$ is a nitrogen linked radical of formula VI:

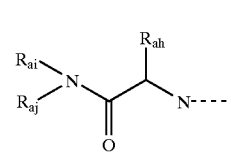

VI wherein $R_{ah}$ is hydrogen, $(C_1-C_6)$alkyl, $(C_3-C_6)$cycloalkyl, $(C_3-C_6)$cycloalkyl$(C_1-C_6)$alkyl, $(C_1-C_6)$alkyl-S—$(C_1-C_6)$alkyl-, aryl, heteroaryl, aryl$(C_1-C_6)$alkyl, or heteroaryl $(C_1-C_6)$alkyl; wherein any aryl or heteroaryl may optionally be substituted with 1, 2 or 3 Z; $R_{ai}$ and $R_{aj}$ are each independently hydrogen, $(C_1-C_6)$alkyl, $(C_3-C_6)$cycloalkyl, $(C_3-C_6)$cycloalkyl$(C_1-C_6)$alkyl, phenyl, benzyl, or phenethyl; and each Z is independently halo, hydroxy, $(C_1-C_6)$alkyl, $(C_3-C_6)$cycloalkyl, $(C_1-C_6)$alkoxy, $(C_3-C_6)$cycloalkyloxy, $(C_1-C_6)$alkanoyl, $(C_1-C_6)$alkanoyloxy, trifluoromethyl, trifluoromethoxy, nitro, cyano, or amino.

63. The compound of claim 62 wherein $R_{ah}$ is hydrogen, $(C_1-C_6)$alkyl, aryl, heteroaryl, aryl$(C_1-C_6)$alkyl, or heteroaryl$(C_1-C_6)$alkyl; wherein any aryl or heteroaryl may optionally be substituted with 1, 2, or 3 Z.

64. The compound of claim 62 wherein $R_{ah}$ is hydrogen, $(C_1-C_6)$alkyl, phenylmethyl, or 3-indolylmethyl.

65. The compound of claim 62 wherein $R_{ah}$ is phenylmethyl.

66. The compound of claim 62 wherein $R_{ah}$ is 3-indolylmethyl.

67. The compound of claim 62 wherein $R_{af}$ and $R_{aj}$ are each independently hydrogen, $(C_1-C_6)$alkyl, or $(C_3-C_6)$cycloalkyl.

68. The compound of claim 62 wherein $R_{ai}$ is hydrogen, and $R_{aj}$ is methyl, cyclopropyl, or cyclohexyl.

69. The compound of claim 62 wherein the carbon bearing $R_{ah}$ has the (S) absolute configuration.

70. The compound of claim 62 wherein the carbon bearing $R_{ah}$ has the (R) absolute configuration.

71. A pharmaceutical composition comprising a compound of claim 20 or 53; in combination with a pharmaceutically acceptable diluent or carrier.

72. A therapeutic method comprising preventing or treating a viral infection in a mammal by administering to the mammal, an effective amount of a compound of claim 20 or 53.

73. A composition of matter comprising a compound of claim 20 or 53, and a reagent that is capable of targeting the compound to a virus.

74. The compound 3-deaza adenosine-5'-N-(1-carbomethoxy-2-phenylethyl)phosphoramidate; 3-deaza adenosine-5'-N-(1-carbomethoxy-2-indolylethyl) phosphoramidate; 3-deaza aristeromycin-5'-N-(1-carbomethoxy-2-phenylethyl)phosphoramidate; 3-deaza adenosine-5'-N-(1-methylaminocarbonyl-2-phenylethyl) phosphoramidate; or 3-deaza adenosine-5'-N-[1-methylamino-carbonyl-2-(3-indolyl)ethyl] phosphoramidate; or a pharmaceutically acceptable salt thereof.

75. A therapeutic method comprising treating breast cancer by administering to a mammal in need of such therapy, an effective amount of a compound of formula VII:

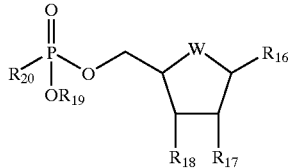

VII wherein $R_{16}$ is adenine, guanine, cytosine, thymine, 3-deazaadenine, or uracil, optionally substituted by 1, 2, or 3 U; wherein each U is independently halo, hydroxy, $(C_1-C_6)$alkyl, $(C_3-C_6)$cycloalkyl, $(C_1-C_6)$alkoxy, $(C_3-C_6)$cycloalkyloxy, $(C_1-C_6)$alkanoyl, $(C_1-C_6)$alkanoyloxy, trifluoromethyl, hydroxy$(C_1-C_6)$alkyl, —$(CH_2)_{1-4}P(=O)(OR_k)_2$, aryl, aryl$(C_1-C_6)$alkyl, or $NR_xR_y$;

one of $R_{17}$ and $R_{18}$ is hydroxy and the other is hydrogen, halo, hydroxy, $(C_1-C_6)$alkyl, $(C_3-C_6)$cycloalkyl, $(C_1-C_6)$alkoxy, $(C_3-C_6)$cycloalkyloxy, $(C_1-C_6)$alkanoyl, $(C_1-C_6)$alkanoyloxy, trifluoromethyl, azido, cyano, —$N(R_z)C(=O)N(R_{aa})(R_{ab})$, —$N(R_z)C(=O)OR_{ac}$, or $NR_{ad}R_{ae}$;

$R_{19}$ is hydrogen, $(C_1-C_6)$alkyl, $(C_3-C_6)$cycloalkyl, aryl, aryl$(C_1-C_6)$alkyl, or 2-cyanoethyl, wherein any aryl ring may optionally be substituted by 1, 2, or 3 halo, hydroxy, $(C_1-C_6)$alkyl, $(C_3-C_6)$cycloalkyl, $(C_1-C_6)$alkoxy, $(C_3-C_6)$cycloalkyloxy, $(C_1-C_6)$alkanoyl, $(C_1-C_6)$alkanoyloxy, trifluoromethyl, trifluoromethoxy, nitro, cyano, or amino;

$R_{20}$ is an amino acid or a peptide;

W is oxy, thio, or methylene;

each $R_w$ is independently hydrogen or $(C_1-C_6)$alkyl;

$R_x$ and $R_y$ are each independently hydrogen, $(C_1-C_6)$alkyl, $(C_3-C_6)$cycloalkyl, phenyl, benzyl, phenethyl, or $(C_1-C_6)$alkanoyl; or $R_x$ and $R_y$ together with the nitrogen to which they are attached are pyrrolidino, piperidino or morpholino;

$R_z$ is hydrogen, $(C_1-C_6)$alkyl, $(C_3-C_6)$cycloalkyl, phenyl, benzyl, or phenethyl;

$R_{aa}$ and $R_{ab}$ are each independently hydrogen, $(C_1-C_6)$alkyl, $(C_3-C_6)$cycloalkyl, phenyl, benzyl, or phenethyl; or $R_{aa}$ and $R_{ab}$ together with the nitrogen to which they are attached are pyrrolidino, piperidino or morpholino; and $R_{ag}$ is hydrogen, $(C_1-C_6)$alkyl, $(C_3-C_6)$cycloalkyl, phenyl, benzyl, or phenethyl; and $R_{ad}$ and $R_{ae}$ are each independently hydrogen, $(C_1-C_6)$alkyl, $(C_3-C_6)$cycloalkyl, phenyl, benzyl, phenethyl, or $(C_1-C_6)$alkanoyl; or $R_{ad}$ and $R_{ae}$ together with the nitrogen to which they are attached are pyrrolidino, piperidino or morpholino;

or a pharmaceutically acceptable salt thereof.

76. The method of claim 75 wherein $R_{16}$ is a nitrogen linked radical of formula VI:

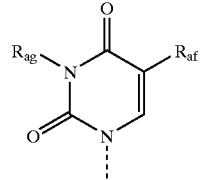

VI wherein $R_{af}$ is fluoro; and $R_{ag}$ is hydrogen.

77. The method of claim 75 wherein $R_{17}$ is hydroxy.

78. The method of claim 75 wherein $R_{18}$ is hydroxy.

79. The method of claim 75 wherein $R_{20}$ is an amino acid.

80. The method of claim 79 wherein the amino acid is an L-amino acid.

81. The method of claim 75 wherein $R_{20}$ is a peptide.

82. The method of claim 78 wherein $R_{16}$ is 5-fluorouracil; $R_{17}$ is hydrogen; $R_{19}$ is hydrogen; $R_{20}$ is N-linked L-phenylalanine; and W is oxy; or a pharmaceutically acceptable salt thereof.

83. The method of claim 78 wherein $R_{16}$ is 5-fluorouracil; $R_{17}$ is hydrogen; $R_{19}$ is hydrogen; $R_{20}$ is N-linked L-tryptophan; and W is oxy; or a pharmaceutically acceptable salt thereof.

84. The method of claim 75 wherein $R_{20}$ is a nitrogen linked radical of formula III:

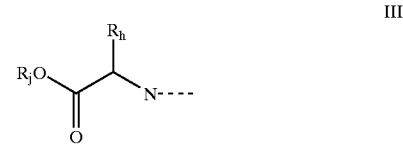

III wherein $R_h$ is hydrogen, $(C_1-C_6)$alkyl, $(C_3-C_6)$cycloalkyl, $(C_3-C_6)$cycloalkyl$(C_1-C_6)$alkyl, $(C_1-C_6)$alkyl-S—$(C_1-C_6)$alkyl-, aryl, heteroaryl, aryl$(C_1-C_6)$alkyl, or heteroaryl$(C_1-C_6)$alkyl; wherein any aryl or heteroaryl may optionally be substituted with 1, 2, or 3 Z; $R_j$ is hydrogen, $(C_1-C_6)$alkyl, phenyl, benzyl, or phenethyl; and wherein each Z is independently halo, hydroxy, $(C_1-C_6)$alkyl, $(C_3-C_6)$cycloalkyl, $(C_1-C_6)$alkoxy, $(C_3-C_6)$cycloalkyloxy, $(C_1-C_6)$alkanoyl, $(C_1-C_6)$alkanoyloxy, trifluoromethyl, trifluoromethoxy, nitro, cyano, or amino.

85. The method of claim 75 wherein $R_{20}$ is a nitrogen linked radical of formula VI:

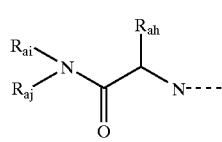

VI wherein $R_{ah}$ is hydrogen, $(C_1-C_6)$alkyl, $(C_3-C_6)$cycloalkyl, $(C_3-C_6)$cycloalkyl$(C_1-C_6)$alkyl, $(C_1-C_6)$alkyl-S—$(C_1-C_6)$alkyl-, aryl, heteroaryl, aryl$(C_1-C_6)$alkyl, or heteroaryl$(C_1-C_6)$alkyl; wherein any aryl or heteroaryl may optionally be substituted with 1, 2, or 3 Z; $R_{ai}$ and $R_{aj}$ are each independently hydrogen, $(C_1-C_6)$alkyl, $(C_3-C_6)$cycloalkyl, $(C_3-C_6)$cycloalkyl$(C_1-C_6)$alkyl, phenyl, benzyl, or phenethyl; and each Z is independently halo, hydroxy, $(C_1-C_6)$alkyl, $(C_3-C_6)$cycloalkyl, $(C_1-C_6)$alkoxy, $(C_3-C_6)$cycloalkyloxy, $(C_1-C_6)$alkanoyl, $(C_1-C_6)$alkanoyloxy, trifluoromethyl, trifluoromethoxy, nitro, cyano, or amino.

86. The method of claim 85 wherein $R_{ah}$ is hydrogen, $(C_1-C_6)$alkyl, aryl, heteroaryl, aryl$(C_1-C_6)$alkyl, or heteroaryl($C_1$–$C_6$)alkyl; wherein any aryl or heteroaryl may optionally be substituted with 1, 2, or 3 Z.

87. The method of claim 85 wherein $R_{ah}$ is hydrogen, ($C_1$–$C_6$)alkyl, phenylmethyl, or 3-indolylmethyl.

88. The method of claim 85 wherein $R_{ah}$ is phenylmethyl.

89. The method of claim 85 wherein $R_{ah}$ is 3-indolylmethyl.

90. The method of claim 85 wherein $R_{ai}$ and $R_{aj}$ are each independently hydrogen, ($C_1$–$C_6$)alkyl, or ($C_3$–$C_6$)cycloalkyl.

91. The method of claim 85 wherein $R_{ai}$ is hydrogen and $R_{aj}$ is methyl, cyclopropyl, or cyclohexyl.

92. The method of claim 85 wherein the carbon bearing $R_{ah}$ has the (S) absolute configuration.

93. The method of claim 85 wherein the carbon bearing $R_{ah}$ has the (R) absolute configuration.

94. A process for preparing a compound of claim 20 wherein $R_4$ is hydrogen, comprising deprotecting a corresponding compound of formula 44

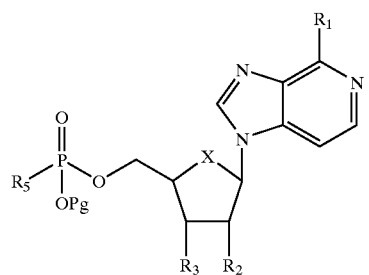

wherein Pg is a suitable removable protecting group.

95. A process for preparing a compound of claim 53 wherein $R_9$ is hydrogen comprising deprotecting a corresponding compound of formula 45

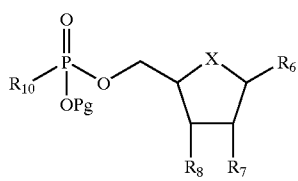

wherein Pg is a suitable removable protecting group.

96. A process for preparing a compound of formula V:

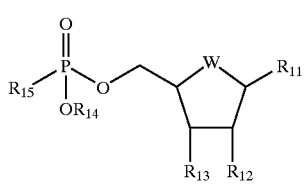

wherein $R_{11}$ is adenine, guanine, cytosine, thymine, 3-deazaadenine, or uracil, optionally substituted by 1, 2, or 3 U; wherein each U is independently halo, hydroxy, ($C_1$–$C_6$)alkyl, ($C_3$–$C_6$)cycloalkyl, ($C_1$–$C_6$)alkoxy, ($C_3$–$C_6$)cycloalkyloxy, ($C_1$–$C_6$)alkanoyl, ($C_1$–$C_6$)alkanoyl, ($C_1$–$C_6$)alkanoyloxy, trifluoromethyl, hydroxy($C_1$–$C_6$)alkyl, —$(CH_2)_{1-4}$P(=O)$(OR_v)_2$, aryl, aryl($C_1$–$C_6$)alkyl, or $NR_xR_y$;

one of $R_{12}$ and $R_{13}$ is azido and the other is hydrogen, halo, hydroxy, ($C_1$–$C_6$)alkyl, ($C_3$–$C_6$)cycloalkyl, ($C_1$–$C_6$)alkoxy, ($C_3$–$C_6$)cycloalkyloxy, ($C_1$–$C_6$)alkanoyl, ($C_1$–$C_6$)alkanoyloxy, trifluoromethyl, azido, cyano, —$N(R_z)C(=O)N(R_{aa})(R_{ab})$, —$N(R_z)C(=O)OR_{ac}$, or $NR_{ad}R_{ae}$;

$R_{14}$ is hydrogen;

$R_{15}$ is an amino acid or a peptide;

W is oxy, thio, or methylene;

each $R_w$ is independently hydrogen or ($C_1$–$C_6$)alkyl;

$R_x$ and $R_y$ are each independently hydrogen, ($C_1$–$C_6$)alkyl, ($C_3$–$C_6$)cycloalkyl, phenyl, benzyl, phenethyl, or ($C_1$–$C_6$)alkanoyl; or $R_x$ and $R_y$ together with the nitrogen to which they are attached are pyrrolidino, piperidino or morpholino;

$R_z$ is hydrogen, ($C_1$–$C_6$)alkyl, ($C_3$–$C_6$)cycloalkyl, phenyl, benzyl, or phenethyl;

$R_{aa}$ and $R_{ab}$ are each independently hydrogen, ($C_1$–$C_6$)alkyl, ($C_3$–$C_6$)cycloalkyl, phenyl, benzyl, or phenethyl; or $R_{aa}$ and $R_{ab}$ together with the nitrogen to which they are attached are pyrrolidino, piperidino or morpholino; and $R_{ac}$ is hydrogen, ($C_1$–$C_6$)alkyl, ($C_3$–$C_6$)cycloalkyl, phenyl, benzyl, or phenethyl; and $R_{ad}$ and $R_{ae}$ are each independently hydrogen, ($C_1$–$C_6$)alkyl, ($C_3$–$C_6$)cycloalkyl, phenyl, benzyl, phenethyl, or ($C_1$–$C_6$)alkanoyl; or $R_{ad}$ and $R_{ae}$ together with the nitrogen to which they are attached are pyrrolidino, piperidino or morpholino;

or a pharmaceutically acceptable salt thereof; the process comprising deprotecting a corresponding compound of formula 46

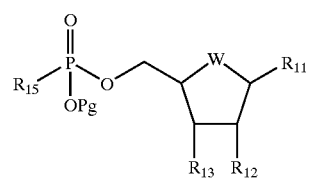

wherein Pg is a suitable removable protecting group.

97. A process for preparing a compound of formula VII:

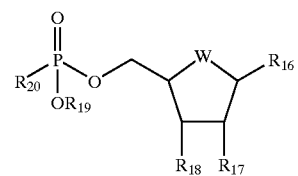

wherein $R_{16}$ is adenine, guanine, cytosine, thymine, 3-deazaadenine, or uracil, optionally substituted by 1, 2, or 3 U; wherein each U is independently halo, hydroxy, ($C_1$–$C_6$)alkyl, ($C_3$–$C_6$)cycloalkyl, ($C_1$–$C_6$)alkoxy, ($C_3$–$C_6$)cycloalkyloxy, ($C_1$–$C_6$)alkanoyl, ($C_1$–$C_6$)alkanoyloxy, trifluoromethyl, hydroxy($C_1$–$C_6$)alkyl, —$(CH_2)_{1-4}$P(=O)$(OR_w)_2$, aryl, aryl($C_1$–$C_6$)alkyl, or $NR_xR_y$;

one of $R_{17}$ and $R_{18}$ is hydroxy and the other is hydrogen, halo, hydroxy, ($C_1$–$C_6$)alkyl, ($C_3$–$C_6$)cycloalkyl, ($C_1$–$C_6$)alkoxy, ($C_3$–$C_6$)cycloalkyloxy, ($C_1$–$C_6$)

alkanoyl, (C₁–C₆)alkanoyloxy, trifluoromethyl, azido, cyano, —N(R_z)C(=O)N(R_{aa})(R_{ab}), —N(R_z)C(=O)OR_{ac}, or NR_{ad}R_{ae};

R₁₉ is hydrogen;

R₂₀ is an amino acid or a peptide;

W is oxy, thio, or methylene;

each R_w is independently hydrogen or (C₁–C₆)alkyl;

R_x and R_y are each independently hydrogen, (C₁–C₆)alkyl, (C₃–C₆)cycloalkyl, phenyl, benzyl, phenethyl, or (C₁–C₆)alkanoyl; or R_x and R_y together with the nitrogen to which they are attached are pyrrolidino, piperidino or morpholino;

R_z is hydrogen, (C₁–C₆)alkyl, (C₃–C₆)cycloalkyl, phenyl, benzyl, or phenethyl;

R_{aa} and R_{ab} are each independently hydrogen, (C₁–C₆)alkyl, (C₃–C₆)cycloalkyl, phenyl, benzyl, or phenethyl; or R_{aa} and R_{ab} together with the nitrogen to which they are attached are pyrrolidino, piperidino or morpholino; and R_{ac} is hydrogen, (C₁–C₆)alkyl, (C₃–C₆)cycloalkyl, phenyl, benzyl, or phenethyl; and R_{ad} and R_{ae} are each independently hydrogen, (C₁–C₆)alkyl, (C₃–C₆)cycloalkyl, phenyl, benzyl, phenethyl, or (C₁–C₆)alkanoyl; or R_{ad} and R_{ae} together with the nitrogen to which they are attached are pyrrolidino, piperidino or morpholino;

or a pharmaceutically acceptable salt thereof; the process comprising deprotecting a corresponding compound of formula 47:

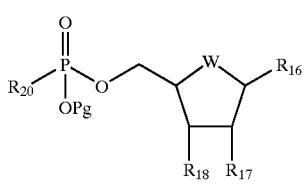

47 wherein Pg is a suitable removable protecting group.

98. The compound 3'-Azido-3'-deoxythymidine-5'-methylaminoglycinylphosphoramidate; 3'-Azido-3'-deoxythymidine-5'-methylamino-L-alaninylphosphoramidate; 3'-Azido-3'-deoxythymidine-5'-methylamino-L-valinylphosphoramidate; 3'-Azido-3'-deoxythymidine-5'-methylamino-L-leucinyl-phosphoramidate; 3'-Azido-3'-deoxythymidine-5'-methylamino-L-phenylalaninyl-phosphoramidate; 3'-Azido-3'-deoxythymidine-5'-methylamino-D-phenylalaninyl-phosphoramidate; 3'-Azido-3'-deoxythymidine-5'-methylamino-L-tyrosinylphosphoramidate; 3'-Azido-3'-deoxythymidine-5'-methylamino-L-tryptophanyl-phosphoramidate; 3'-Azido-3'-deoxythymidine-5'-methylamino-D-tryptophanyl-phosphoramidate; 3'-Azido-3'-deoxythymidine-5'-ethylamino-L-tryptophanyl-phosphoramidate; 3'-Azido-3'-deoxythymidine-5'-isopropylamino-L-tryptophanyl-phosphoramidate; 3'-Azido-3'-deoxythymidine-5'-cyclopropylamino-L-tryptophanyl-phosphoramidate; or 3'-Azido-3'-deoxythymidine-5'-cyclohexylamino-L-tryptophanyl-phosphoramidate; or a pharmaceutically acceptable salt thereof.

99. A composition of matter comprising a compound of formula V:

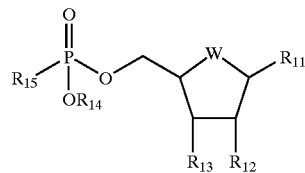

V wherein

R₁₁ is adenine, guanine, cytosine, thymine, or uracil, optionally substituted by 1, 2, or 3 U; wherein each U is independently halo, hydroxy, (C₁–C₆)alkyl, (C₃–C₆)cycloalkyl, (C₁–C₆)alkoxy, (C₃–C₆)cycloalkyloxy, (C₁–C₆)alkanoyl, (C₁–C₆)alkanoyloxy, trifluoromethyl, hydroxy(C₁–C₆)alkyl, —(CH₂)₁₋₄P(=O)(OR_w)₂, aryl, aryl(C₁–C₆)alkyl, or NR_xR_y;

one of R₁₂ and R₁₃ is azido and the other is hydrogen, halo, hydroxy, (C₁–C₆)alkyl, (C₃–C₆)cycloalkyl, (C₁–C₆)alkoxy, (C₃–C₆)cycloalkyloxy, (C₁–C₆)alkanoyl, (C₁–C₆)alkanoyloxy, trifluoromethyl, azido, cyano, —N(R_z)C(=O)N(R_{aa})(R_{ab}), —N(R_z)C(=O)OR_{ac}, or NR_{ad}R_{ae};

R₁₄ is hydrogen, (C₁–C₆)alkyl, (C₃–C₆)cycloalkyl, aryl, aryl(C₁–C₆)alkyl, or 2-cyanoethyl, wherein any aryl ring may optionally be substituted by 1, 2, or 3 halo, hydroxy, (C₁–C₆)alkyl, (C₃–C₆)cycloalkyl, (C₁–C₆)alkoxy, (C₃–C₆)cycloalkyloxy, (C₁–C₆)alkanoyl, (C₁–C₆)alkanoyloxy, trifluoromethyl, trifluoromethoxy, nitro, cyano, or amino;

R₁₅ is an amino acid or a peptide;

W is oxy, thio, or methylene;

each R_w is independently hydrogen or (C₁–C₆)alkyl;

R_x and R_y are each independently hydrogen, (C₁–C₆)alkyl, (C₃–C₆)cycloalkyl, phenyl, benzyl, phenethyl, or (C₁–C₆)alkanoyl; or R_x and R_y together with the nitrogen to which they are attached are pyrrolidino, piperidino or morpholino;

R_z is hydrogen, (C₁–C₆)alkyl, (C₃–C₆)cycloalkyl, phenyl, benzyl, or phenethyl;

R_{aa} and R_{ab} are each independently hydrogen, (C₁–C₆)alkyl, (C₃–C₆)cycloalkyl, phenyl, benzyl, or phenethyl; or R_{aa} and R_{ab} together with the nitrogen to which they are attached are pyrrolidino, piperidino or morpholino; and R_{ac} is hydrogen, (C₁–C₆)alkyl, (C₃–C₆)cycloalkyl, phenyl, benzyl, or phenethyl; and R_{ad} and R_{ae} are each independently hydrogen, (C₁–C₆)alkyl, (C₃–C₆)cycloalkyl, phenyl, benzyl, phenethyl, or (C₁–C₆)alkanoyl; or R_{ad} and R_{ae} together with the nitrogen to which they are attached are pyrrolidino, piperidino or morpholino;

or a pharmaceutically acceptable salt thereof;

linked to a reagent that is capable of targeting the compound to a tumor or cancer cell; wherein the tumor or cancer cell is non phagocytic.

100. The composition of claim 99 wherein the reagent is capable of targeting the compound to a breast cancer cell.

101. The therapeutic method of claim 72, wherein the mammal is a human.

* * * * *

UNITED STATES PATENT AND TRADEMARK OFFICE
CERTIFICATE OF CORRECTION

PATENT NO. : 6,475,985 B1
DATED : November 5, 2002
INVENTOR(S) : Carston R. Wagner and George W. Griesgraber It is certified that error appears in the above-identified patent and that said Letters Patent is hereby corrected as shown below:

Column 37,
Line 19, delete "—(CH$_2$)$_{1-4}$ P(=O)(OR$_k$)$_2$" and insert -- —(CH$_2$)$_{1-4}$ P(=O)(OR$_W$)$_2$ --, therefor.
Line 21, delete "or" after "one" and insert -- of --, therefor.
Line 26, insert -- ; -- after "NR$_{ad}$R$_{ae}$"
Line 37, delete "R$_v$" after "each" and insert -- R$_w$ --, therefor.
Line 65, delete "—(CH$_2$)$_{1-4}$ P(=O)(OR$_k$)$_2$" and insert -- —(CH$_2$)$_{1-4}$ P(=O)(OR$_W$)$_2$ --, therefor.

Column 38,
Line 20, delete "in" before "N-linked" and insert -- is --, therefor.

Column 41,
Line 19, insert -- is -- after "R$_2$".
Line 20, delete "—C(=O)N(R$_a$)(R$_f$)" and insert -- —C(=O)N(R$_e$)(R$_f$) --, therefor.
Line 24, delete "R$_e$" and insert -- R$_c$ --, therefor.
Line 47, delete "R$^5$" and insert -- R$_5$ --, therefor.

Column 42,
Line 46, insert -- ; -- after "amino"
Line 47, delete "—N(R$_b$)C(=O)N(R$_p$)(R$_q$)" and insert -- —N(R$_o$)C(=O)N(R$_p$)(R$_q$) --, therefor.
Lines 47-48, delete "N(R$_o$)C(=O)O(R$_r$)" and insert -- "—N(R$_o$)C(=O)OR$_r$ --, therefor.
Line 51, delete "NR$_a$R$_c$" and insert -- NR$_s$R$_t$; --, therefor.

Column 43,
Line 28, delete "trifluoromethyl" before "nitro" and insert -- trifluoromethoxy --, therefor.
Line 44, delete "or —(CH$_2$)(C$_1$-C$_6$)," after "alkyl".
Line 46, delete "—N(R$_n$C(=O)N(R$_p$)(R$_q$)" and insert -- —N(R$_o$)C(=O)N(R$_p$)(R$_q$) --, therefor.

Column 44,
Line 38, delete "R$_{af}$" and insert -- R$_{ai}$ --, therefor.
Line 41, delete "," after "hydrogen".

UNITED STATES PATENT AND TRADEMARK OFFICE
CERTIFICATE OF CORRECTION

PATENT NO. : 6,475,985 B1
DATED : November 5, 2002
INVENTOR(S) : Carston R. Wagner and George W. Griesgraber It is certified that error appears in the above-identified patent and that said Letters Patent is hereby corrected as shown below:

Column 45,
Line 22, delete "—(CH$_2$)$_{1-4}$ P(=O)(OR$_k$)$_2$" and insert -- —(CH$_2$)$_{1-4}$ P(=O)(OR$_W$)$_2$ --, therefor.
Line 57, delete "R$_{ag}$" and insert -- R$_{ac}$ --, therefor.

Column 47,
Line 65, delete "(C$_1$-C$_6$)alkanoyl,".
Line 66, delete "—(CH$_2$)$_{1-4}$ P(=O)(OR$_v$)$_2$" and insert -- —(CH$_2$)$_{1-4}$ P(=O)(OR$_W$)$_2$ --, therefor.

Column 49,
Line 14, delete "R$_x$" and insert -- R$_z$ --, therefor.

Signed and Sealed this

Twenty-seventh Day of May, 2003

JAMES E. ROGAN
*Director of the United States Patent and Trademark Office*